United States Patent
Halperin et al.

(10) Patent No.: US 11,891,448 B2
(45) Date of Patent: *Feb. 6, 2024

(54) GLYCATED CD59 PEPTIDES, THEIR PREPARATION, AND USES THEREOF

(71) Applicant: President and Fellows of Harvard College, Cambridge, MA (US)

(72) Inventors: Jose A. Halperin, Brookline, MA (US); Michael Chorev, Chestnut Hill, MA (US)

(73) Assignee: President and Fellows of Harvard College, Cambridge, MA (US)

(*) Notice: Subject to any disclaimer, the term of this patent is extended or adjusted under 35 U.S.C. 154(b) by 24 days.

This patent is subject to a terminal disclaimer.

(21) Appl. No.: 17/516,508

(22) Filed: Nov. 1, 2021

(65) Prior Publication Data

US 2022/0162333 A1     May 26, 2022

Related U.S. Application Data

(60) Continuation of application No. 15/995,370, filed on Jun. 1, 2018, now Pat. No. 11,161,910, which is a division of application No. 14/724,911, filed on May 29, 2015, now abandoned, which is a division of application No. 13/818,775, filed as application No. PCT/US2011/049118 on Aug. 25, 2011, now Pat. No. 9,068,006.

(60) Provisional application No. 61/377,060, filed on Aug. 25, 2010.

(51) Int. Cl.
    *C07K 16/28*      (2006.01)
    *G01N 33/68*      (2006.01)
    *C07K 14/705*      (2006.01)

(52) U.S. Cl.
CPC .... *C07K 16/2896* (2013.01); *C07K 14/70596* (2013.01); *G01N 33/6842* (2013.01); *G01N 33/6872* (2013.01); *C07K 2317/34* (2013.01); *C07K 2317/54* (2013.01); *C07K 2317/55* (2013.01); *G01N 2333/70596* (2013.01); *G01N 2440/38* (2013.01); *G01N 2800/042* (2013.01)

(58) Field of Classification Search
None
See application file for complete search history.

(56) References Cited

U.S. PATENT DOCUMENTS

| | | |
|---|---|---|
| 4,281,061 A | 7/1981 | Zuk et al. |
| 4,778,752 A | 10/1988 | Curtiss et al. |
| 4,816,567 A | 3/1989 | Cabilly et al. |
| 4,950,712 A | 8/1990 | Letourneur et al. |
| 5,225,539 A | 7/1993 | Winter |
| 5,248,832 A | 9/1993 | Lee |
| 5,470,759 A | 11/1995 | Sugiyama et al. |
| 5,585,089 A | 12/1996 | Queen et al. |
| 5,686,316 A | 11/1997 | Fiechtner et al. |
| 5,693,762 A | 12/1997 | Queen et al. |
| 5,789,208 A | 8/1998 | Sharon |
| 5,853,703 A | 12/1998 | Cerami et al. |
| 5,859,205 A | 1/1999 | Adair et al. |
| 6,180,370 B1 * | 1/2001 | Queen .............. A61P 31/12 |
| | | 435/69.6 |
| 6,485,911 B1 | 11/2002 | St. George-Hyslop et al. |
| 6,835,535 B2 | 12/2004 | Gretton et al. |
| 6,835,545 B2 | 12/2004 | Halperin |
| 7,049,082 B2 | 5/2006 | Halperin |
| 7,439,300 B2 | 10/2008 | Yanai et al. |
| 7,439,330 B2 | 10/2008 | Halperin |
| 7,501,286 B2 | 3/2009 | Gygi et al. |
| 7,767,791 B2 | 8/2010 | Halperin |
| 7,833,725 B2 | 11/2010 | Halperin |
| 8,008,024 B2 | 8/2011 | Halperin |
| 8,093,009 B2 | 1/2012 | Halperin |
| 8,298,779 B2 | 10/2012 | Halperin |
| 8,404,451 B2 | 3/2013 | Halperin |
| 9,068,006 B2 * | 6/2015 | Halperin ............ C07K 16/2896 |
| 11,161,910 B2 * | 11/2021 | Halperin ............ A61P 3/10 |
| 2003/0036207 A1 | 2/2003 | Washburn et al. |
| 2004/0110226 A1 | 6/2004 | Lazar et al. |
| 2004/0119010 A1 | 6/2004 | Perryman et al. |
| 2004/0166531 A1 | 8/2004 | Halperin |

(Continued)

FOREIGN PATENT DOCUMENTS

| | | |
|---|---|---|
| EP | 0394035 A2 | 10/1990 |
| EP | 1789449 A1 | 5/2007 |

(Continued)

OTHER PUBLICATIONS

Kipriyanov, Sergey M., and Fabrice Le Gall. "Generation and production of engineered antibodies." Molecular biotechnology 26.1 (2004): 39-60. (Year: 2004).*

(Continued)

*Primary Examiner* — Michael Szperka
*Assistant Examiner* — Lia E Taylor
(74) *Attorney, Agent, or Firm* — Clark & Elbing LLP

(57) ABSTRACT

The present invention provides glycated Amadori products of the CD59 peptide and fragments thereof to be used as tools and among methods for the diagnosis and prognosis of pre-diabetes and diabetes. Certain aspects of the invention include glycated Amadori products of CD59 and fragments thereof to be used for the generation of antibodies and antibody fragments. Still other aspects of the invention include methodologies for the preparation of glycated Amadori products of CD59, fragments thereof, the inventive antibodies, and antibody fragments.

8 Claims, 10 Drawing Sheets

Specification includes a Sequence Listing.

(56) References Cited

U.S. PATENT DOCUMENTS

| | | |
|---|---|---|
| 2004/0219606 A1 | 11/2004 | Halperin |
| 2005/0032128 A1* | 2/2005 | Halperin .............. G01N 33/566 530/388.22 |
| 2006/0257936 A1 | 11/2006 | Halperin |
| 2008/0081038 A1 | 4/2008 | Cho et al. |
| 2009/0023157 A1 | 1/2009 | Lee et al. |
| 2009/0028884 A1 | 1/2009 | Schwabe |
| 2009/0191574 A1 | 7/2009 | Halperin |
| 2010/0112708 A1 | 5/2010 | Pappin et al. |
| 2010/0331200 A1 | 12/2010 | Gordon et al. |
| 2013/0224211 A1 | 8/2013 | Halperin et al. |
| 2014/0024056 A1 | 1/2014 | Chorev et al. |
| 2015/0315286 A1 | 11/2015 | Halperin et al. |
| 2018/0265589 A1 | 9/2018 | Halperin et al. |

FOREIGN PATENT DOCUMENTS

| | | |
|---|---|---|
| WO | WO-88/06798 A1 | 9/1988 |
| WO | WO-89/06798 A1 | 7/1989 |
| WO | WO-90/06516 A1 | 6/1990 |
| WO | WO-97/49429 A1 | 12/1997 |
| WO | WO-98/19711 A1 | 5/1998 |
| WO | WO-99/22242 A2 | 5/1999 |
| WO | WO-02/04638 A1 | 1/2002 |
| WO | WO-2004/106941 A2 | 12/2004 |
| WO | WO-2006/009533 A1 | 1/2006 |
| WO | WO-2006/086098 A2 | 8/2006 |
| WO | WO-2008/137165 A1 | 11/2008 |
| WO | WO-2010/002278 A1 | 1/2010 |
| WO | WO-2012/109538 A2 | 8/2012 |

OTHER PUBLICATIONS

U.S. Appl. No. 14/724,911, Halperin.
Armbruster, "Fructosamine: structure, analysis, and clinical usefulness," Clin Chem. 33(12):2153-63 (1987).
Frolov et al., "Site-specific synthesis of Amadori-modified peptides on solid phase," J Pept Sci. 12(6):389-95 (2006).
International Search Report and Written Opinion for International Application No. PCT/US2011/049118, dated Apr. 30, 2012.
International Preliminary Report of Patentability for International Application No. PCT/US2011/049118, dated Mar. 7, 2013.
International Search Report and Written Opinion for International Application No. PCT/US2012/024645, dated Sep. 19, 2012.
Extended European Search Report for European Application No. 10185729.0, dated Jun. 1, 2011.
Extended European Search Report for European Application No. 10185831.4, dated May 27, 2011.
International Search Report for International Application No. PCT/US2004/019392, dated Jun. 6, 2005.
International Preliminary Report on Patentability for International Application No. PCT/US2004/019392, dated Dec. 20, 2006.
Invitation to Pay Additional Fees for International Application No. PCT/US2006/000310, mailed Jul. 11, 2006.
International Search Report and Written Opinion for International Application No. PCT/US2006/000310, dated Oct. 30, 2006.
International Preliminary Report on Patentability for International Application No. PCT/US2006/000310, dated Jul. 19, 2007.
International Search Report and Written Opinion for International Application No. PCT/US2008/005831, dated Aug. 27, 2008.
International Preliminary Report on Patentability for International Application No. PCT/US2008/005831, dated Nov. 19, 2009.
Office Action for U.S. Appl. No. 09/835,752, dated Oct. 21, 2002.
Reply to Office Action for U.S. Appl. No. 09/835,752, dated Mar. 19, 2003.
Office Action for U.S. Appl. No. 09/835,752, dated Jun. 13, 2003.
Reply to Office Action for U.S. Appl. No. 09/835,752, dated Jul. 11, 2003.
Office Action for U.S. Appl. No. 09/835,752, dated Oct. 3, 2003.
Reply to Office Action for U.S. Appl. No. 09/835,752, dated Oct. 20, 2003.
Notice of Allowance for U.S. Appl. No. 09/835,752, dated Dec. 5, 2003.
Office Action for U.S. Appl. No. 10/833,581, dated Mar. 24, 2005.
Reply to Office Action for U.S. Appl. No. 10/833,581, dated Sep. 26, 2005.
Notice of Allowance for U.S. Appl. No. 10/833,581, dated Dec. 15, 2005.
Office Action for U.S. Appl. No. 11/413,130, dated Oct. 5, 2006.
Reply to Office Action for U.S. Appl. No. 11/413,130, dated Dec. 7, 2006.
Office Action for U.S. Appl. No. 11/413,130, dated Jul. 17, 2007.
Reply to Office Action for U.S. Appl. No. 11/413,130, dated Jan. 16, 2008.
Notice of Allowance for U.S. Appl. No. 11/413,130, dated Jun. 16, 2008.
Amendment for U.S. Appl. No. 11/413,130, dated Sep. 15, 2008.
Office Action for U.S. Appl. No. 12/244,851, dated Dec. 15, 2010.
Reply to Office Action for U.S. Appl. No. 12/244,851, dated Mar. 11, 2011.
Notice of Allowance for U.S. Appl. No. 12/244,851, dated May 16, 2011.
Office Action for U.S. Appl. No. 13/206,196, dated Jan. 27, 2012.
Reply to Office Action for U.S. Appl. No. 13/206,196, dated Apr. 27, 2012.
Notice of Allowance for U.S. Appl. No. 13/206,196, dated Jun. 25, 2012.
Office Action for U.S. Appl. No. 10/870,342, dated Feb. 27, 2006.
Restriction Requirement for U.S. Appl. No. 10/870,342, dated Oct. 11, 2006.
Office Action for U.S. Appl. No. 10/870,342, dated Mar. 23, 2007.
Reply to Restriction Requirement for U.S. Appl. No. 10/870,342, dated Dec. 11, 2006.
Reply to Office Action for U.S. Appl. No. 10/870,342, dated Sep. 24, 2007.
Notice of Allowance for U.S. Appl. No. 10/870,342, dated Nov. 9, 2007.
Reply to Office Action for U.S. Appl. No. 10/870,342, dated Jan. 29, 2008.
Notice of Allowance for U.S. Appl. No. 10/870,342, dated May 13, 2008.
Office Action for U.S. Appl. No. 11/794,635, dated Mar. 16, 2010.
Reply to Office Action for U.S. Appl. No. 11/794,635, dated Jul. 14, 2010.
Notice of Allowance for U.S. Appl. No. 11/794,635, dated Jul. 26, 2010.
Office Action for U.S. Appl. No. 12/917,271, dated Jan. 25, 2011.
Reply to Office Action for U.S. Appl. No. 12/917,271, dated Apr. 25, 2011.
Notice of Allowance for U.S. Appl. No. 12/917,271, dated May 13, 2011.
Notice of Allowance for U.S. Appl. No. 12/917,271, dated Sep. 30, 2011.
Office Action for U.S. Appl. No. 13/313,517, dated Jan. 26, 2012.
Reply to Office Action for U.S. Appl. No. 13/313,517, dated Apr. 26, 2012.
Office Action for U.S. Appl. No. 13/313,517, dated May 14, 2012.
Reply to Office Action for U.S. Appl. No. 13/313,517, dated Oct. 10, 2012.
Notice of Allowance for U.S. Appl. No. 13/313,517, dated Nov. 29, 2012.
NCBI Blast for Accession No. M95708I. Retrieved on Jan. 17, 1995 (1 page).
Acosta et al., "Complement and complement regulatory proteins as potential molecular targets for vascular diseases," Curr Pharm Des. 10:1-9 (2004).
Acosta et al., "Molecular basis for a link between complement and the vascular complications of diabetes," Proc Natl Acad Sci U.S.A. 97(10):5450-5 (2000).
Angeletti, "Design of useful peptide antigens," J Biomol Tech. 10(1):2-10 (1999).

(56) References Cited

OTHER PUBLICATIONS

Baerga-Ortiz et al., "Epitope mapping of a monoclonal antibody against human thrombin by H/D-exchange mass spectrometry reveals selection of a diverse sequence in a highly conserved protein," Protein Sci. 11(6):1300-8 (2002).

Benzaquen et al., "Terminal complement proteins C5b-9 release basic fibroblast growth factor and platelet-derived growth factor from endothelial cells," J Exp Med. 179(3):985-92 (1994).

Bird et al., "Single-chain antigen-binding proteins," Science. 242(4877):423-6 (1988).

Bodian et al., "Mutational analysis of the active site and antibody epitopes of the complement-inhibtory glycoprotein, CD59," J Exp Med. 185(3):507-16 (1997).

Bunn et al., "Further identification of the nature and linkage of the carbohydrate in hemoglobin A1c," Biochem Biophys Res Commun. 67(1):103-9 (1975).

Carganico et al., "Building blocks for the synthesis of post-translationally modified glycated peptides and proteins," J Pept Sci. 15(2):67-71 (2009).

Darlak et al., "Facile preparation of disulfide-bridged peptides using the polymer-supported oxidant CLEAR-OX," J Pept Res. 63(3):303-12 (2004).

Davies et al., "CD59, an LY-6-like protein expressed in human lymphoid cells, regulates the action of the complement membrane attack complex on homologous cells," J Exp Med. 170(3):637-54 (1989).

Desiderio, "Mass spectrometric analysis of neuropeptidergic systems in the human pituitary and cerebrospinal fluid," J Chromatogr B Biomed Sci Appl. 731(1):3-22 (1999).

Falk et al., "Ultrastructural localization of the membrane attack complex of complement in human renal tissues," Am J Kidney Dis. 9(2):121-8 (1987).

Fischer et al., "The carbohydrate moiety in hemoglobin A1C is present in the ring form," FEBS Lett. 135(1):145-7 (1981).

Fletcher et al., "Structure of a soluble, glycosylated form of the human complement regulatory protein CD59," Structure. 2(3):185-99 (1994).

Halperin et al., "Properties of Na+-K+ pump in human red cells with increased number of pump sites," J Clin Invest. 80(1):128-37 (1987).

Halperin et al., "Terminal complement complex C5b-9 stimulates mitogenesis in 3T3 cells," J Clin Invest. 91(5):1974-8 (1993).

Halperin et al., "Transient changes in erythrocyte membrane permeability are induced by sublytic amounts of the complement membrane attack complex (C5b-9)," Blood. 81(1):200-5 (1993).

Harlow et al., Antibodies: A Laboratory Manual. 321-3 (1998).

Harvey, "Matrix-assisted laser desorption/ionization mass spectrometry of carbohydrates," Mass Spectrom Rev. 18(6):349-450 (1999).

Hughes et al., "Isolation and characterization of a membrane protein from rat erythrocytes which inihibits lysis by the membrane attack complex of rat complement," Biochem J. 284(Pt 1):169-76 (1992).

Huston et al., "Protein engineering of antibody binding sites: recovery of specific activity in an anti-digoxin single-chain Fv analogue produced in *Escherichia coli*," Proc Natl Acad Sci U S A. 85(16):5879-83 (1988).

Jacobson et al., "Glycation of protein by ADP-ribose," Mol Cell Biochem. 138(1-2):207-12 (1994).

Jakus et al., "Advanced glycation end-products and the progress of diabetiic vascular complications," Physiol Res. 53(2):131-42 (2004).

Johansen et al., "Analysis and prediction of mammalian protein glycation," Glycobiology. 16(9):844-53 (2006).

Kaiser et al., "Color test for detection of free terminal amino groups in the solid-phrase synthesis of peptides," Anal Biochem. 34(2):595-8 (1970).

Kim et al., "Multiple sclerosis: an important role for post-translational modifications of myelin basic protein in pathogenesis," Mol Cell Proteomics. 2(7):453-62 (2003).

Keonig et al., "Structure of carbohydrate of hemoglobin A1c," J Biol Chem. 252(9):2992-7 (1977).

Köhler et al., "Continuous cultures of fused cells secreting antibody of predefined specificity," Nature. 256(5517):495-7 (1975).

Köhler et al., "Derivation of specific antibody-producing tissue culture and tumor lines by cell fusion," Eur J Immunol. 6(7):511-9 (1976).

Lapolla et al., "The role of mass spectrometry in the study of non-enzymatic protein glycation in diabetes," Mass Spectrom Rev. 19(5):279-304 (2000).

Monnier et al., Maillard reaction in food and nutrition. American Chemical Society. Waller, 431-49 (1983).

Monnier et al., "Non-enzymatic glycosylation and browning of proteins in diabetes," Clin Endocrinol Metab. 11(2):431-52 (1982).

Myint et al., "Immunological detection of glycated proteins in normal and streptozotocin-induced diabetic rats using anti hexitol-lysine IgG," Biochim Biophys Acta. 1272(2):73-9 (1995).

Nakou et al., "Gene network analysis of bone marrow mononuclear cells reveals activation of multiple kinase pathways in human systemic lupus erythematosus," PLoS One. 5(10):e13351 (2010) (9 pages).

Ninomiya et al., "Contribution of the N-linked carbohydrate of erythrocyte antigen CD59 to its complement-inhibitory activity," J Biol Chem. 267(12):8404-10 (1992).

Ordóñez et al., "Increased levels of citrullinated antithrombin in plasma of patients with rheumatoid arthritis and colorectal adenocracinoma determined by a newly developed ELISA using a specific monoclonal antibody," Thromb Haemost. 104(6):1143-9 (2010).

Philbrick et al., "The CD59 antigen is a structural homolougue of murine Ly-6 antigens but lacks interferon inducibility," Eur J Immunol. 20(1):87-92 (1990).

Qin et al., "A role of glycated human CD59 and the complement system in the pathogenesis of chronic vascular complications of diabetes," Elsevier. 2(9):1382-3 (2002).

Qin et al., "Genomic structure, functional comparison, and tissue distribution of mouse Cd59a and Cd59b," Mamm Genome. 12(8):582-9 (2001).

Rosoklija et al., "Local activation of the complement system in endoneurial microvessels of diabetic neuropathy," Acta Neuropathol. 99(1):55-62 (2000).

Suzuki et al., "Immunofluorescence staining of renal biopsy samples in patients with diabetic nephropathy in non-insulin-dependent diabetes mellitus using monoclonal antibody to reduced glycated lysine," J Diabetes Complications. 10(6):314-9 (1996).

Takata et al., "Glycated Cu,Zn-superoxide dismutase in rat lenses: evidence for the presence of fragmentation in vivo," Biochem Biophys Res Commun. 219(1):243-8 (1996).

Ulrich et al., "Protein glycation, diabetes, and aging," Recent Prog Horm Res. 56:1-21 (2001).

Van Den Berg et al., "The sheep analogue of human CD59: purification and characterization of its complement inhibitory activity," Immunology. 78(3):349-57 (1993).

Wagner et al., "Induction of matrix protein synthesis in human glomerular mesangial cells by the terminal complement complex," Exp Nephrol. 2(1):51-6 (1994).

Walton et al., "Synthesis of N-(1-deoxyhexitol-1-yl)amino acids, reference compounds for the nonenzymic glycosylation of proteins," Carbohydr Res. 128(1):37-49 (1984).

Ward et al., Binding activities of a repertoire of single immunoglobulin variable domains secreted from *Escherichia coli*. 341(6242):544-6 (1989).

Weiss et al., "Immunoflorescent characteristics of the diabetic cornea," Cornea. 9(2):131-8 (1990).

Wilen et al., "Strategies in optical resolutions," Tetrahedron. 33(21):2725-36 (1971).

Wilen, Tables of resolving agents and optical resolutions. Eliel, 268-90 (1972).

Yu et al., "Mapping the active site of CD59," J Exp Med. 185(4):745-53 (1997).

Zhang et al., "Early complement activation and decreased levels of glycosylphosphatidylinositol-anchored complement inhibitors in human and experimental diabetic retinopathy," Diabetes. 51(12):3499-504 (2002).

(56) References Cited

OTHER PUBLICATIONS

Zhao et al., "Amplified gene expression in CD59-transfected Chinese hamster ovary cells confers protection against the membrane attack complex of human complement," J Biol Chem. 266(20):13418-22 (1991).
Curtiss et al. "A novel method for generating region-specific monoclonal antibodies to modified proteins. Application to the identification of human glucosylated low density lipoproteins" J Clin Invest. 72(4):1427-38 (1983).
Marimuthu et al.,"A comprehensive map of the human urinary proteome," available in PMC Oct. 30, 2014, published in final edited form as J Proteome Res. 10(6):2734-43 (2011) (20 pages).
Ukita et al. "Urinary excretion of glycated protein determined with a specific radioimmunoassay" Clin Chem. 37(4):504-7 (1991).
Nakayama et al. "Quantitative enzyme-linked immunosorbent assay (ELISA) for non-enzymatically glycated serum protein." J Immunol Methods. 99(1):95-100 (1987).
International Search Report and Written Opinion for International Patent Application No. PCT/US2012/065811, dated Apr. 3, 2013 (11 pages).
Delpierre et al., "Fructosamine 3-kinase is involved in an intracellular deglycation pathway in human erythrocytes," Biochem J. 365(Pt 3):801-8 (2002).
Ghosh et al., "Blood levels of glycated CD59 (GCD59) as a novel biomarker for screening and diagnosis of gestational diabetes mellitus," Poster Presentation (2015) (1 page).
Ghosh et al., "A specific and sensitive assay for blood levels of glycated CD59: a novel biomarker for diabetes," Am J Hematol. 88(8):670-6 (2013).
Ghosh et al., "Role of complement and complement regulatory proteins in the complications of diabetes," Endocr Rev. 36(3):272-88 (2015).
Ghosh et al., "Glycation of the complement regulatory protein CD59 is a novel biomarker for glucose handling in humans," J Clin Endocrinol Metab. 99(6):E999-E1006 (2014).
Witztum et al., "Nonenzymatic glucosylation of homologous low density lipoprotein and albumin renders them immunogenic in the guinea pig," Proc Natl Acad Sci U.S.A. 80(9):2757-61 (1983).
Yoshioka et al., "Variations of 1-deoxyglucose(1,5-anhydroglucitol) content in plasma from patients with insulin-dependent diabetes mellitus," Clin Chem. 29(7):1396-8 (1983).
Nguyen et al., "Early glycation products of endothelial plasma membrane proteins in experimental diabetes," Biochim Biophys Acta. 1762(1):94-102 (2006).
Millipore, "Protein blotting handbook," <http://web.mnstate.edu/provost/ProteinBlottingBook.pdf>, (56 pages).
Novus News, "Why Choose Rabbit Monoclonal Antibodies?" <http://www.novusbio.com/antibody-news/antibodies/using-rabbit-polyclonal-antibodies>, (1 page).
Chen et al., "Enhancement and destruction of antibody function by somatic mutation: unequal occurrence is controlled by V gene combinatorial associations," EMBO J. 14(12):2784-94 (1995).
Kussie et al., "A single engineered amino acid substitution changes antibody fine specificity," J Immunol. 152(1):146-52 (1994).
Bost et al., "Antibodies against a peptide sequence within the HIV envelope protein crossreacts with human interleukin-2," Immunol Invest. 17(6&7):577-586 (1988).
Colman, "Effects of amino acid sequence changes on antibody-antigen interactions," Res Immunol. 145(1):33-6 (1994).
Rudikoff et al., "Single amino acid substitution altering antigen-binding specificity," Proc Natl Acad Sci USA. 79(6):1979-83 (1982).
Bendayan, "Possibilities of false immunocytochemical results generated by the use of monoclonal antibodies: the example of the anti-proinsulin antibody," J Histochem Cytochem. 43(9):881-6 (1995).
Stryer, Protein Structure and Function, *Biochemistry* (4th Edition), W.H. Freeman and Company, 18-23 (1995).
Janeway et al., "The interaction of the antibody molecule with specific antigen," <https://www.ncbi.nlm.gov/books/NBK27160/>, retrieved Nov. 25, 2020 (2001) (5 pages).
Frank, Chapter 4: Specificity and Cross-Reactivity, *Immunology and Evolution of Infection Disease*. Princeton University Press, 33-56 (2002) (33 pages).
Griffiths et al., "Strategies for selection of antibodies by phage display," Curr Opin Biotechnol. 9(1):102-8 (1998).
Kipriyanov et al., "Generation and production of engineered antibodies," Molecular Biotechnology. 26: 36-60 (2004).
Ansari et al., "Amadori glycated proteins: role in production of autoantibodies in diabetes mellitus and effect of inhibitors on non-enzymatic glycation," Aging Dis. 4(1): 50-56 (2013).
Janeway et al., "Immunobiology: The Immune System in Health and Disease," NCBI Bookshelf, <https://www.ncbi.nlm.nih.gov/books/NBK27160/>, retrieved Nov. 25, 2020 (2001) (5 pages).

* cited by examiner

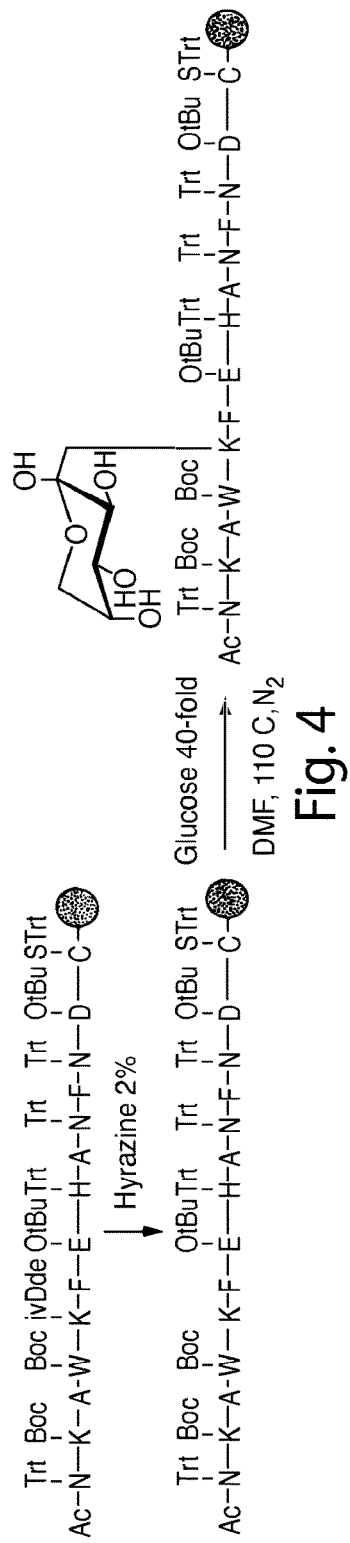
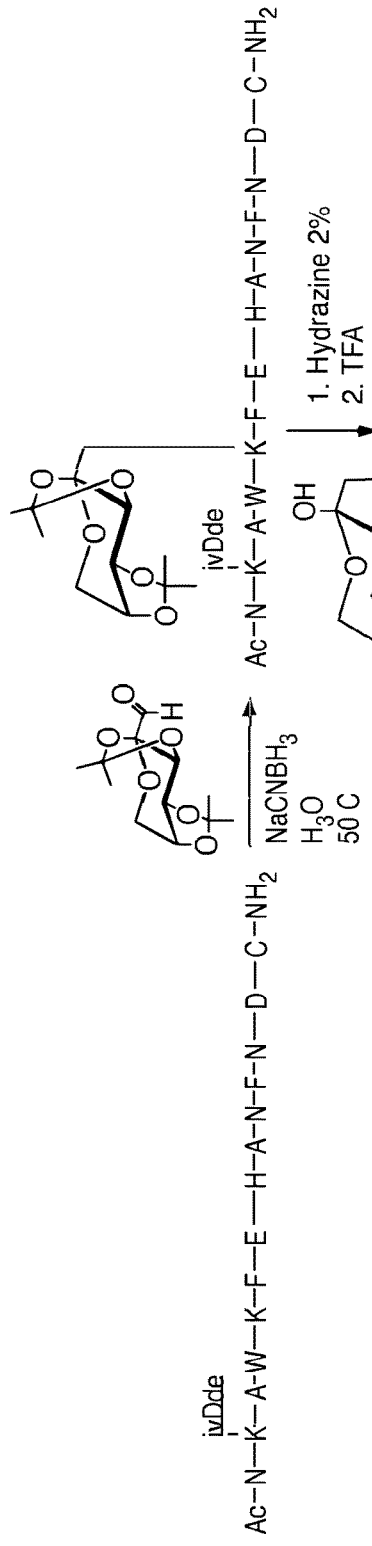
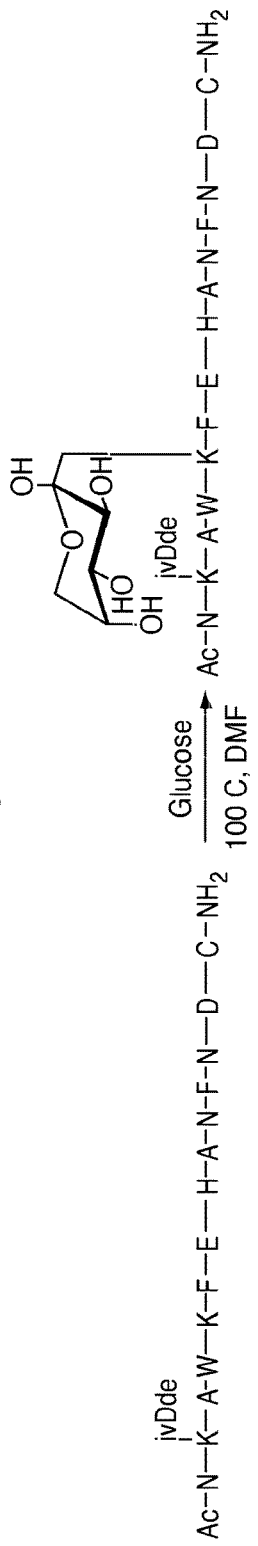
Fig. 4
Fig. 5
Fig. 6

60-5  60-4  60-3  60-1  56-10  56-4

Only  62-9  62-8  62-6  62-2  62-1
Sec.

Positive control

GLYCATED CD59 PEPTIDES, THEIR PREPARATION, AND USES THEREOF

RELATED APPLICATIONS

The present application is a Continuation of U.S. patent application U.S. Ser. No. 15/995,370, filed on Jun. 1, 2018, and issued on Nov. 2, 2021 as U.S. Pat. No. 11,161,910, which is a Division of U.S. patent application U.S. Ser. No. 14/724,911, filed on May 29, 2015, which is a Division of U.S. patent application U.S. Ser. No. 13/818,775, filed on May 6, 2013, and issued on Jun. 30, 2015 as U.S. Pat. No. 9,068,006, which is a 35 U.S.C. § 371 national stage application of International Application No. PCT/US2011/049118, filed on Aug. 25, 2011, which claims priority under 35 U.S.C. § 119(e) to U.S. provisional application, U.S. Ser. No. 61/377,060, filed Aug. 25, 2010, which is incorporated herein by reference.

SEQUENCE LISTING

The instant application contains a Sequence Listing which has been submitted electronically in ASCII format and is hereby incorporated by reference in its entirety. Said ASCII copy, created on Nov. 1, 2021, is named 00742-248005_Sequence_Listing_11.1.21_ST25 and is 14,830 bytes in size.

BACKGROUND OF THE INVENTION

Diabetes mellitus (diabetes) is a leading cause of morbidity and mortality in the adult population. This is primarily because diabetic patients tend to develop vascular complications that involve the kidneys (diabetic nephropathy), the retina (diabetic retinopathy), as well as large and small blood vessels in other organs (macro- and micro-vascular disease) including nerves (diabetic neuropathy). It is well established that the vascular complications of diabetes are caused by elevated blood glucose levels over long periods of time. Elevated blood glucose levels affect proteins by a nonenzymatic process known as glycation. Glycation, the non-enzymatic attachment of glucose to proteins, is considered a major post-translational modification causing tissue damage in diabetic subjects. Glycation involves the reaction of glucose and/or other reducing sugars with amino groups in proteins resulting in the formation of a Schiff's base or aldimine. This labile Schiff's base can cyclize to a more stable glycosylamine adduct. The function of the glycated protein may be impaired, depending on the location of the amino groups affected. Glycation of key regulatory proteins, such as those which prevent activation of the complement system, is believed to contribute to the manifestations of diabetes mellitus. Thus, compositions and methods which help measure the extent of protein glycation of key regulatory proteins of the complement system are considered valuable clinical tools to assess glycemic control over periods of different length and the efficacy of diabetes treatment.

SUMMARY OF THE INVENTION

The present invention originates from the recognition that lysine side chains of CD59, a regulatory membrane protein of the complement system, can be glycated and that these glycated lysine residues can also rearrange to Amadori products. As used herein, CD59 implies human CD59 (hCD59). The Amadori rearrangement occurs when the labile Schiff's base adduct tautomerizes to the corresponding enol form which further tautomerizes to linear and cyclic Amadori products as shown below. The present invention provides compositions and methods related to glycated Amadori products of CD59 and fragments thereof. The glycated Amadori product of CD59 may contribute to various complications of pre-diabetes and diabetes mellitus.

Normally, CD59 limits activation and restricts deposition of the membrane attack complex of complement (MAC) in blood vessels and the kidneys. Thus, glycation of CD59 disrupts its regulatory function and effectively enables the unregulated activation of complement and excessive and accelerated deposition of MAC. Reports of increased deposition of the membrane attack complex of complement (MAC) in blood vessels and kidneys of diabetic patients suggest that there may be a link between complement activation and the development of diabetic complications (Weiss, J. S., et al. (1990) *Cornea* 9, 131-138; Falk, R. J., et al. (1987) *Am. J. Kidney Dis.* 9, 121-128). Indeed, the MAC stimulates proliferation of fibroblasts and smooth muscle, mesangial, and other cells, in part by releasing growth factors such as basic fibroblast growth factor and platelet-derived growth factor from MAC-targeted endothelium (Benzaquen, L. R., et al. (1994) *J. Exp. Med.* 179, 985-992). The MAC also induces increased synthesis of extracellular matrix proteins by mesangial cells (Wagner, C., et al. (1994) *Exp. Nephrol.* 2, 51-56). Thus, glycation of CD59 may increase MAC deposition in diabetic tissues which may induce the release of growth factors that would stimulate cell proliferation in the vascular wall and contribute to the development of vascular proliferative disease. Glycated CD59 has been found in human urine, indicating that CD59 is glycated in vivo (Acosta et al. (2000) *PNAS* 97, 5450-5455).

Certain aspects of the invention relate to compositions and methods of preparing and using lysine-41-glycated Amadori products of CD59 and fragments thereof. According to the NMR structure of human CD59, lysine-41 (K41) appears particularly susceptible to glycation because of its proximity to the only histidine, histidine-44 (H44), in the protein (Fletcher, C. M., et al. (1994) *Structure* 2, 185-199) and forms a glycation motif. Furthermore, the fact that K41 is adjacent to tryptophan-40 (W40), a conserved amino acid that is essential for CD59 function, suggests that glycation of K41 may hinder the activity of CD59 (Bodian et al. (1997) *J. Exp. Med.* 185, 507-516; Yu, J., et al. (1997) *J. Exp. Med.* 185, 745-753). Replacement by site-directed mutagenesis of either K41 or H44 abolishes the sensitivity of human CD59 to glycation-mediated inactivation.

As indicated, the compositions and methods of the present invention are related to both the linear and cyclic forms of glycated Amadori products resulting from an Amadori rearrangement as shown below. Alternatively, compositions and methods regarding the glycated products of CD59 and peptide fragments thereof which do not arise from an Amadori rearrangement are disclosed in U.S. Pat. Nos. 6,835,545; 7,049,082; and 7,439,330; the entire contents of which are incorporated herein by reference. Examples of glycated products which do not arise from an Amadori rearrangement include the linear and reduced $N^\varepsilon$-(1-deoxy-D-glucitol-1-yl)L-lysine=glucitollysine moiety.

Formation of the glycated Amadori product of the lysine sidechain of CD59 follows the reversible condensation of a reducing sugar to the free amino group on the side chain of lysine to form a linear aldimine known as a Schiff's base. The Schiff's base rearranges to an enol tautomer, and the enol tautomer can subsequently rearrange to the linear (keto) and cyclic (1-deoxy-fructopyranose) forms of the Amadori product.

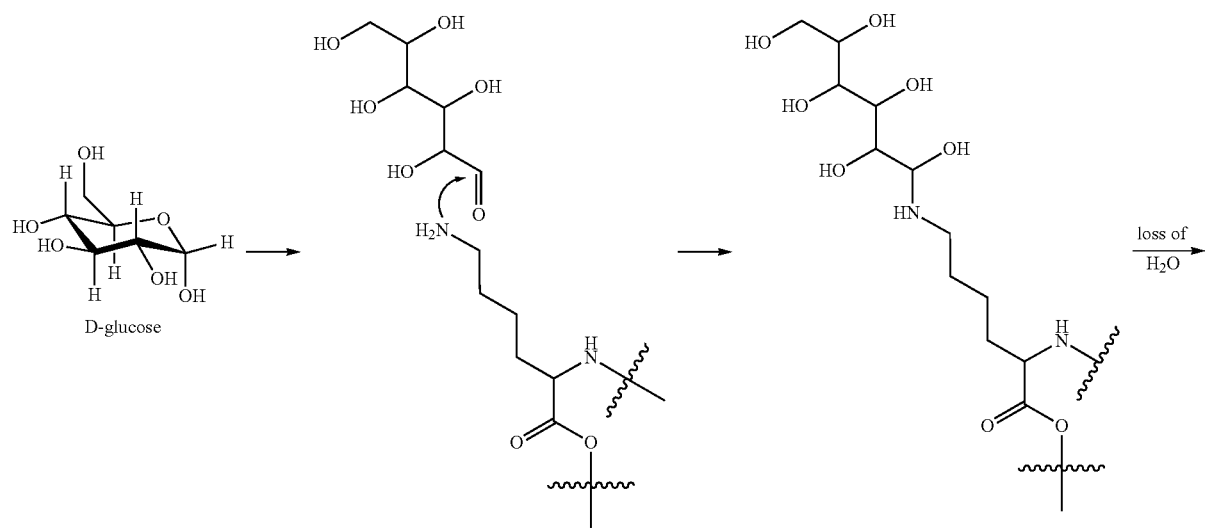
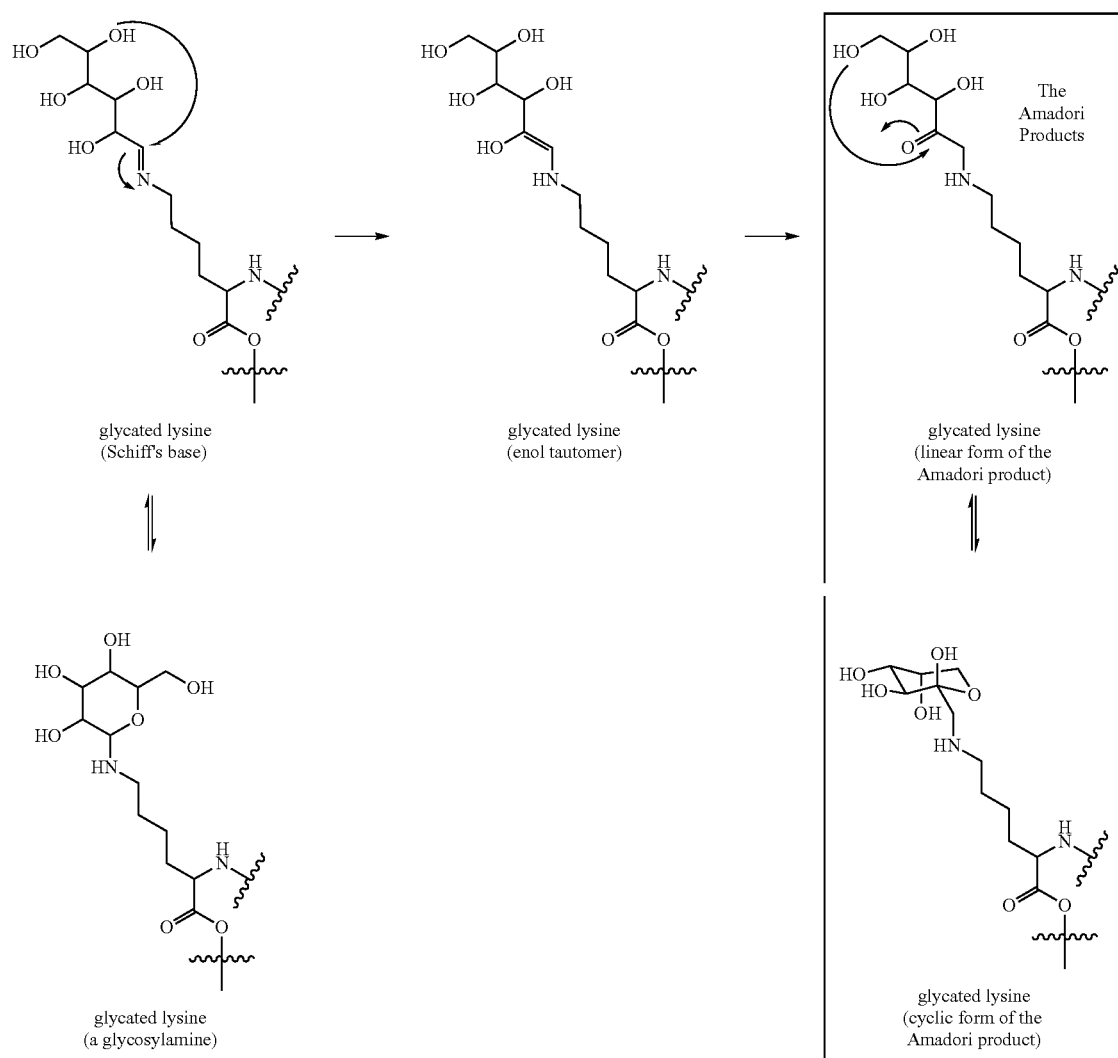

The present invention provides glycated Amadori products of the CD59 polypeptide and fragments thereof. In one aspect, the present invention provides glycated Amadori products of the full-length or mature CD59 polypeptide or protected forms thereof. In certain embodiments, the present invention provides glycated Amadori products of CD59 polypeptide fragments or protected forms thereof. In certain embodiments, the glycated Amadori products of CD59 polypeptide fragments or protected forms thereof has the amino acid sequence WKFEH set forth as SEQ ID NO:1. In certain embodiments, the present invention provides glycated Amadori products of CD59 polypeptide fragments or protected forms thereof. In certain embodiments, the glycated Amadori products of CD59 polypeptide fragments or protected forms thereof has the amino acid sequence NKAWKFEHANFNDC set forth in SEQ ID NO:3.

In certain embodiment, the present invention provides K41-glycated Amadori products of the full-length or mature CD59 polypeptide or protected forms thereof. In certain embodiments, the present invention provides K41-glycated Amadori products of CD59 polypeptide fragments or protected forms thereof.

In one aspect, the invention provides a peptide comprising a segment of CD59 of the formula:

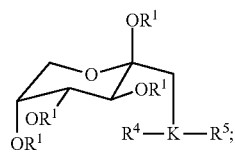

or a protected form thereof, wherein K is a CD59 lysine residue selected from the group consisting of K14, K30, K38, K65, K66, and K85; each $R^1$ is independently hydrogen or $Pg^1$ and wherein two $Pg^1$ groups may combine to form a heterocyclic ring; $R^4$ is absent, $Pg^2$, or a peptide sequence which is identical or homologous to a peptide sequence selected from residues 1-84 of CD59 set forth as SEQ ID NO:6; $R^5$ is absent, $Pg^3$, or a peptide sequence which is identical or homologous to a peptide sequence selected from residues 15-103 of mature CD59 set forth as SEQ ID NO:6; and each sidechain of each peptide sequence may comprise

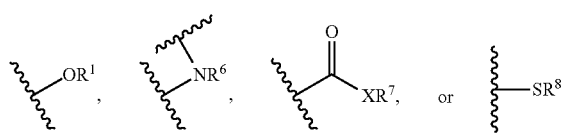

groups; wherein each $R^6$ is hydrogen or $Pg^2$; each X is O or NH; each $R^7$ is hydrogen; $Pg^2$, or $Pg^3$; each $R^8$ is hydrogen or $Pg^4$; each $Pg^1$ is an independently selected hydroxyl protecting group; each $Pg^2$ is an independently selected amino protecting group; each $Pg^3$ is an independently selected carboxyl protecting group; and each $Pg^4$ is an independently selected thiol protecting group.

In another aspect, the invention provides a peptide comprising a segment of CD59 of the formula:

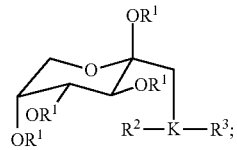

or a protected form thereof, wherein K is the CD59 lysine residue K41; $R^2$ is absent, $Pg^2$, or a peptide sequence which is identical or homologous to a peptide sequence selected from residues 1-40 of CD59 set forth as SEQ ID NO:6; $R^3$ is absent, $Pg^3$, or a peptide sequence which is identical or homologous to a peptide sequence selected from residues 42-103 of CD59 set forth as SEQ ID NO:6; and each sidechain of each peptide sequence may comprise

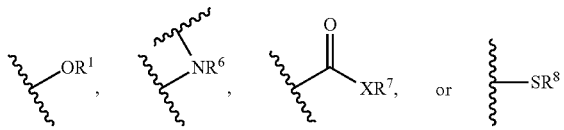

groups; wherein each $R^6$ is hydrogen or $Pg^2$; each X is O or NH; each $R^7$ is hydrogen; $Pg^2$, or $Pg^3$; each $R^8$ is hydrogen or $Pg^4$; each $Pg^1$ is an independently selected hydroxyl protecting group; each $Pg^2$ is an independently selected amino protecting group; each $Pg^3$ is an independently selected carboxyl protecting group; and each $Pg^4$ is an independently selected thiol protecting group.

In yet another aspect, the invention provides an immunogenic glycated Amadori product of the CD59 polypeptide and fragments thereof which can be used as antigens to generate antibodies which specifically bind glycated Amadori products of the CD59 polypeptide. In certain embodiments, the immunogenic glycated Amadori products are K41-glycated Amadori products of the CD59 polypeptide.

In another aspect, the invention provides isolated human CD59 with glycated K41 of the formula:

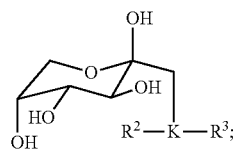

wherein $R^2$ is a peptide sequence which is identical or homologous to a peptide sequence selected from residues 1-40 of CD59 set forth as SEQ ID NO:6; and $R^3$ is a peptide sequence which is identical or homologous to a peptide sequence selected from residues 42-103 of CD59 set forth as SEQ ID NO:6.

In certain aspects, the invention provides methods for preparing glycated Amadori products of the CD59 polypeptide and CD59 fragments of the present application. The preparation and purification of glycated Amadori products of the CD59 polypeptide and fragments thereof posed a significant challenge at the time of this invention. In one embodiment, the present invention provides methods for preparing glycated Amadori products of the full-length or mature CD59 polypeptide or protected forms thereof. In certain embodiments, the present invention provides methods for preparing glycated Amadori products of truncated CD59 polypeptide or protected forms thereof. In one embodiment, the present invention provides methods for preparing K41-glycated Amadori products of the full-length or mature CD59 polypeptide or protected forms thereof. In certain embodiments, the present invention provides methods for preparing K41-glycated Amadori products of fragments of the CD59 polypeptide or protected forms thereof. In certain embodiments, the invention provides a method of solid phase synthesis of a peptide of the sequence,

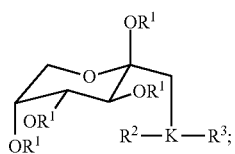

or a protected form thereof, comprising incorporating a lysine derivative of the formula:

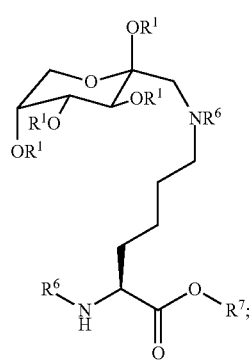

wherein each $R^1$ is independently hydrogen or $Pg^1$ and wherein two $Pg^1$ groups may combine to form a heterocyclic ring; $R^2$ is absent, $Pg^2$, or a peptide sequence which is identical or homologous to a peptide sequence selected from residues 1-40 of CD59 set forth as SEQ ID NO:6; $R^3$ is absent, $Pg^3$, or a peptide sequence which is identical or homologous to a peptide sequence selected from residues 42-103 of CD59 set forth as SEQ ID NO:6; and each sidechain of each peptide sequence may comprise

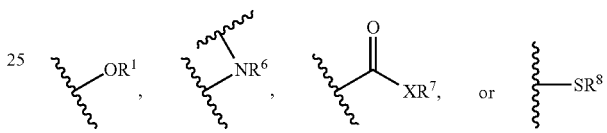

groups; wherein each $R^6$ is hydrogen or $Pg^2$; each X is O or NH; each $R^7$ is hydrogen; $Pg^2$, or $Pg^3$; each $R^8$ is hydrogen or $Pg^4$; each $Pg^1$ is an independently selected hydroxyl protecting group; each $Pg^2$ is an independently selected amino protecting group; each $Pg^3$ is an independently selected carboxyl protecting group; and each $Pg^4$ is an independently selected thiol protecting group.

In certain embodiments, the invention provides a method of preparing a peptide of the sequence,

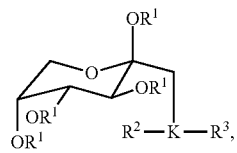

or a protected form thereof, by: providing a peptide of the sequence, $R^2$—K—$R^3$, or a protected form thereof, and glycating K41 of the peptide with D-glucose; wherein each $R^1$ is independently hydrogen or $Pg^1$ and wherein two $Pg^1$ groups may combine to form a heterocyclic ring; $R^2$ is absent, $Pg^2$, or a peptide sequence which is identical or homologous to a peptide sequence selected from residues 1-40 of CD59 set forth as SEQ ID NO:6; $R^3$ is absent, $Pg^3$, or a peptide sequence which is identical or homologous to a peptide sequence selected from residues 42-103 of CD59 set forth as SEQ ID NO:6; and each sidechain of each peptide sequence may comprise

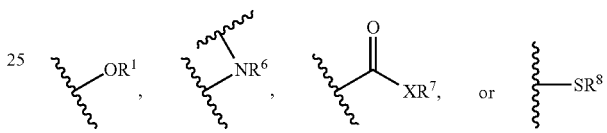

groups; wherein each $R^6$ is hydrogen or $Pg^2$; each X is O or NH; each $R^7$ is hydrogen; $Pg^2$, or $Pg^3$; each $R^8$ is hydrogen or $Pg^4$; each $Pg^1$ is an independently selected hydroxyl protecting group; each $Pg^2$ is an independently selected amino protecting group; each $Pg^3$ is an independently selected carboxyl protecting group; and each $Pg^4$ is an independently selected thiol protecting group.

In certain embodiments, the invention provides a method of preparing a peptide of the sequence,

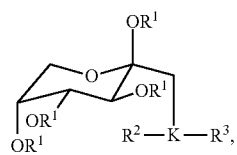

or a protected form thereof, by: providing a peptide of the sequence, $R^2$—K—$R^3$, or a protected form thereof, reacting the peptide with an aldehyde of formula:

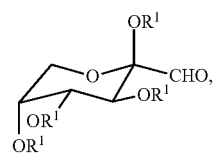

or a protected form thereof, under suitable conditions to form with the peptide a Schiff's base of the formula:

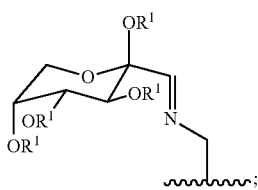

and reducing the Schiff's base to an amine of the formula:

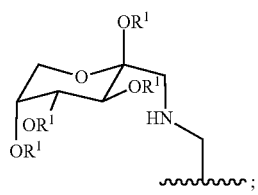

wherein each $R^1$ is independently hydrogen or $Pg^1$ and wherein two $Pg^1$ groups may combine to form a heterocyclic ring; $R^2$ is absent, $Pg^2$, or a peptide sequence which is identical or homologous to a peptide sequence selected from residues 1-40 of CD59 set forth as SEQ ID NO:6; $R^3$ is absent, $Pg^3$, or a peptide sequence which is identical or homologous to a peptide sequence selected from residues 42-103 of CD59 set forth as SEQ ID NO:6; and wherein each sidechain of each peptide sequence may comprise

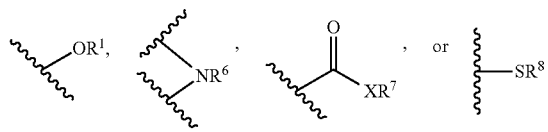

groups; wherein each $R^6$ is hydrogen or $Pg^2$; each X is O or NH; each $R^7$ is hydrogen; $Pg^2$, or $Pg^3$; each $R^8$ is hydrogen or $Pg^4$; each $Pg^1$ is an independently selected hydroxyl protecting group; each $Pg^2$ is an independently selected amino protecting group; each $Pg^3$ is an independently selected carboxyl protecting group; and each $Pg^4$ is an independently selected thiol protecting group.

According to one aspect of the invention, isolated antibodies or fragments thereof are provided. Previous efforts to generate such antibodies were hampered by the inability to prepare and purify glycated Amadori products of CD59 polypeptide and fragments thereof. These antibodies, fragments thereof, and the nucleic acid sequences encoding such antibodies are useful for the diagnosis and monitoring of prediabetic, diabetic and related conditions. Thus, the present invention provides clinically relevant, antibody-based diagnostic compositions and methods that take advantage of the glycated Amadori products of the CD59 polypeptide and fragments thereof.

In another aspect, the invention provides an isolated antibody or antibody fragment, which specifically binds the epitope comprising the glycated Amadori product of a lysine of a peptide as described herein. In certain embodiments, the Amadori product of a glycated lysine is glycated at K41 of CD59. In certain embodiments, the epitope provides K41-glycated WKFEH set forth in SEQ ID NO: 1. In certain embodiments, the antibody or fragment thereof binds to a conformational epitope. In certain embodiments, the antibody distinguishes between glycated Amadori products of CD59 and non-glycated products of CD59. In certain embodiments, the antibody distinguishes between glycated Amadori products of CD59 and glycated non-Amadori products of CD59.

In another aspect, the invention provides a nucleic acid sequence that encodes the antibody or antibody fragment of the invention. In certain aspects, the invention provides a hybridoma that comprises a nucleic acid that encodes an antibody of the invention. In one aspect, the invention provides a hybridoma cell line that produces the antibody or antibody fragment of the invention. In another aspect, the invention provides an expression vector comprising an isolated nucleic acid molecule encoding the antibody or antibody fragment of the invention. In yet another aspect, the invention provides a host cell transformed by or transfected with the expression vector of the invention. In certain aspects, the invention provides a plasmid which produces the antibody or antibody fragment of the invention.

In another aspect, the invention provides a method of making an antibody that specifically binds to the glycated Amadori product of CD59 but not to non-glycated CD59: preparing an immunogenic polypeptide of the invention, and immunizing an animal with the immunogenic polypeptide. In certain embodiments, the invention provides the method comprising: removing a lymph node from the immunized animal, harvesting cells from the removed lymph node, fusing the harvested cells with mouse myeloma cells to make hybridomas, expanding the hybridomas, identifying a hybridoma that produces an antibody that specifically binds to the immunogenic polypeptide, or the antigenic motif of the immunogenic polypeptide, and collecting the antibody produced by the hybridoma. In further embodiments, the invention provides the method wherein the immunogenic glycated Amadori peptide has the amino acid sequence NKAWKFEHANFNDC set forth in SEQ ID NO:3. In certain embodiments, the invention provides the method wherein the immunogenic glycated Amadori peptide has the amino acid sequence WKFEH set forth in SEQ ID NO:1.

Some features of the invention extend to the hybridoma, which provides an indefinitely prolonged (non-exhaustible) source of the aforementioned monoclonal antibodies. In certain embodiments, the invention provides a hybridoma that comprises a nucleic acid that encodes an antibody that distinguishes between glycated Amadori products of CD59, or fragments thereof, and non-glycated products of CD59, or fragments thereof. In certain embodiments, the invention provides a hybridoma that comprises a nucleic acid that encodes an antibody that distinguishes between glycated Amadori product of CD59, or fragments thereof, and glycated non-Amadori products of CD59, or fragments thereof.

The invention also provides methods related to the use of an antibody which specifically binds to glycated Amadori products of the CD59 polypeptide for detecting and measuring levels of glycated Amadori products of the CD59 polypeptide. The discovery of an antibody that specifically binds to glycated Amadori products of the CD59 polypeptide facilitates analysis of diseases in which the amount of such glycated Amadori products differ from normal levels. For example, it has been discovered that the level of glycation of CD59 is elevated in pre-diabetes and diabetes. Thus, onset, progression, and/or regression of pre-diabetes and diabetes or other diseases can be monitored by monitoring levels of glycated Amadori products of the CD59 polypeptide in a subject. It also has been found that CD59 is present in urine, saliva, and tissue. Therefore, the measurement of glycated Amadori products of the CD59 polypeptide can be done in urine or other samples without requiring a blood sample.

In yet another aspect, the invention provides a method for diagnosing or monitoring the progression of a diabetic condition by: obtaining a sample from a human subject; contacting the sample with an antibody or antibody fragment as described herein: and determining the amount of glycated Amadori product of CD59 present in the sample. In certain embodiments, the steps of obtaining, contacting, and determining are repeated on one or more occasions. In further embodiments, the invention provides methods wherein the contacting is performed in a reaction chamber and wherein the antibody, antibody fragment, glycated Amadori product of CD59, or glycated Amadori product of a fragment of CD59 is immobilized on a solid support. In certain embodiments, the invention provides the method wherein the antibody or antibody fragment is labeled. In further embodiments, the invention provides the method performed in conjunction with a therapeutic treatment regime comprising an anti-diabetic agent. In certain embodiments, the invention provides the method wherein the anti-diabetic agent is selected from the group consisting of insulin, an insulin analog, nateglinide, repaglinide, metformin, thiazolinediones, glitazones such as troglitazone, pioglitazone and rosiglitazone, glisoxepid, glyburide, glibenclamide, acetohexamide, chloropropamide, glibornuride, tolbutamide, tolazamide, glipizide, carbutamide, gliquidone, glyhexamide, phenbutamide, tolcyclamide, glimepiride and gliclazide.

In certain aspects, the invention provides a kit to determine the amount of glycated Amadori product of CD59 present in a sample comprising an antibody or antibody fragment as described herein and instructions for use. In another aspect, the invention provides a kit for detecting the presence of the glycated Amadori product of CD59 comprising a package including a container containing an isolated antibody or antibody fragment as described herein, and instructions for use of the antibody or antibody fragment to detect the presence of the glycated Amadori product of CD59.

In one aspect, the invention provides a kit comprising a package including a container containing a hybridoma that comprises a nucleic acid sequence that encodes an antibody or antibody fragment as described herein, and instructions for producing the antibody. These and other aspects of the invention will be described in further detail in connection with the detailed description of the invention.

Definitions

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The "enantiomeric excess" of a substance is a measure of how pure a desired enantiomer is relative to the undesired enantiomer. Enantiomeric excess is defined as the absolute difference between the mole fraction of each enantiomer which is most often expressed as a percent enantiomeric excess. For mixtures of diastereomers, there are analogous definitions and uses for "diastereomeric excess" and percent diastereomeric excess. For example, a sample with 70% of R isomer and 30% of S will have an enantiomeric excess of 40%. This can also be thought of as a mixture of 40% pure R with 60% of a racemic mixture (which contributes 30% R and 30% S to the overall composition).

The terms "protecting group" and "protected form" each refer to an "amino-protecting group" if attached to a nitrogen atom, an "hydroxyl protecting group" if attached to an oxygen atom of an alcohol group, a "carboxylic acid protecting group" if attached to an oxygen atom of a carboxylate group, or a "thiol protecting group" if attached to a sulfur atom. Each of these protecting groups is described in more detail below.

A "hydroxyl protecting group" or "Pg$^1$", as used herein, is well known in the art and include those described in detail in *Protective Groups in Organic Synthesis*, Fourth Ed. Greene, T. W. and Wuts, P. G., Eds., John Wiley & Sons, New York: 2007, the entire contents of which are hereby incorporated by reference. Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, p-methoxybenzyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

An "amino-protecting group," or "$Pg^2$", as used herein, is well known in the art and include those described in detail in Greene (2007). Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

A "carboxylic acid protecting group," or "protected carboxylic acid," or "$Pg^3$", as used herein, are well known in the art and include those described in detail in Greene (2007). Examples of suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, tri- tyl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

A "thiol protecting group" or "$Pg^4$", as used herein, is well known in the art and include those described in detail in Greene (2007). Suitable thiol protecting groups include methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis (4',4''-dimethoxyphenyl)methyl, 1,1-bis(4-methoxyphenyl)-1'-pyrenylmethyl, 9-anthryl, 9-(9-phenyl)xanthenyl, 9(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TB MPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in Greene (2007).

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment of diseases or disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "independently selected" is used herein to indicate that the R groups can be identical or different.

As used herein, the term "labeled" is intended to mean that a compound has at least one element, isotope, or chemical compound attached to enable the detection of the compound. In general, labels typically fall into three classes: a) isotopic labels, which may be radioactive or heavy isotopes, including, but not limited to, $^2$H, $^3$H, $^{32}$P, $^{35}$S, $^{67}$Ga, $^{99m}$Tc (Tc-99m), $^{111}$In, $^{123}$I, $^{125}$I, $^{169}$Yb and $^{186}$Re; b) immune labels, which may be antibodies or antigens, which may be bound to enzymes (such as horseradish peroxidase) that produce detectable agents; and c) colored, luminescent, phosphorescent, or fluorescent dyes. It will be appreciated that the labels may be incorporated into the compound at any position that does not interfere with the biological activity or characteristic of the compound that is being detected.

"Polypeptide," "peptide," or "protein": According to the present invention, a "polypeptide," "peptide," "protein" comprises a string of at least three amino acids linked together by peptide bonds. The terms "protein," "peptide," or "polypeptide" may be used interchangeably. Peptide may refer to an individual peptide or a collection of polypeptides. Inventive peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In certain embodiments, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

"Polynucleotide" or "oligonucleotide": Polynucleotide or oligonucleotide refers to a polymer of nucleotides. Typically, a polynucleotide comprises at least three nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

BRIEF DESCRIPTION OF THE DRAWINGS

FIG. 2 discloses SEQ ID NOS 10, 10 and 3, respectively, in order of appearance.

FIG. 3 discloses SEQ ID NO: 3.

FIG. 4 depicts the resin-based direct glycation synthetic strategy. FIG. 4 discloses SEQ ID NOS 10, 10 and 3, respectively, in order of appearance.

FIG. 5 depicts the solution-phase reductive amination synthetic strategy. FIG. 5 discloses SEQ ID NOS 10, 3 and 3, respectively, in order of appearance.

FIG. 6 depicts the solution-phase direct glycation synthetic strategy. FIG. 6 discloses SEQ ID NOS 10 and 3, respectively, in order of appearance.

DETAILED DESCRIPTION OF CERTAIN EMBODIMENTS OF THE INVENTION

Figure 1:
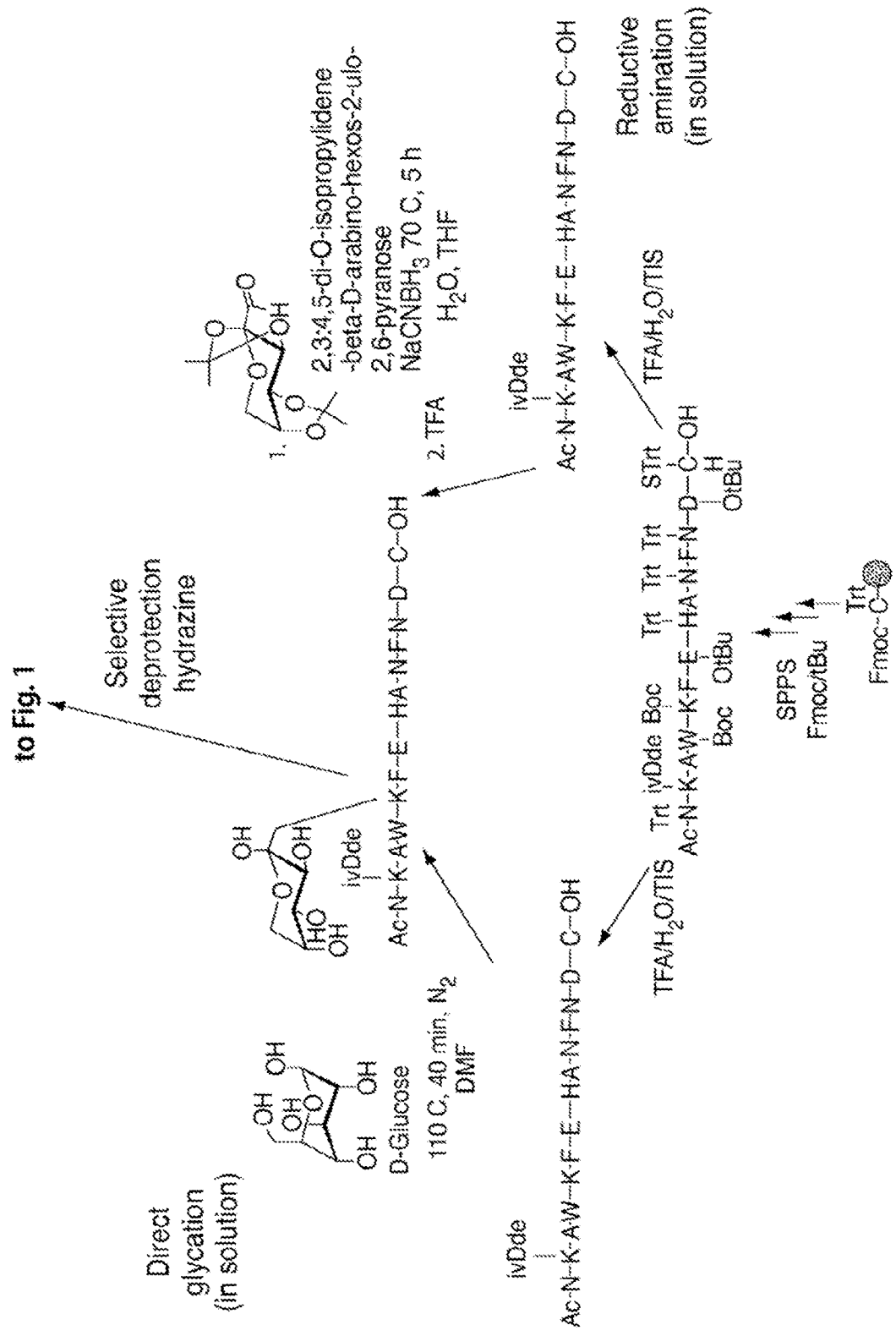
FIG. 1 depicts synthetic strategies for preparation of K41-glycated Amadori products of residues 37-50 of the CD59 polypeptide set forth in SEQ ID NO:6. On page 1 of FIG. 1, SEQ ID NOS 10, 10, 3, 3 and 3 are disclosed, respectively, in order of appearance. On page 2 of FIG. 1, SEQ ID NOS 3, 10, 10 and 10 are disclosed, respectively, in order of appearance.
Figure 1:
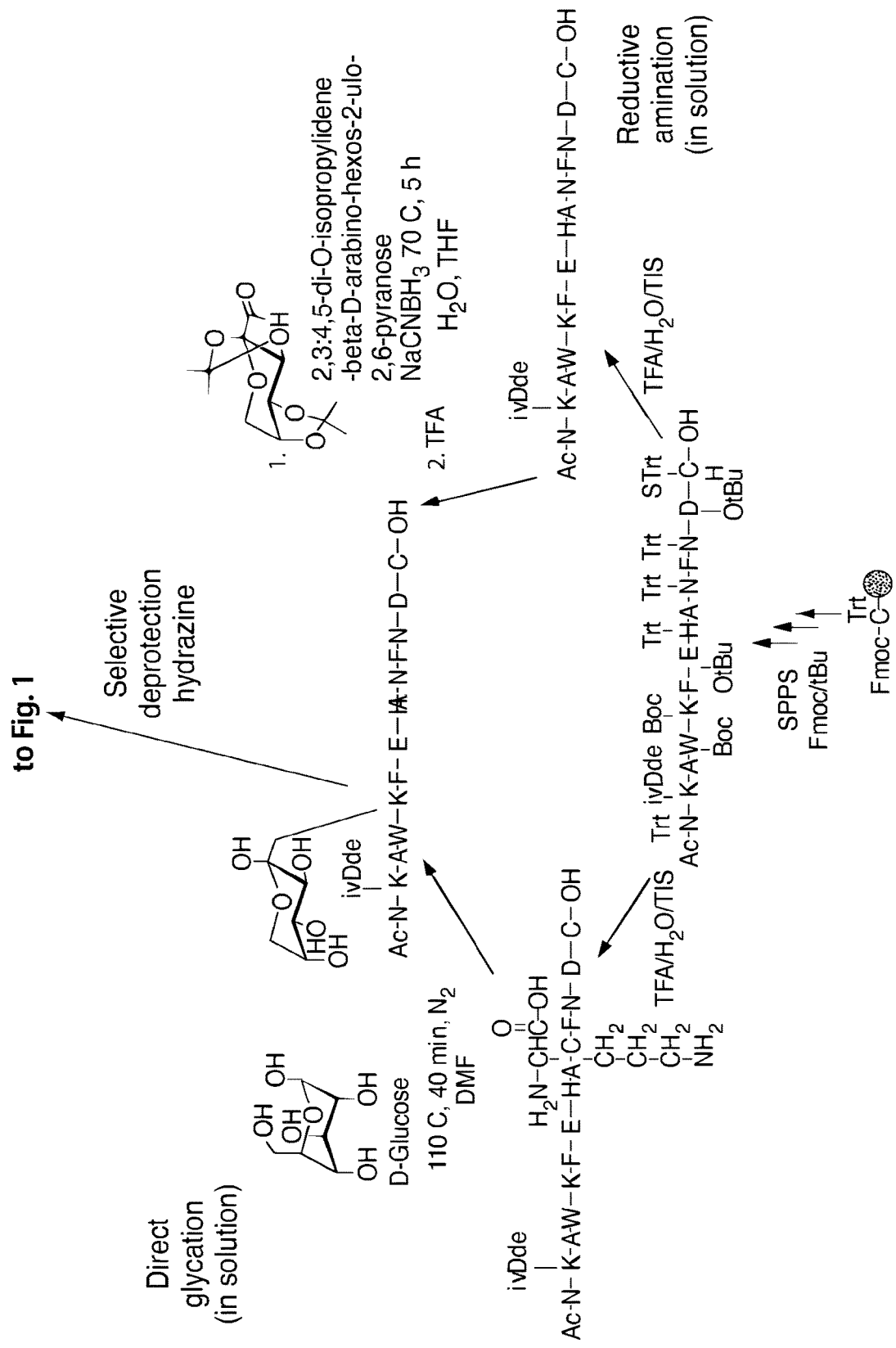
Figure 2:
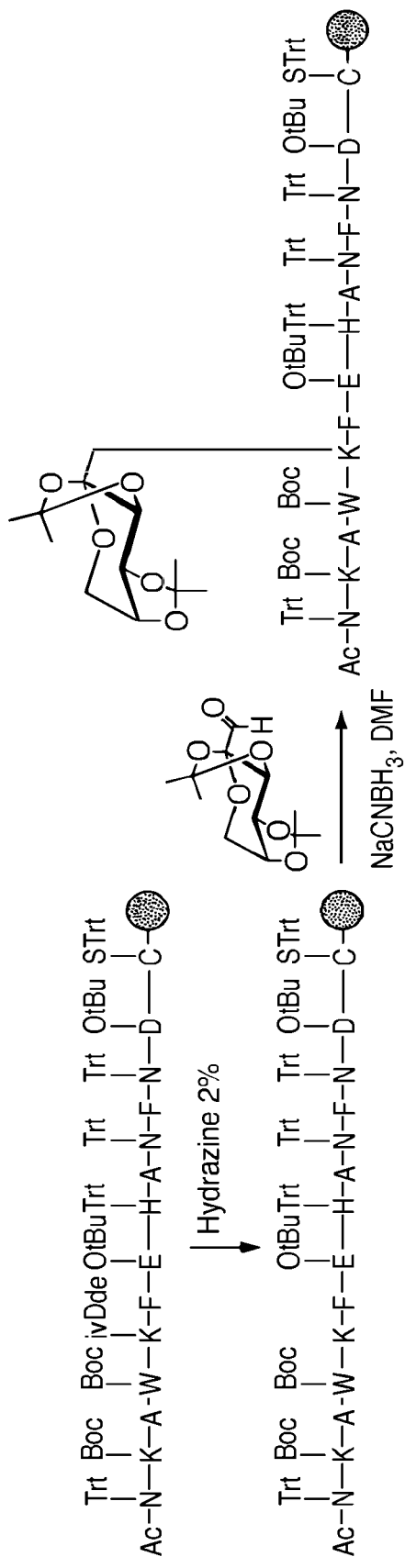
FIG. 2 depicts the resin-based reductive amination synthetic strategy.
Figure 3:
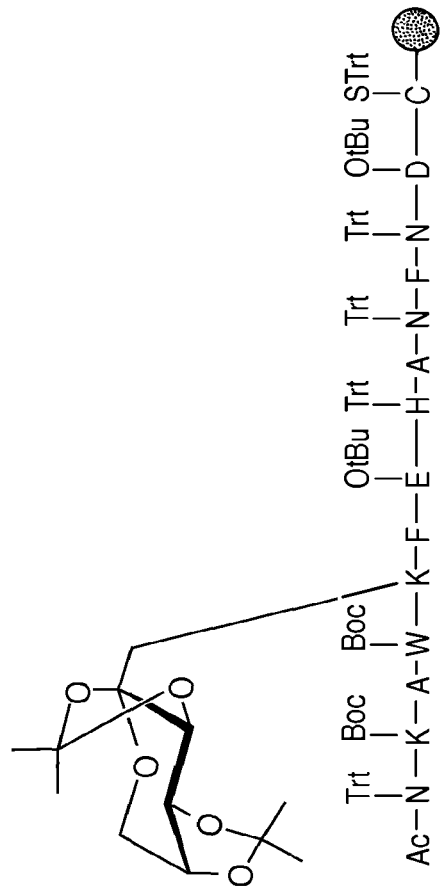
FIG. 3 depicts the stepwise solid-phase synthetic strategy.
Figure 7:
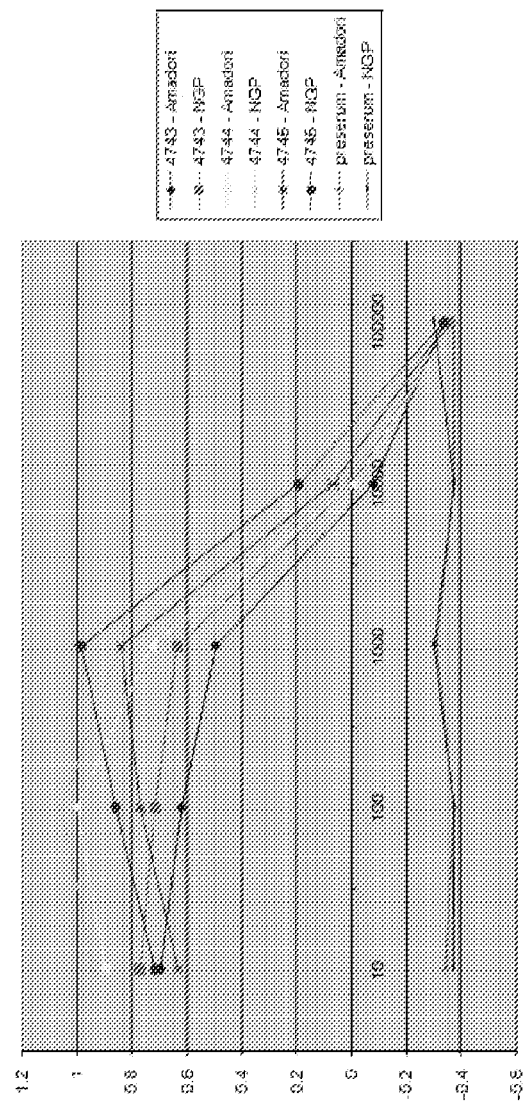
FIG. 7 depicts the results of an ELISA assay for K41-glycated Amadori CD59 polypeptide and non-glycated CD59 polypeptide. The data do not indicate selective binding of glycated relative to non-glycated polypeptide. The antibodies collected just after fusion are presumed to be polyclonal.
Figure 8:
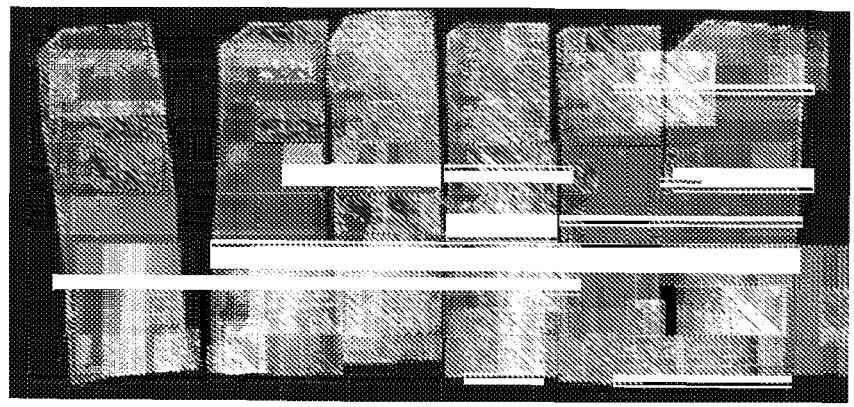
FIGS. 8 and 9 depict Western blot analyses following the treatment of 10 μg CD59 with beta-mercaptoethanol. Prominent signals were detected on plates corresponding to antibodies 56-10, 60-3 and 62-6.
Figure 9:
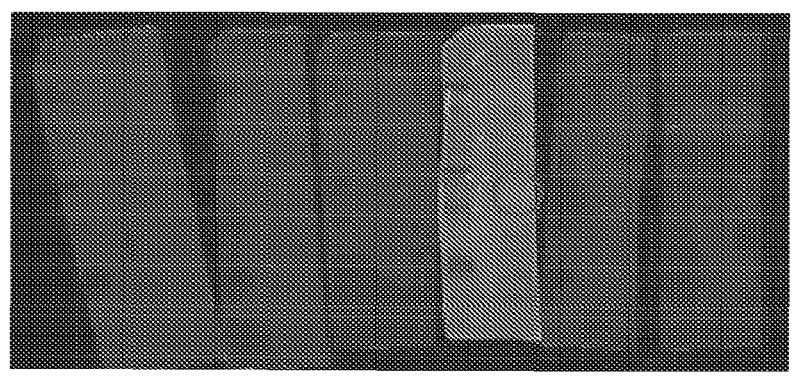
Figure 10:
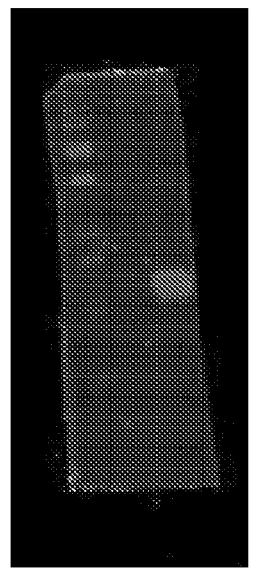
FIG. 10 depicts one of the Western blots which was reprobed and detected with antibody N-20, which only binds to beta-mercaptoethanol-treated CD59. This experiment verified that the positive signals in the previous slides detected binding of antibodies to beta-mercaptoethanol-treated CD59.
Figure 11:
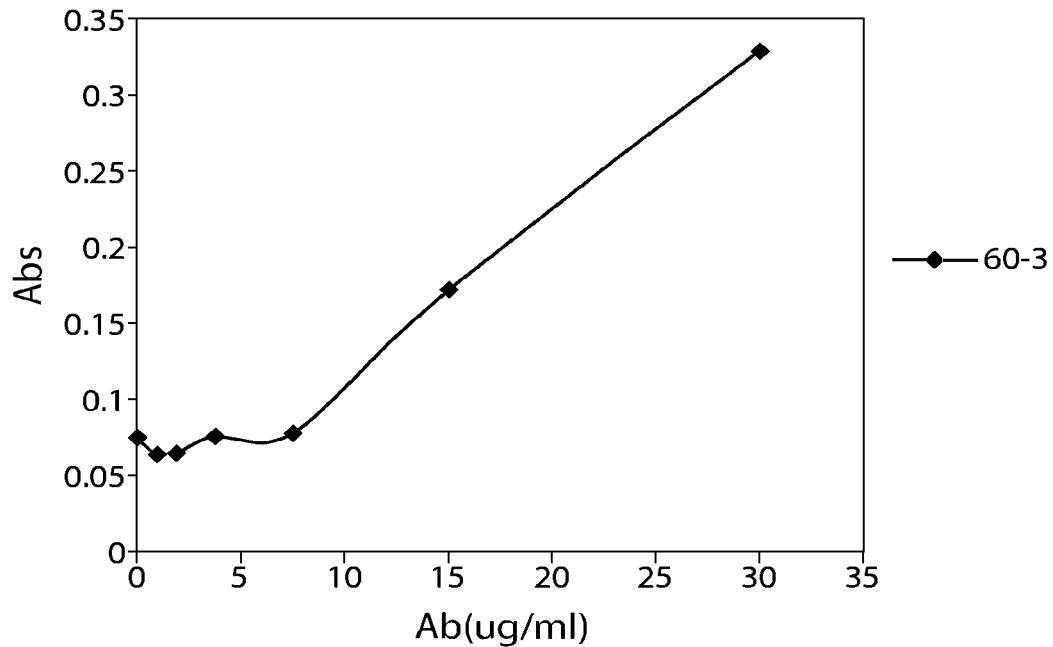
FIG. 11 depicts the results of an ELISA assay to detect the binding of purified antibody 60-3 with purified beta-mercaptoethanol-treated CD59 at a fixed concentration of 8 μg/ml. Importantly, binding of Amadori antibody with CD59 could only be detected upon exposure of CD59 to beta-mercaptoethanol.

Glycated Amadori Products of the CD59 Polypeptide and Fragments Thereof

The present invention provides glycated Amadori products of the CD59 polypeptide and fragments thereof. The present invention further provides antibodies or antigen-binding fragments thereof which bind specifically to glycated Amadori products of the CD59 polypeptide, compositions containing one or a combination of such antibodies or fragments thereof, hybridoma cell lines that produce the antibodies, and methods of making and using the antibodies or antigen-binding fragments thereof for diagnosis and treatment of diabetic conditions and diabetes-related conditions. In contrast to glycated biomarkers such as hemoglobin, which is a bystander, glycation of CD59 is believed to be involved in the pathogenesis of the vascular complications of pre-diabetes and diabetes. Accordingly, clinical evaluation of glycated Amadori product of CD59 is a more direct measure for vascular complications of pre-diabetes and diabetes associated with glycation inactivation of CD59.

As used herein, CD59 (also known as membrane inhibitor of reactive lysis [MIRL], protectin, HRF20 and H19), glycated CD59, and glycated Amadori products of CD59 are polypeptides having essentially the amino acid sequence identity of Accession No. M95708 (Davies, A., et al., *Journal J. Exp. Med.* 170 (3), 637-654 (1989)). A nucleic acid sequence encoding CD59 also is provided by Davis, A, et al. A full length non-glycated CD59 sequence of 128 amino acid residues is provided herein as SEQ ID NO:5. The sequence of non-glycated of CD59 of 103 amino acid residues that is present in mature form in cells and tissues is set forth as SEQ ID NO:6. The sequence of mature CD59 of 103 amino acid residues that is glycated at K41 is set forth as SEQ ID NO:7. The sequence of mature CD59 that is glycated at K14, K30, K38, K41, K65, K66, and K85 is set forth as SEQ ID NO:8.

As used herein, the term "glycated CD59" means that the glycating sugar is bound to CD59 in either a linear or cyclic form.

As used herein, the term "glycated Amadori product(s) of CD59" polypeptide includes mature CD59 polypeptide with one or more glycated lysine (K) residues which have undergone Amadori rearrangement. In certain embodiments, the glycated Amadori lysine residue of CD59 is residue K41 of mature CD59. One of ordinary skill in the art will understand that a fragment of CD59 can be compared to mature or full-length CD59, and the presence of a residue in that fragment is said to "correspond" to the residue of mature or full-length CD59. As used herein therefore, residue positions for lysines are identified as they occur in mature or full-length CD59, whether that residue is part of mature CD59 or part of a fragment or modified fragment thereof. Thus, K41 maintains that designation in mature CD59 or fragments thereof.

As used herein, the "glycated Amadori products of CD59" include linear and cyclic forms, as shown below, which arose from the Amadori rearrangement, as described herein, of a glycating sugar bound to CD59.

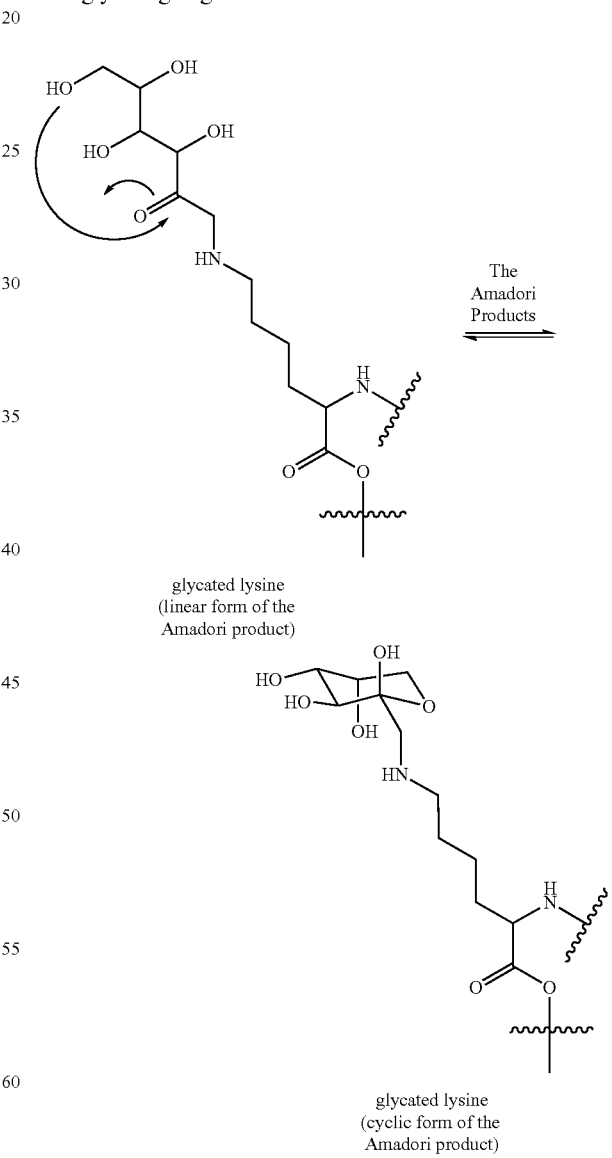

glycated lysine
(linear form of the Amadori product)

The Amadori Products glycated lysine
(cyclic form of the Amadori product)

As used herein, the term "glycating sugar" includes aldohexoses (e.g., glucose, mannose, allose, altrose, gulose, idose, galactose, and talose) and ketohexoses (e.g., fructose, sorbose, tagatose, and psocose). In certain embodiments, the glycating sugar is glucose. In other embodiments, the glycating sugar is fructose.

In certain embodiments, a lysine residue of CD59 or a fragment thereof may be glycated by contacting reacting with CD59 or a fragment thereof with glycating sugars. The residue in position 41 of mature CD59 is a lysine, and the residue that corresponds to this position in fragments is referred to herein as "K41". CD59 in which the K41 residue is glycated is referred to herein as K41-glycated CD59.

It is known that the CD59 polypeptide sequence includes a 25 amino acid signal peptide that is cleaved when CD59 is produced, thus forming the mature CD59 protein sequence. As would be understood by one of ordinary skill in the art, CD59 in a sample obtained from a subject would typically be CD59 from which the signal peptide has been cleaved. The sequence of the CD59 polypeptide prior to removal of the signal peptide is provided herein as SEQ ID NO:5 and the amino acid sequence of mature CD59 polypeptide is set forth herein as SEQ ID NO:6.

We have determined, surprisingly, that glycation of CD59, including, but not limited to K41 glycation of CD59, is correlated to abnormal blood sugar levels and that glycation of CD59 interferes with the normal activity of CD59. CD59 functions normally by binding to the terminal components of the membrane attack complex of complement (MAC), thereby interfering with membrane insertion and polymerization of the C9 component of complement. Glycation at the K41 of CD59 interferes with CD59's ability to prevent the assembly of the MAC. While not wishing to be bound by any theory, it is believed that, as a result of glycation of CD59, the MAC is permitted to form and leads to the development of proliferative chronic diabetic complications. Indeed, the present inventor has shown that the membrane attack complex stimulates proliferation of fibroblasts, smooth muscle, mesangial and other cells, in part by releasing growth factors such as FGF and PDGF from MAC-targeted endothelium. The MAC also induces increased synthesis of extracellular matrix proteins by mesangial cells. Thus, increased MAC deposition in diabetic tissues is believed to induce growth factor release from endothelium, which stimulates cell proliferation in the vascular wall and contributes to the expansion of the extracellular matrix and to the glomerulosclerosis that characterizes diabetic nephropathy.

The invention includes, in one aspect, methods and compositions for the preparation of antibodies that specifically bind to the glycated Amadori product of CD59. Compositions useful for making an antibody of the invention include a glycated Amadori product of CD59 polypeptide molecule. As used herein, a glycated Amadori product of CD59 polypeptide or fragment thereof means a glycated Amadori product of the full-length or mature CD59 polypeptide, or a glycated Amadori product of a fragment of the CD59 polypeptide. One such glycated Amadori product of CD59 polypeptide that is useful in the methods of the invention is the polypeptide set forth as NH$_2$-NKAWKFEHANFNDC (SEQ ID NO:3). In SEQ ID NO:3, the lysine (K) that is residue 5 of SEQ ID NO:3 corresponds to the lysine that is residue 41 (K41) of the mature CD59 polypeptide sequence, and in SEQ ID NO:3, the K5 residue is glycated.

The invention also involves fragments of the foregoing proteins and protected forms thereof. A fragment of K41-glycated Amadori product of CD59 comprises at least 8, 9, 10, 11, 12, 13, 14, 15, 16, 17, 18, 19, or 20 or more contiguous amino acids of CD59 having a consecutive sequence found in CD59 or a modified CD59 sequence as described herein. In certain embodiments, a fragment includes K41, which may or may not be glycated K41. Fragments of glycated Amadori product of CD59 can be used for a variety of purposes, including in the preparation of molecules that bind specifically to glycated Amadori product of CD59 and in immunoassays well known to those of ordinary skill in the art, including competitive binding immunoassays.

In one aspect, the invention provides a peptide comprising a segment of CD59 of the formula:

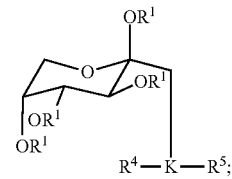

or a protected form thereof, wherein K is a CD59 lysine residue selected from the group consisting of K14, K30, K38, K65, K66, and K85; each R$^1$ is independently hydrogen or Pg$^1$ and wherein two Pg$^1$ groups may combine to form a heterocyclic ring; R$^4$ is absent, Pg$^2$, or a peptide sequence which is identical or homologous to a peptide sequence selected from residues 1-103 of CD59 set forth as SEQ ID NO:6; R$^5$ is absent, Pg$^3$, or a peptide sequence which is identical or homologous to a peptide sequence selected from residues 1-103 of mature CD59 set forth as SEQ ID NO:6; and each sidechain of each peptide sequence may comprise

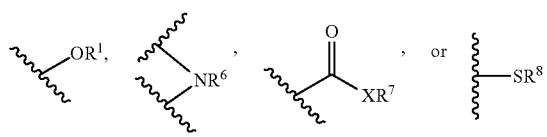

groups; wherein each R$^6$ is hydrogen or Pg$^2$; each X is O or NH; each R$^7$ is hydrogen; Pg$^2$, or Pg$^3$; each R$^8$ is hydrogen or Pg$^4$; each Pg$^1$ is an independently selected hydroxyl protecting group; each Pg$^2$ is an independently selected amino protecting group; each Pg$^3$ is an independently selected carboxyl protecting group; and each Pg$^4$ is an independently selected thiol protecting group.

In certain embodiments, the invention provides a peptide wherein Pg$^1$ is independently selected from the group consisting of acetonide, (tert-butyl) ether, methyl ether, benzyl ether, 4-methoxybenzyl ether, allyl ether, methoxymethyl ether, triphenylmethyl (Trt), and acetate ester; wherein two Pg$^1$ groups may combine to form an acetonide protecting group; Pg$^2$ is independently selected from the group consisting of N-acetate, t-butyl carbamate (BOC), carboxybenzyl carbamate (Cbz), (9-fluorenylmethyl) carbamate (FMOC), (trichloroethyl) carbamate (TROC), triphenylmethyl (Trt), and N-[1-(4,4-dimethyl-2,6-dioxocyclohex-1-ylidene)ethyl](Dde); Pg$^3$ is independently selected from the group consisting of methyl ester, tert-butyl ester (Ot-Bu), benzyl ester, p-methoxybenzyl ester, 3,4-dimethoxybenzyl ester, and trityl ester; and Pg$^4$ is independently selected from the group consisting of tert-butyl thioether, methyl thioether, benzyl thioether, 4-methoxybenzyl thioether, allyl thioether, methoxymethyl thioether, triphenylmethyl thio(STrt), and acetate thioester. In further embodiments, the invention provides a peptide comprising at least 2, 3, 4, 5, 6, 7, 8, 9, 10, 11, 12, 13, 14, 15, 16, 17, 18, 19, or 20 contiguous amino acids of CD59 having a consecutive sequence found in CD59. In certain embodiments, the invention provides a peptide of at least 5 contiguous amino acids of CD59 having a consecutive sequence found in CD59. In further embodiments, the invention provides the peptide wherein $R^4$ is identical to a peptide segment selected from residues 1-103 of CD59. In certain embodiments, the invention provides the peptide wherein $R^5$ is identical to a peptide segment selected from residues 1-103 of CD59. In further embodiments, the invention provides peptides wherein $R^4$ is homologous to a peptide segment selected from residues 1-103 of CD59. In certain embodiments, the invention provides peptides wherein $R^5$ is homologous to a peptide segment selected from residues 1-103 of CD59. In further embodiments, the invention provides peptides wherein $R^4$ is at least 99%, 98%, 97%, 96%, 95%, 94%, 93%, 92%, 91%, 90%, 89%, 88%, 87%, 85%, 86%, 85%, 84%, 83%, 82%, 81%, 80%, 75%, 70%, 65%, 60%, 55%, 50%, 45%, 40%, 35%, 30%, 25%, or 20% homologous to a peptide segment selected from residues 1-103 of CD59. In certain embodiments, the invention provides the peptide wherein $R^5$ is at least 99%, 98%, 97%, 96%, 95%, 94%, 93%, 92%, 91%, 90%, 89%, 88%, 87%, 85%, 86%, 85%, 84%, 83%, 82%, 81%, 80%, 75%, 70%, 65%, 60%, 55%, 50%, 45%, 40%, 35%, 30%, 25%, or 20% homologous to a peptide segment selected from residues 1-103 of CD59. In further embodiments, the invention provides peptides wherein $R^4$ has one or more amino acid deletions, insertions, or substitutions relative to a peptide segment selected from residues 1-103 of CD59. In certain embodiments, the invention provides peptides wherein $R^5$ has one or more amino acid deletions, insertions, or substitutions relative to a peptide segment selected from residues 1-103 of CD59.

In certain embodiments, the invention provides a peptide segment selected from residues 1-103 of CD59, wherein a glycophosphatidylinositol moiety is bound to the C-terminus. In further embodiments, the invention provides a peptide segment selected from residues 1-102 of CD59. In certain embodiments, the invention provides a peptide segment selected from residues 1-102 of CD59, wherein a glycophosphatidylinositol moiety is bound to the C-terminus.

In further embodiments, the invention provides peptides wherein two or more of the lysines selected from the group consisting of K14, K30, K38, K65, K66, and K85, are of the formula:

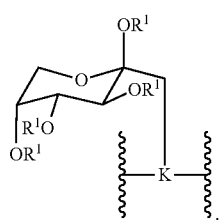

In another aspect, the invention provides a peptide comprising a segment of CD59 of the formula:

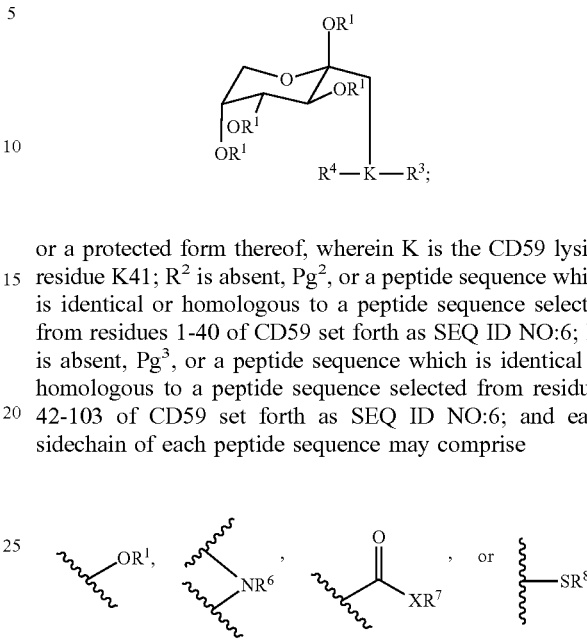

or a protected form thereof, wherein K is the CD59 lysine residue K41; $R^2$ is absent, $Pg^2$, or a peptide sequence which is identical or homologous to a peptide sequence selected from residues 1-40 of CD59 set forth as SEQ ID NO:6; $R^3$ is absent, $Pg^3$, or a peptide sequence which is identical or homologous to a peptide sequence selected from residues 42-103 of CD59 set forth as SEQ ID NO:6; and each sidechain of each peptide sequence may comprise groups; wherein each $R^6$ is hydrogen or $Pg^2$; each X is O or NH; each $R^7$ is hydrogen; $Pg^2$, or $Pg^3$; each $R^8$ is hydrogen or $Pg^4$; each $Pg^1$ is an independently selected hydroxyl protecting group; each $Pg^2$ is an independently selected amino protecting group; each $Pg^3$ is an independently selected carboxyl protecting group; and each $Pg^4$ is an independently selected thiol protecting group.

In certain embodiments, the invention provides the peptide wherein: $Pg^1$ is independently selected from the group consisting of acetonide, (tert-butyl) ether, methyl ether, benzyl ether, 4-methoxybenzyl ether, allyl ether, methoxymethyl ether, triphenylmethyl (Trt), and acetate ester; wherein two $Pg^1$ groups may combine to form an acetonide protecting group; $Pg^2$ is independently selected from the group consisting of N-acetate, t-butyl carbamate (BOC), carboxybenzyl carbamate (Cbz), (9-fluorenylmethyl) carbamate (FMOC), (trichloroethyl) carbamate (TROC), triphenylmethyl (Trt), and N-[1-(4,4-dimethyl-2,6-dioxocyclohex-1-ylidene)ethyl](Dde); $Pg^3$ is independently selected from the group consisting of methyl ester, tert-butyl ester (Ot-Bu), benzyl ester, p-methoxybenzyl ester, 3,4-dimethoxybenzyl ester, and trityl ester; and $Pg^4$ is independently selected from the group consisting of tert-butyl thioether, methyl thioether, benzyl thioether, 4-methoxybenzyl thioether, allyl thioether, methoxymethyl thioether, triphenylmethyl thio(STrt), and acetate thioester. In further embodiments, the invention provides the peptide comprising at least 5, 6, 7, 8, 9, 10, 11, 12, 13, 14, 15, 16, 17, 18, 19 or 20 or more contiguous amino acids of CD59 having a consecutive sequence found in CD59. In certain embodiments, the invention provides the peptide comprising at least five amino acid residues. In further embodiments, the invention provides the peptide wherein 1 to 6 of the lysines residues of CD59 selected from the group consisting of K14, K30, K38, K65, K66, and K85, are of the formula:

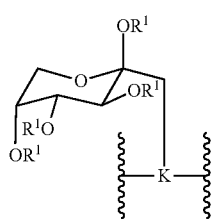

or a protected form thereof. In certain embodiments, the invention provides the peptide wherein R² is identical to a peptide segment selected from residues 1-40 of CD59. In further embodiments, the invention provides the peptide wherein R³ is identical to a peptide segment selected from residues 42-103 of CD59. In certain embodiments, the invention provides the peptide wherein R² is homologous to a peptide segment selected from residues 1-40 of CD59. In further embodiments, the invention provides the peptide wherein R³ is homologous to a peptide segment selected from residues 42-103 of CD59. In certain embodiments, the invention provides the peptide wherein R² is at least 99%, 98%, 97%, 96%, 95%, 94%, 93%, 92%, 91%, 90%, 89%, 88%, 87%, 85%, 86%, 85%, 84%, 83%, 82%, 81%, 80%, 75%, 70%, 65%, 60%, 55%, 50%, 45%, 40%, 35%, 30%, 25%, or 20% homologous to a peptide segment selected from residues 1-40 of CD59. In further embodiments, the invention provides the peptide wherein R³ is at least 99%, 98%, 97%, 96%, 95%, 94%, 93%, 92%, 91%, 90%, 89%, 88%, 87%, 85%, 86%, 85%, 84%, 83%, 82%, 81%, 80%, 75%, 70%, 65%, 60%, 55%, 50%, 45%, 40%, 35%, 30%, 25%, or 20% homologous to a peptide segment selected from residues 42-103 of CD59. In certain embodiments, the invention provides the peptide wherein R² has one or more amino acid deletions, insertions, or substitutions relative to a peptide segment selected from residues 1-40 of CD59. In further embodiments, the invention provides the peptide wherein R³ has one or more amino acid deletions, insertions, or substitutions relative to a peptide segment selected from residues 42-103 of CD59. In certain embodiments, the invention provides a peptide comprising a segment of the formula:

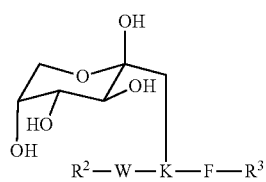

or a protected form thereof. In further embodiments, the invention provides a peptide comprising a segment of the formula:

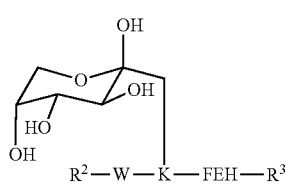

(SEQ ID NO: 1)

or a protected form thereof. In certain embodiments, the invention provides a peptide comprising a segment of the formula:

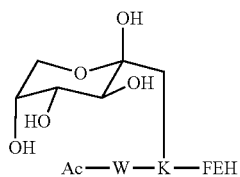

(SEQ ID NO: 1)

or a protected form thereof. In further embodiments, the invention provides a peptide comprising a segment of the formula:

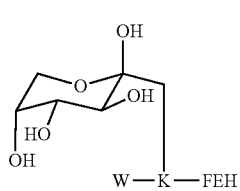

(SEQ ID NO: 1)

or a protected form thereof. In certain embodiments, the invention provides the peptide comprising a segment of the formula:

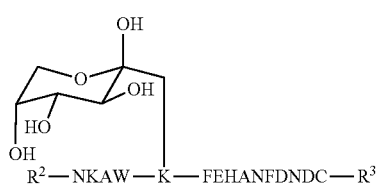

(SEQ ID NO: 3)

or a protected form thereof. In further embodiments, the invention provides a peptide comprising a segment of the formula:

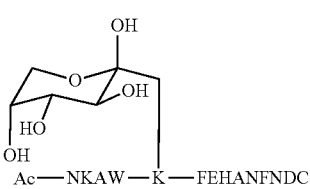

(SEQ ID NO: 3)

or a protected form thereof. In certain embodiments, the invention provides a peptide comprising a segment of the formula:

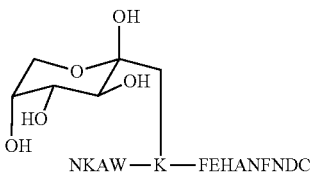
(SEQ ID NO: 3)

or a protected form thereof.

In another aspect, the invention provides a peptide comprising a segment of the formula:

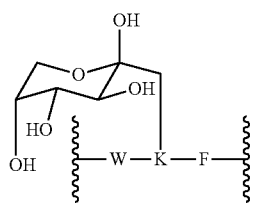

or a protected form thereof. In one embodiment, the invention provides a peptide of the formula:

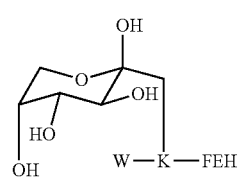
(SEQ ID NO: 1)

or a protected form thereof. In certain embodiments, the invention provides a peptide of the formula:

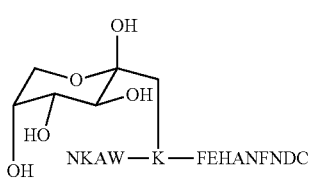
(SEQ ID NO: 3)

or a protected form thereof. In further embodiments, the invention provides a peptide of the formula:

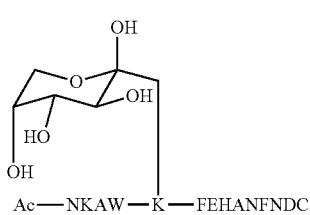
(SEQ ID NO: 3)

or a protected form thereof.

As indicated, one aspect of the invention provides glycated Amadori products of the CD59 polypeptide and fragments thereof. In certain embodiments, a glycated Amadori product of a CD59 fragment can be as small as 5 amino acids in length, such as WKFEH (SEQ ID NO:1) or a protected form thereof. In addition, one or more amino acids that correspond to amino acids of CD59 or a modified CD59 as described herein can be added to either or both ends of the glycated Amadori products of WKFEH (SEQ ID NO:1). For example, one or more amino acids may be added to the N-terminal end and/or one or more amino acids may be added to the C-terminal end of SEQ ID:1. It will be understood that 1, 2, 3, 4, 5, 6, 7, 8, 9, 10, 11, 12, 13, 14, 15, 16, 17, 18, 19, 20, or more amino acids that correspond to an amino acid of CD59 or a modified CD59 as described herein can be added to one or both ends of the amino acid sequence of WKFEH (SEQ ID NO:1). Therefore, a fragment of the invention may include glycated Amadori products of WKFEH (SEQ ID NO:1) with from 1 to 39 amino acids that correspond to amino acids of CD59 or a modified CD59 as described herein added to the N-terminal end and/or from 1 to 59 amino acids that correspond to amino acids of CD59 or a modified CD59 as described herein added to the C-terminal end. Examples of fragments that include K41, although not intended to be limiting are WKFEHCNFNDVTTRLREN (SEQ ID NO:13); CWKFEHCNFNDVTTRLRENELTY (SEQ ID NO:14); AGLQVYNKCWKFEHCNFNDVTTRLRENELT (SEQ ID NO:15); QVYNKCWKFEHCNFND (SEQ ID NO:16); AGLQVYNKCWKFEHCNF (SEQ ID NO:17); DFDACLITKAGLQVYNKCWKFEHCNFNDVTTRLRENELTYYC (SEQ ID NO:18); KCWKFEHCNFNDVTTRLR (SEQ ID NO:19); KCWKFEHCNFNDVTTRLRENELTYYC (SEQ ID NO:20); VYNKCWKFEHCNF (SEQ ID NO:21); GLQVYNKCWKFEHCNFND (SEQ ID NO:22); YNKCWKFEHCNFNE (SEQ ID NO:23); AGLQVYNKCWKFEHCNFN (SEQ ID NO:24); and NKCWKFEHC (SEQ ID NO:25) or protected forms thereof. In certain embodiments, the fragment is a K14-glycated Amadori fragment.

The invention also includes a glycated Amadori product of a fragment of CD59 that includes a lysine that is or corresponds to K14, K30, K38, K65, K66, or K85. In one embodiments, a glycated Amadori product of a fragment of CD59 is at least five amino acids in length and includes K14 with between 1 and 13 amino acids that correspond to amino acids of CD59 or a modified CD59 as described herein added to the N-terminal end and/or from 1 to 89 amino acids that correspond to amino acids of CD59 or a modified CD59 as described herein added to the C-terminal end. Examples of glycated Amadori products of fragments that include K14, although not intended to be limiting, are PNPTADCKTAVNC (SEQ ID NO:26); DCKTAVNC (SEQ ID NO:27); PNPTADCKTAVNC (SEQ ID NO:28); and LQCYNCPNPTADCK (SEQ ID NO:29). In certain embodiments, the fragment is a K14-glycated Amadori product.

Another glycated Amadori product of a fragment of CD59 is at least five amino acids in length and includes K30, with between 1 and 29 amino acids that correspond to amino acids of CD59 or a modified CD59 as described herein added to the N-terminal end and/or from 1 to 73 amino acids that correspond to amino acids of CD59 or a modified CD59 as described herein added to the C-terminal end. Examples of such fragments that include K30, although not intended to be limiting, are DFDACLITKAGLQ (SEQ ID NO:30); FDACLITKAGLQVY (SEQ ID NO:31); CLITKAGLQVYN (SEQ ID NO:32); and DFDACLITKAG (SEQ ID NO:33). In certain embodiments, the fragment is a K30-glycated Amadori product.

Another glycated Amadori product of a fragment of CD59 is at least five amino acids in length and includes K38 with between 1 and 37 amino acids that correspond to amino acids of CD59 or a modified CD59 as described herein added to the N-terminal end and/or from 1 to 65 amino acids that correspond to amino acids of CD59 or a modified CD59 as described herein added to the C-terminal end. Examples of fragments that include K38, although not intended to be limiting, are QVYNKCW (SEQ ID NO:34); VYNKCW (SEQ ID NO:35); AGLQVYNKCW (SEQ ID NO:36); and AGLQVYNKCWKFEHC (SEQ ID NO:37). In certain embodiments, the fragment is a K38-glycated Amadori product.

Another glycated Amadori product of a fragment of CD59 is at least five amino acids in length and includes K65 with between 1 and 64 amino acids that correspond to amino acids of CD59 or a modified CD59 as described herein added to the N-terminal end and/or from 1 to 38 amino acids that correspond to amino acids of CD59 or a modified CD59 as described herein added to the C-terminal end. A glycated Amadori product of a fragment of CD59 that is useful in the invention is at least five amino acids in length and includes K66, with between 1 and 65 amino acids that correspond to amino acids of CD59 or a modified CD59 as described herein added to the N-terminal end and/or from 1 to 37 amino acids that correspond to amino acids of CD59 or a modified CD59 as described herein added to the C-terminal end. Examples of fragments that include K65 and K66, although not intended to be limiting, are LTYYCCKKDLCNFNEQ (SEQ ID NO:38); NELTYYCCKKDLCNF (SEQ ID NO:39); LRENELTYYCCKKDLC (SEQ ID NO:40); CNFNDVTTRLRENELTYYCCKKDLC (SEQ ID NO:41); YCCKKDLC (SEQ ID NO:42); TTRLRENELTYYCCKKDLC (SEQ ID NO:43); VTTRLRENELTYYCCKKDLCN (SEQ ID NO:44); and FNDVTTRLRENELTYYCCKKD (SEQ ID NO:45) or protected forms thereof. In certain embodiments, the fragment is a K65- and/or a K66-glycated Amadori product.

Another glycated Amadori product of a fragment of CD59 is at least five amino acids in length and includes K85 with between 1 and 84 amino acids that correspond to amino acids of CD59 or a modified CD59 as described herein added to the N-terminal end and/or from 1 to 18 amino acids that correspond to amino acids of CD59 or a modified CD59 as described herein added to the C-terminal end. Examples of fragments that include K85, although not intended to be limiting, are GTSLSEKTVLLLVTPF (SEQ ID NO:46); LSEKTVLLLVTPFL (SEQ ID NO:47); TSLSEKTVLL (SEQ ID NO:48); and LENGGTSLSEKTV (SEQ ID NO:49) or protected forms thereof. In certain embodiments, the fragment is a K85-glycated Amadori product.

It will be understood by those of ordinary skill in the art that it is preferable that a glycated Amadori product of a fragment of CD59 for use as an immunogenic fragment in the methods of the invention be at least 5, 6, 7, 8, 9, 10, 11, 12, 13, 14, 15, 16, 17, 18, 19, 20, or more amino acids in length. If a fragment of CD59 includes more than one lysine residue, it is desirable that in certain embodiments only one of the lysine residues is a glycated Amadori product. One of ordinary skill in the art will be able to use the guidance provided herein to make additional glycated Amadori products of fragments of CD59.

The CD59 amino acid sequence and fragments thereof can be modified in one or more ways. Modifications of the amino acids sequence include deletions, insertions, or substitutions such as substituting of one or more cysteine residues with alanine residues, and/or adding a cysteine residue to the C-terminus. For example, the cysteine residues in positions 3 and 9 of SEQ ID NO:4 can be replaced with alanine residues, to reduce S—S bridging in the polypeptide. Further, a cysteine residue may be added to the C-terminus of SEQ ID NO:4 to create a "handle" for conjugation of the resulting peptide to an affinity column or a carrier protein. The resulting modified polypeptide fragment of CD59 is set forth as NKAWKFEHANFNDC (SEQ ID NO:3). One of ordinary skill in the art will recognize that there are additional polypeptide fragments of CD59 that can be used and/or modified. Thus, the invention includes polypeptides with an epitope of interest, e.g. WKFEH (SEQ ID NO:1), that may be flanked on either or both sides with one or more additional amino acids that correspond to an amino acid sequence of CD59 and may include modifications of the amino acid sequence of CD59 as described herein.

In one aspect, the invention provides isolated human CD59 with glycated K41 of the formula:

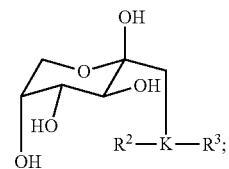

wherein $R^2$ is a peptide sequence which is identical or homologous to a peptide sequence selected from residues 1-40 of CD59 set forth as SEQ ID NO:6; and $R^3$ is a peptide sequence which is identical or homologous to a peptide sequence selected from residues 42-103 of CD59 set forth as SEQ ID NO:6. In some embodiments, the invention provides isolated human CD59 which can include various deletions, insertions, substitutions, additions, post-translational modifications, and chemical modifications. In further embodiments, the invention provides glycated Amadori products of isolated human CD59 which can include various deletions, insertions, substitutions, additions, post-translational modifications, and chemical modifications.

Methods of Preparing Glycated Amadori Products of the CD59 Polypeptide and Fragments Thereof One aspect of the invention includes methods of preparing glycated Amadori products of the CD59 polypeptide and fragments thereof. In some embodiments, the glycated Amadori product is installed into the CD59 polypeptide and fragments thereof by incorporating glycated Amadori products of individual amino acids, such as lysine, into a growing polypeptide chain using a stepwise solid-phase synthetic strategy. In further embodiments, the glycated Amadori products of individual amino acids, such as lysine, are fully or partially protected with protecting groups. In some embodiments, glycated Amadori products are installed into sidechains of a preformed CD59 polypeptide or a fragment thereof. In further embodiments, some or all of the sidechains are protected. In some embodiments, a reductive amination synthetic strategy is used to incorporate the glycated Amadori products into the sidechains of a preformed CD59 polypeptide or a fragment thereof. In further embodiments, the reductive amination synthetic strategy is conducted upon sidechains of a polypeptide in solution. In some embodiments, the reductive amination synthetic strategy is conducted upon sidechains of a solid-phase polypeptide. In further embodiments, a direct glycation synthetic strategy is used to incorporate the glycated Amadori products into sidechains of a preformed CD59 polypeptide or a fragment thereof. In some embodiments, the direct glycation synthetic strategy is conducted upon sidechains of a polypeptide in solution. In further embodiments, the direct glycation synthetic strategy is conducted upon sidechains of a solid-phase polypeptide.

In yet another aspect, the invention provides a method of solid phase synthesis of a peptide of the sequence,

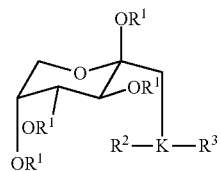

or a protected form thereof, comprising a lysine derivative of the formula:

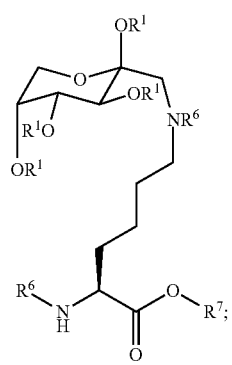

or a protected form thereof, wherein each $R^1$ is independently hydrogen or $Pg^1$ and wherein two $Pg^1$ groups may combine to form a heterocyclic ring; $R^2$ is absent, $Pg^2$, or a peptide sequence which is identical or homologous to a peptide sequence selected from residues 1-40 of CD59 set forth as SEQ ID NO:6; $R^3$ is absent, $Pg^3$, or a peptide sequence which is identical or homologous to a peptide sequence selected from residues 42-103 of CD59 set forth as SEQ ID NO:6; and each sidechain of each peptide sequence may comprise

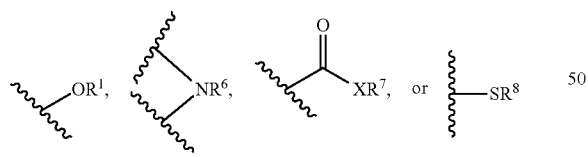

groups; wherein each $R^6$ is hydrogen or $Pg^2$; each X is O or NH; each $R^7$ is hydrogen; $Pg^2$, or $Pg^3$; each $R^8$ is hydrogen or $Pg^4$; each $Pg^1$ is an independently selected hydroxyl protecting group; each $Pg^2$ is an independently selected amino protecting group; each $Pg^3$ is an independently selected carboxyl protecting group; and each $Pg^4$ is an independently selected thiol protecting group.

In certain embodiments, the invention provides methods wherein each $Pg^1$ is an independently selected hydroxyl protecting group as defined herein, each $Pg^2$ is an independently selected amino protecting group as defined herein, and wherein two $Pg^1$ groups may combine to form a heterocyclic ring. In certain embodiments, two $Pg^1$ groups may combine to form an acetonide protecting group. In certain embodiments, each $Pg^1$ group is independently selected from the group consisting of (tert-butyl) ether, methyl ether, benzyl ether, 4-methoxybenzyl ether, allyl ether, methoxymethyl ether, triphenylmethyl (Trt), and acetate ester protecting groups. In certain embodiments, each $Pg^2$ group is independently selected from the group consisting of t-butyl carbamate (BOC), carboxybenzyl carbamate (Cbz), (9-fluorenylmethyl) carbamate (FMOC), (trichloroethyl) carbamate (TROC), triphenylmethyl (Trt), and N-[1-(4,4-dimethyl-2,6-dioxocyclohex-1-ylidene)ethyl](Dde) protecting groups. The general principles of solid-phase peptide synthesis are described in *Solid-Phase Synthesis: A Practical Guide*, Fernando Albericio, CRC Press: 2000, the entire contents of which are incorporated herein by reference.

In certain embodiments, the invention provides methods wherein the lysine derivative is of the formula:

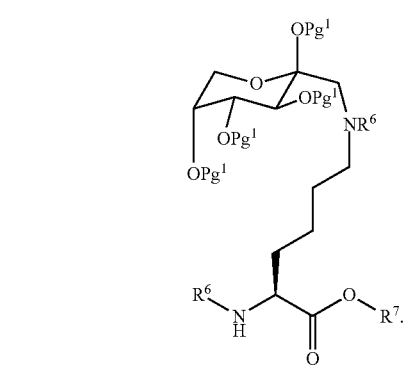

In further embodiments, the invention provides methods wherein the lysine derivative is of the formula:

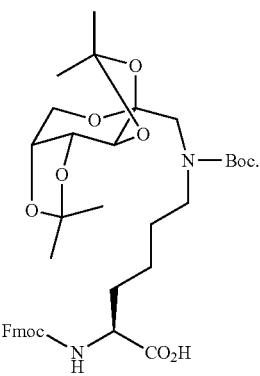

In certain aspects, the invention provides methods of preparing a peptide of the sequence,

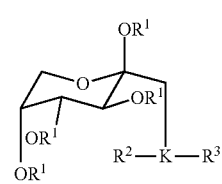

or a protected form thereof, comprising: providing a peptide of the sequence, $R^2$—K—$R^3$, and glycating K41 of the peptide with D-glucose; wherein each $R^1$ is independently hydrogen or $Pg^1$ and wherein two $Pg^1$ groups may combine to form a heterocyclic ring; $R^2$ is absent, $Pg^2$, or a peptide sequence which is identical or homologous to a peptide sequence selected from residues 1-40 of CD59 set forth as SEQ ID NO:6; $R^3$ is absent, $Pg^3$, or a peptide sequence which is identical or homologous to a peptide sequence selected from residues 42-103 of CD59 set forth as SEQ ID NO:6; and each sidechain of each peptide sequence may comprise

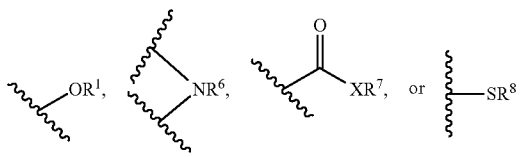

groups; wherein each $R^6$ is hydrogen or $Pg^2$; each X is O or NH; each $R^7$ is hydrogen; $Pg^2$, or $Pg^3$; each $R^8$ is hydrogen or $Pg^4$; each $Pg^1$ is an independently selected hydroxyl protecting group; each $Pg^2$ is an independently selected amino protecting group; each $Pg^3$ is an independently selected carboxyl protecting group; and each $Pg^4$ is an independently selected thiol protecting group.

In certain embodiments, the invention provides a method comprising providing a peptide of the sequence: $R^2$-WKFEH-$R^3$ (SEQ ID NO: 2) or a protected form thereof. In further embodiments, the invention provides a method comprising providing a peptide of the sequence: $R^2$-NKAWKFEHANFNDC-$R^3$ (SEQ ID NO: 10) or a protected form thereof. In certain embodiments, the invention provides methods wherein the step of glycating is performed on a resin. In further embodiments, the invention provides methods wherein the step of glycating is performed in solution. In certain embodiments, the invention provides methods comprising a 2-fold to 100-fold molar excess of D-glucose. In further embodiments, the invention provides methods wherein the glycating step is performed at temperatures above 50° C. In still further embodiments, the invention provides methods wherein the glycating step is performed at temperatures above 25° C., 30° C., 35° C., 40° C., or 45° C. In some embodiments, the invention provides methods wherein the glycating step is performed at temperatures above 55° C., 60° C., 65° C., 70° C., 75° C., 80° C., 85° C., 90° C., 95° C., or 100° C.

In one aspect, the invention provides a method of preparing a peptide of the sequence,

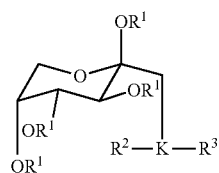

or a protected form thereof, comprising: providing a peptide of the sequence, $R^2$—K—$R^3$ or a protected form thereof, reacting the peptide with an aldehyde of formula:

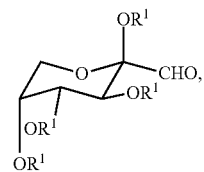

under suitable conditions to form with the peptide a Schiff's base of the formula:

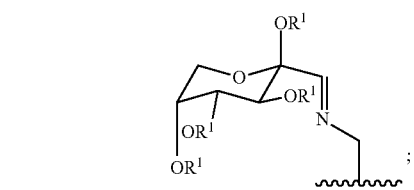

and reducing the Schiff's base to an amine of the formula:

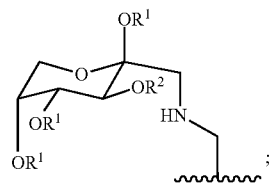

wherein each $R^1$ is independently hydrogen or $Pg^1$ and wherein two $Pg^1$ groups may combine to form a heterocyclic ring; $R^2$ is absent, $Pg^2$, or a peptide sequence which is identical or homologous to a peptide sequence selected from residues 1-40 of CD59 set forth as SEQ ID NO:6; $R^3$ is absent, $Pg^3$, or a peptide sequence which is identical or homologous to a peptide sequence selected from residues 42-103 of CD59 set forth as SEQ ID NO:6; and wherein each sidechain of each peptide sequence may comprise

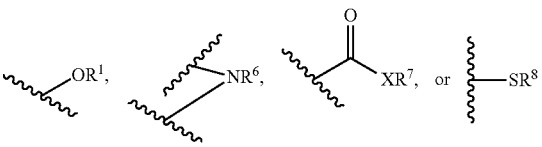

groups; wherein each $R^6$ is hydrogen or $Pg^2$; each X is O or NH; each $R^7$ is hydrogen; $Pg^2$, or $Pg^3$; each $R^8$ is hydrogen or $Pg^4$; each $Pg^1$ is an independently selected hydroxyl protecting group; each $Pg^2$ is an independently selected amino protecting group; each $Pg^3$ is an independently selected carboxyl protecting group; and each $Pg^4$ is an independently selected thiol protecting group.

In certain embodiments, the invention provides a method comprising providing a peptide of the sequence: $R^2$-WKFEH-$R^3$ (SEQ ID NO: 2) or a protected form thereof. In further embodiments, the invention provides a method comprising providing a peptide of the sequence: $R^2$-NKAWKFEHANFNDC-$R^3$ (SEQ ID NO: 10) or a protected form thereof. In certain embodiments, the invention provides a method comprising a 2-fold to 100-fold molar excess of aldehyde. In further embodiments, the invention provides a method wherein the Schiff's base is prepared at temperatures above 25° C. In still further embodiments, the invention provides methods wherein the glycating step is performed at temperatures above 25° C., 30° C., 35° C., 40° C., or 45° C. In some embodiments, the invention provides methods wherein the glycating step is performed at temperatures above 55° C., 60° C., 65° C., 70° C., 75° C., 80° C., 85° C., 90° C., 95° C., or 100° C. In certain embodiments, the invention provides methods wherein the step of reacting is performed on a resin. In further embodiments, the invention provides methods wherein the step of reacting is performed in solution.

In one aspect, the invention provides a peptide comprising a segment of the formula:

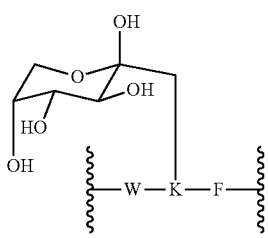

or a protected form thereof. In one embodiment, the invention provides a peptide of the formula:

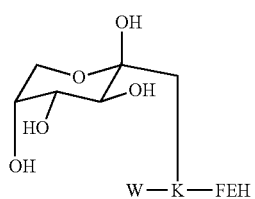
(SEQ ID NO: 1)

or a protected form thereof. In certain embodiments, the invention provides a peptide of the formula:

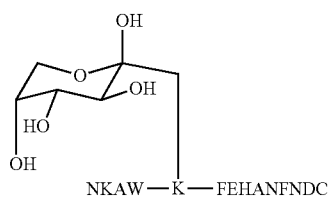
(SEQ ID NO: 3)

or a protected form thereof. In further embodiments, the invention provides a peptide of the formula:

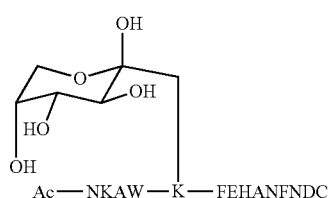
(SEQ ID NO: 3)

or a protected form thereof.

In one aspect, the invention provides a method of preparing a peptide of the invention comprising: providing a peptide of the sequence, NKAWKFEHANFNDC (SEQ ID NO: 10), or a protected form thereof; and glycating the peptide with D-glucose. In one embodiment, the invention provides the method wherein the step of glycating is performed on a resin. In another embodiment, the invention provides the method wherein the step of glycating is performed in solution. In another embodiment, the invention provides the method wherein the method only leads to the glycation of the second lysine. In yet another embodiment, the invention provides a method of preparing a peptide of the invention comprising: providing a peptide of the sequence, NKAWKFEHANFNDC (SEQ ID NO: 10), or a protected form thereof; reacting the peptide with an aldehyde of formula:

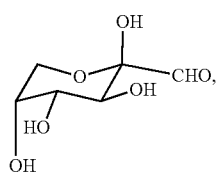 [SMILES: O=CC1(O)OCC(O)C(O)C1O]

or a protected form thereof, under suitable conditions to form a Schiff's base with the peptide; and reducing the Schiff's base. In some embodiments, the invention provides the method wherein the step of reacting is performed on a resin. In another embodiment, the invention provides the method wherein the step of reacting is performed in solution. In yet another

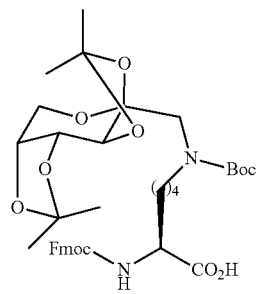

embodiment, the invention provides the method wherein the method only leads to the glycation of the second lysine. In some embodiments, the invention provides the method of preparing a peptide of the invention comprising incorporating an amino acid of the formula:
into a peptide by stepwise synthesis.

Antibodies and Fragments Thereof

The invention also provides antibodies that bind to a glycated Amadori product of CD59 polypeptide. The invention further provides methods of making such antibodies that may specifically bind to a glycated Amadori product of CD59 polypeptide. As used herein, the term "glycated Amadori product of CD59" polypeptide includes mature CD59 polypeptide with one or more glycated lysine (K) residues which have undergone Amadori rearrangement. In certain embodiments, the glycated Amadori lysine residue of CD59 is residue K41 of mature CD59. One of ordinary skill in the art will understand that a fragment of CD59 can be compared to mature or full-length CD59, and the presence of a residue in that fragment is said to "correspond" to the residue of mature or full-length CD59. As used herein therefore, residue positions for lysines are identified as they occur in mature or full-length CD59, whether that residue is part of mature or full-length CD59 or part of a fragment or modified fragment thereof. Thus, K41 maintains that designation in mature CD59 or fragments thereof. In certain embodiments, the glycated lysine residue in a fragment of CD59 is K41. In certain embodiments of the invention, the glycated residue of CD59 or a fragment thereof is or corresponds to K14, K30, K38, K65, K66, or K85 of mature CD59 polypeptide. In certain embodiments, more than one K residue of a polypeptide or fragment thereof is glycated.

In certain embodiments, the invention provides an isolated antibody or antibody fragment, which specifically binds the epitope comprising the glycated Amadori product of lysine of peptides described herein. In certain embodiments, the invention provides an isolated antibody or antibody fragment wherein the lysine of the peptide of the Amadori product is K41. In further embodiments, the invention provides an isolated antibody or antibody fragment wherein the epitope comprises K41 of the glycated Amadori product of NKAWKFEHANFNDC (SEQ ID NO: 3). In certain embodiments, the invention provides an isolated antibody or antibody fragment wherein the epitope comprises K41 of the glycated Amadori product of WKFEH (SEQ ID NO: 1). In further embodiments, the invention provides an isolated antibody or antibody fragment wherein the antibody or antibody fragment is polyclonal. In certain embodiments, the invention provides an isolated antibody or antibody fragment wherein the antibody or antibody fragment is monoclonal. In further embodiments, the invention provides an isolated antibody or antibody fragment wherein the antibody or antibody fragment is recombinant. In certain embodiments, the invention provides an isolated antibody or antibody fragment attached to a detectible label. In further embodiments, the invention provides an isolated antibody or antibody fragment wherein the detectable label is a fluorescent label, an enzyme label, a radioactive label, a nuclear magnetic resonance active label, a luminescent label, or a chromophore label. In certain embodiments, the invention provides an isolated antibody or antibody fragment wherein the antibody fragment is a F(ab')$_2$ fragment, F(ab') fragment, F(ab) fragment, or a single chain Fv fragment. In further embodiments, the invention provides the isolated antibody or antibody fragment is in a lyophilized form. In certain embodiments, the isolated antibody or antibody fragment is in an aqueous medium. In further embodiments, the antibody fragment binds to a conformational epitope. The inventive antibody or antibody fragment may be part of a kit (e.g., a diagnostic kit).

The invention also provides nucleic acid sequences that encode the antibodies or antibody fragments described herein. In certain embodiments, the invention provides a hybridoma that comprises such a nucleic acid. Hybridoma cell lines that produce the antibody or antibody fragment of the invention are also provided. In certain embodiments, the invention provides a hybridoma that comprises a nucleic acid that encodes an antibody that distinguishes between glycated Amadori products of CD59, or fragments thereof, and non-glycated products of CD59, or fragments thereof. In certain embodiments, the invention provides an expression vector comprising an isolated nucleic acid molecule encoding an antibody or antibody fragment of the invention. In yet another aspect, the invention provides a host cell transformed by or transfected with such an expression vector. In certain aspects, the invention provides a plasmid which produces the antibody or antibody fragment of the invention.

In another aspect, the invention provides a method of making an antibody that specifically binds to the glycated Amadori product of CD59 but not to non-glycated CD59, comprising preparing an immunogenic CD59 polypeptide of the invention, and immunizing an animal with the immunogenic CD59 polypeptide.

In certain embodiments, the method of providing an Ab comprises: removing a lymph node from the immunized animal, harvesting cells from the removed lymph node, fusing the harvested cells with myeloma cells to make hybridomas, expanding the hybridomas, identifying a hybridoma that produces an antibody that specifically binds to the immunogenic polypeptide, and collecting the antibody produced by the hybridoma. In certain embodiments, the animal is a mouse. In certain embodiments, the myeloma cells are AG8 cells. In further embodiments, the invention provides the method wherein the immunogenic glycated Amadori peptide has the amino acid sequence of NKAWKFEHANFNDC (SEQ ID NO:3). In certain embodiments, the invention provides the method wherein the immunogenic glycated Amadori peptide has the amino acid sequence set forth as WKFEH (SEQ ID NO:1).

The methods of the invention include the use of an immunogenic polypeptide for the production of an antibody directed to a glycated Amadori product of CD59. In certain embodiments, the antigenic polypeptide can be less than twenty-five amino acids in length. In certain embodiments, the antigenic polypeptide can be as small as five amino acids in length. For example, WKFEH (SEQ ID NO:1) is an antigenic fragment that may be used to generate antibodies that specifically recognize the glycated Amadori product of CD59. In certain embodiments, when the size of the polypeptide is less than about eight amino acids in length, a second carrier molecule, e.g. bovine serum albumin (BSA), may be attached to the peptide to increase antigenicity of the polypeptide. Thus, small fragments of CD59 that include the desired epitope for antibody production can be used in the production of an antibody that specifically binds to the epitope. As set forth herein, SEQ ID NO:2 is WKFEH, wherein the K residue is not glycated.

In certain embodiment, antibodies that specifically bind WKFEH (SEQ ID NO:1) are provided. In the preparation of antibodies that specifically bind to the glycated Amadori product of CD59, WKFEH (SEQ ID NO:1) can be used. SEQ ID NO:1 can be used in conjunction with a second molecule, e.g., BSA as described above, as an antigenic polypeptide with which to prepare antibodies that specifically bind to the WKFEH (SEQ ID NO:1) epitope.

In addition, one or more amino acids that correspond to amino acids of CD59 or a modified CD59 as described herein can be added to either or both ends of the WKFEH (SEQ ID NO:1) sequence to make additional immunogenic polypeptides for use in making an antibody of the invention. For example, one or more amino acids may be added to the N-terminal end and/or one or more amino acids may be added to the C-terminal end of SEQ ID:1 for the production of an immunogenic fragment useful in the methods of the invention. It will be understood that 1, 2, 3, 4, 5, 6, 7, 8, 9, 10, 11, 12, 13, 14, 15, 16, 17, 18, 19, 20, or more amino acids that correspond to amino acids of CD59 or a modified CD59 as described herein can be added to one or both ends of the amino acid sequence of WKFEH (SEQ ID NO:1). Therefore, an immunogenic fragment of the invention may include WKFEH (SEQ ID NO:1) with from 1 to 39 amino acids that correspond to amino acids of CD59 or a modified CD59 as described herein added to the N-terminal end and/or from 1 to 59 amino acids that correspond to amino acids of CD59 or a modified CD59 as described herein added to the C-terminal end. Examples of fragments that include K41, although not intended to be limiting, are WKFEHCNFNDVTTRLREN (SEQ ID NO:13); CWKFEHCNFNDVTTRLRENELTY (SEQ ID NO:14); AGLQVYNKCWKFEHCNFNDVTTRLRENELT (SEQ ID NO:15); QVYNKCWKFEHCNFND (SEQ ID NO:16); AGLQVYNKCWKFEHCNF (SEQ ID NO:17); DFDA-CLITKAGLQVYNKCWKFEHCNFNDVTTRLRENEL-TYYC (SEQ ID NO:18); KCWKFEHCNFNDVTTRLR (SEQ ID NO:19); KCWKFEHCNFNDVTTRLRENEL-TYYC (SEQ ID NO:20); VYNKCWKFEHCNF (SEQ ID NO:21); GLQVYNKCWKFEHCNFND (SEQ ID NO:22); YNKCWKFEHCNFNE (SEQ ID NO:23); AGLQVYNKCWKFEHCNFN (SEQ ID NO:24); and NKCWKFEHC (SEQ ID NO:25). In certain embodiments, the fragment is a K14-glycated fragment.

The invention also includes fragments of CD59 that include a lysine that corresponds to K14, K30, K38, K65, K66, or K85 of mature CD59. In certain embodiments of the invention the lysine is glycated. In other embodiments of the invention, the lysine is not glycated. In one embodiment, a fragment of CD59 that is useful in the invention is at least five amino acids in length and includes K14, with between 1 and 13 amino acids that correspond to amino acids of CD59 or a modified CD59 as described herein added to the N-terminal end and/or from 1 to 89 amino acids that correspond to amino acids of CD59 or a modified CD59 as described herein added to the C-terminal end. Examples of fragments that include K14, although not intended to be limiting are: PNPTADCKTAVNC (SEQ ID NO:26); DCK-TAVNC (SEQ ID NO:27); PNPTADCKTAVNC (SEQ ID NO:28); and LQCYNCPNPTADCK (SEQ ID NO:29). In certain embodiments, the fragment is a K14-glycated fragment.

Another fragment of CD59 that is useful in the invention is at least five amino acids in length and includes K30, with between 1 and 29 amino acids that correspond to amino acids of CD59 or a modified CD59 as described herein added to the N-terminal end and/or from 1 to 73 amino acids that correspond to amino acids of CD59 or a modified CD59 as described herein added to the C-terminal end. Examples of fragments that include K30, although not intended to be limiting are: DFDACLITKAGLQ (SEQ ID NO:30); FDA-CLITKAGLQVY (SEQ ID NO:31); CLITKAGLQVYN (SEQ ID NO:32); and DFDACLITKAG (SEQ ID NO:33). In certain embodiments, the fragment is a K30-glycated fragment.

Another fragment of CD59 that is useful in the invention is at least five amino acids in length and includes K38, with between 1 and 37 amino acids that correspond to amino acids of CD59 or a modified CD59 as described herein added to the N-terminal end and/or from 1 to 65 amino acids that correspond to amino acids of CD59 or a modified CD59 as described herein added to the C-terminal end. Examples of fragments that include K38, although not intended to be limiting are: QVYNKCW (SEQ ID NO:34); VYNKCW (SEQ ID NO:35); AGLQVYNKCW (SEQ ID NO:36); and AGLQVYNKCWKFEH (SEQ ID NO:37). In certain embodiments, the fragment is a K38-glycated fragment.

Another fragment of CD59 that is useful in the invention is at least five amino acids in length and includes K65, with between 1 and 64 amino acids that correspond to amino acids of CD59 or a modified CD59 as described herein added to the N-terminal end and/or from 1 to 38 amino acids that correspond to amino acids of CD59 or a modified CD59 as described herein added to the C-terminal end. A fragment of CD59 that is useful in the invention is at least five amino acids in length and includes K66, with between 1 and 65 amino acids that correspond to amino acids of CD59 or a modified CD59 as described herein added to the N-terminal end and/or from 1 to 37 amino acids that correspond to amino acids of CD59 or a modified CD59 as described herein added to the C-terminal end. Examples of fragments that include K65 and K66, although not intended to be limiting, are LTYYCCKKDLCNFNEQ (SEQ ID NO:38); NELTYYCCKKDLCNF (SEQ ID NO:39); LRENEL-TYYCCKKDLC (SEQ ID NO:40); CNFNDVTTRLREN-ELTYYCCKKDLC (SEQ ID NO:41); YCCKKDLC (SEQ ID NO:42); TTRLRENELTYYCCKKDLC (SEQ ID NO:43); VTTRLRENELTYYCCKKDLCN (SEQ ID NO:44); and FNDVTTRLRENELTYYCCKKD (SEQ ID NO:45). In certain embodiments, the fragment is a K65- and/or a K66-glycated fragment.

Another fragment of CD59 that is useful in the invention is at least five amino acids in length and includes K85, with between 1 and 84 amino acids that correspond to amino acids of CD59 or a modified CD59 as described herein added to the N-terminal end and/or from 1 to 18 amino acids that correspond to amino acids of CD59 or a modified CD59 as described herein added to the C-terminal end. Examples of fragments that include K85, although not intended to be limiting, are GTSLSEKTVLLLVTPF (SEQ ID NO:46); LSEKTVLLLVTPFL (SEQ ID NO:47); TSLSEKTVLL (SEQ ID NO:48); and LENGGTSLSEKTV (SEQ ID NO:49). In certain embodiments, the fragment is a K85-glycated fragment.

It will be understood by those of ordinary skill in the art that it is preferable that a fragment of CD59 for use as an immunogenic fragment in the methods of the invention be at least 5, 6, 7, 8, 9, 10, 11, 12, 13, 14, 15, 16, 17, 18, 19, 20, or more amino acids in length. If a fragment of CD59 includes more than one lysine residue, it is desirable that in certain embodiments, only one of the lysine residues is a glycated lysine residue. In other embodiments, more than one lysine is glycated. One of ordinary skill in the art will be able to use the guidance provided herein to make additional fragments of CD59 that can be used in the methods of the invention.

An amino acid sequence for use in methods of the invention to produce an antibody that specifically binds to glycated Amadori product of CD59 can be modified in one or more ways. Modifications of the amino acid sequence means substituting of one or more cysteine residues with alanine residues, and/or adding a cysteine residue to the C-terminus. An example of a fragment of CD59 that can be modified is NKCWKFEHCNFND (SEQ ID NO:4). SEQ ID NO:4 may be modified to include a glucitollysine residue in place of the K at position 5 of the sequence. In addition, the cysteine residues at positions 3 and 9 of SEQ ID NO:4 can be replaced with alanine residue, to reduce S—S bridging in the polypeptide. Further, a cysteine residue may be added to the C-terminus of SEQ ID NO:4 to create a "handle" for conjugation of the resulting peptide to an affinity column or a carrier protein. An exemplary modified polypeptide fragment of CD59 is set forth as NKAWKFEHANFNDC (SEQ ID NO:3) and is useful in the antibody-production methods of the invention. One of ordinary skill in the art will recognize that there are additional polypeptide fragments of CD59 that can be used and/or modified and used in the methods of the invention. Thus, the invention includes polypeptides with an epitope of interest, e.g. WKFEH (SEQ ID NO:1), that may be flanked on either or both sides with one or more additional amino acids that correspond to an amino acid sequence of CD59 and may include modifications of the amino acid sequence of CD59 as described herein.

As used herein with respect to polypeptides, proteins, or fragments thereof, "isolated" means separated from its native environment and present in sufficient quantity to permit its identification or use. Isolated, when referring to a protein or polypeptide, means, for example: (i) selectively produced by expression cloning, or (ii) purified as by chromatography or electrophoresis. Isolated proteins or polypeptides may be, but need not be, substantially pure. The term "substantially pure" means that the proteins or polypeptides are essentially free of other substances with which they may be found in nature or in vivo systems to an extent practical and appropriate for their intended use. Substantially pure polypeptides may be produced by techniques well known in the art. Because an isolated protein may be admixed with a pharmaceutically acceptable carrier in a pharmaceutical preparation, the protein may be only a small percentage by weight of the preparation. The protein is nonetheless isolated in that it has been separated from the substances with which it may be associated in living systems, i.e., isolated from other proteins.

Fragments of a CD59 protein preferably are those fragments that retain a distinct functional capability of the CD59 protein. Functional capabilities which can be retained in a fragment include interactions with antibodies, and interactions with other polypeptides or fragments thereof. Other CD59 protein fragments, e.g., recombinant fragments of SEQ ID NO:5, can be selected. For example, one of ordinary skill in the art can prepare CD59 fragments recombinantly and test those fragments according to the methods exemplified below.

Modifications of a CD59 polypeptide may be made by modification of the nucleic acid which encodes the CD59 polypeptide and may include deletions, point mutations, truncations, amino acid substitutions, and additions of amino acids or non-amino acid moieties. Alternatively, modifications can be made directly to the polypeptide, such as by cleavage, addition of a linker molecule, addition of a detectable moiety, such as biotin, addition of a fatty acid, phosphorylation, acetylation, and the like. Modifications also embrace fusion proteins comprising all or part of the CD59 amino acid sequence.

In general, modified CD59 polypeptides include polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a CD59 polypeptide by eliminating proteolysis by proteases in an expression system (e.g., dibasic amino acid residues in yeast expression systems in which KEX2 protease activity is present).

Modifications conveniently are prepared by altering a nucleic acid molecule that encodes the CD59 polypeptide. Mutations of a nucleic acid which encode a CD59 polypeptide preferably preserve the amino acid reading frame of the coding sequence, and preferably do not create regions in the nucleic acid which are likely to hybridize to form secondary structures, such as hairpins or loops, which can be deleterious to expression of the modified polypeptide.

Modifications can be made by selecting an amino acid substitution, or by random mutagenesis of a selected site in a nucleic acid which encodes the CD59 polypeptide. Modified CD59 polypeptides then can be expressed and tested for one or more activities (e.g., antibody binding) to determine which mutation provides a modified polypeptide with the desired properties. Further mutations can be made to modified CD59 polypeptides (or to non-modified CD59 polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a CD59 coding sequence or cDNA clone to enhance expression of the polypeptide. The activity of modified CD59 polypeptides can be tested by cloning the gene encoding the modified CD59 polypeptide into a bacterial, fungal, or mammalian expression vector, introducing the vector into an appropriate host cell, expressing the modified CD59 polypeptide, and testing for a functional capability of CD59 polypeptides as disclosed herein. The foregoing procedures are well known to one of ordinary skill in the art.

The skilled artisan will also realize that conservative amino acid substitutions may be made in CD59 polypeptides to provide functionally equivalent CD59 polypeptides, i.e., modified CD59 polypeptides that retain the functional capabilities of CD59 polypeptides. As used herein, a "conservative amino acid substitution" refers to an amino acid substitution which does not alter the relative charge or size characteristics of the protein in which the amino acid substitution is made. Modified CD59 polypeptides can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, New York, 1989, or *Current Protocols in Molecular Biology*, F. M. Ausubel, et al., eds., John Wiley & Sons, Inc., New York. Exemplary functionally equivalent CD59 polypeptides include conservative amino acid substitutions of SEQ ID NO:5, or fragments thereof. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Conservative amino-acid substitutions in CD59 polypeptides typically are made by alteration of a nucleic acid encoding a CD59 polypeptide. Such substitutions can be made by a variety of methods known to one of ordinary skill in the art. For example, amino acid substitutions may be made by PCR-directed mutation, site-directed mutagenesis, or by chemical synthesis of a gene encoding a CD59 polypeptide. Where amino acid substitutions are made to a small fragment of a CD59 polypeptide, the substitutions can be made by directly synthesizing the peptide. The activity of functionally equivalent fragments of CD59 polypeptides can be tested by cloning the gene encoding the altered CD59 polypeptide into a bacterial, fungal, or mammalian expression vector, introducing the vector into an appropriate host cell, expressing the altered CD59 polypeptide, and testing for a functional capability of the CD59 polypeptides as disclosed herein.

The methods of the invention include the use of polypeptide fragments of CD59 for the production of antibodies that specifically bind to a glycated Amadori product of CD59. In certain embodiments, the glycated residue on CD59 that is part of the epitope specifically recognized by the antibody is the lysine residue that corresponds to K41 of CD59. The invention also includes nucleic acid sequences that encode the polypeptide sequences of the invention. For example, the invention includes nucleic acid sequences that encode a CD59 polypeptide or fragment thereof, and includes the use of the nucleic acid sequences for the production of the polypeptide sequences. The full-length nucleic acid sequence of CD59 is set forth herein as SEQ ID NO:9.

Additional nucleic acids of the invention include nucleic acids that encode an antibody or antigen-binding fragment of the invention. In certain embodiments, a nucleic acid of the invention is a nucleic acid molecule that is highly homologous to a nucleic acid that encodes an antibody or antigen-binding fragment of the invention. Preferably the homologous nucleic acid molecule comprises a nucleotide sequence that is at least about 90% identical to the nucleotide sequence that encodes the antibody or antigen-binding fragment thereof. More preferably, the nucleotide sequence is at least about 95% identical, at least about 97% identical, at least about 98% identical, or at least about 99% identical to a nucleotide sequence that encodes an antibody or antigen-binding fragment of the invention. The homology can be calculated using various, publicly available software tools well known to one of ordinary skill in the art. Exemplary tools include the BLAST system available from the website of the National Center for Biotechnology Information (NCBI) at the National Institutes of Health.

One method of identifying highly homologous nucleotide sequences is via nucleic acid hybridization. Thus the invention also includes antibodies having the glycated Amadori product of CD59-binding properties and other functional properties described herein, which are encoded by nucleic acid molecules that hybridize under high stringency conditions to a nucleic acid that encodes an antibody or antigen-binding fragment of the invention. Identification of related sequences can also be achieved using polymerase chain reaction (PCR) and other amplification techniques suitable for cloning related nucleic acid sequences. Preferably, PCR primers are selected to amplify portions of a nucleic acid sequence of interest, such as a CDR.

The term "high stringency conditions" as used herein refers to parameters with which the art is familiar. Nucleic acid hybridization parameters may be found in references that compile such methods, e.g. *Molecular Cloning: A Laboratory Manual*, J. Sambrook, et al., eds., Second Edition, Cold Spring Harbor Laboratory Press, Cold Spring Harbor, New York, 1989, or *Current Protocols in Molecular Biology*, F. M. Ausubel, et al., eds., John Wiley & Sons, Inc., New York. One example of high-stringency conditions is hybridization at 65° C. in hybridization buffer (3.5×SSC, 0.02% Ficoll, 0.02% polyvinyl pyrrolidone, 0.02% bovine serum albumin, 2.5 μM $NaH_2PO_4$ (pH=7), 0.5% SDS, 2 μM EDTA). SSC is 0.15M sodium chloride/0.015M sodium citrate, pH=7; SDS is sodium dodecyl sulphate; and EDTA is ethylenediaminetetracetic acid. After hybridization, a membrane upon which the nucleic acid is transferred is washed, for example, in 2×SSC at room temperature and then at 0.1-0.5×SSC/0.1×SDS at temperatures up to 68° C.

As used herein, the term "antibody" refers to a glycoprotein comprising at least two heavy (H) chains and two light (L) chains inter-connected by disulfide bonds. Each heavy chain is comprised of a heavy chain variable region (abbreviated herein as HCVR or $V_H$) and a heavy chain constant region. The heavy chain constant region is comprised of three domains, $C_H1$, $C_H2$, and $C_H3$. Each light chain is comprised of a light chain variable region (abbreviated herein as LCVR or $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding fragment" of an antibody as used herein, refers to one or more portions of an antibody that retain the ability to specifically bind to an antigen (e.g., glycated Amadori product of CD59). In certain embodiments, the glycated Amadori product of CD59 is K41-glycated Amadori product of CD59. It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody; (v) a dAb fragment (Ward et al., (1989) *Nature* 341:544-546) which consists of a $V_H$ domain; and (vi) an isolated complementarity determining region (CDR). Furthermore, although the two domains of the Fv fragment, V and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional procedures, such as proteolytic fragmentation procedures, as described in J. Goding, Monoclonal Antibodies: Principles and Practice, pp 98-118 (N.Y. Academic Press 1983), which is hereby incorporated by reference as well as by other techniques known to those of skill in the art. The fragments are screened for utility in the same manner as are intact antibodies.

As used herein, "specific binding" refers to antibody binding to a predetermined antigen with a preference that enables the antibody to be used to distinguish the antigen from others to an extent that permits the diagnostic assays described herein. Specific binding to glycated Amadori product of CD59 means that the antibody not only preferentially binds CD59 versus other proteins, but also that it preferentially binds a glycated Amadori product of CD59 molecule versus one that is not glycated. In certain embodiments, the antibody binds with an affinity that is at least two-fold greater than its affinity for binding to antigens other than the predetermined antigen. In certain embodiments, the antibody binds with an affinity that is at least five-fold greater than its affinity for binding to antigens other than the predetermined antigen. In one embodiment, the antibody binds with an affinity that is at least one order of magnitude greater than its affinity for binding to antigens other than the predetermined antigen. In certain embodiments, the antibody binds with an affinity that is at least two orders of magnitude greater than its affinity for binding to antigens other than the predetermined antigen. In certain embodiments, the antibody binds with an affinity that is at least two orders of magnitude greater than its affinity for binding to antigens other than the predetermined antigen. In one embodiment, the antibody binds with an affinity that is at least four orders of magnitude greater than its affinity for binding to antigens other than the predetermined antigen. In certain embodiments, an antibody or antigen-binding fragment of the invention specifically binds to a K41-glycated Amadori product of CD59 and in other embodiments, an antibody of the invention or antigen-binding fragment thereof specifically binds to a CD59 that is glycated at lysine residue that does not correspond to K41 of CD59.

The isolated antibodies of the invention encompass various antibody isotypes, such as IgG1, IgG2, IgG3, IgG4, IgM, IgA1, IgA2, IgAsec, IgD, and IgE. As used herein, "isotype" refers to the antibody class (e.g. IgM or IgG1) that is encoded by heavy chain constant region genes. The antibodies can be full length or can include only an antigen-binding fragment such as the antibody constant and/or variable domain of IgG1, IgG2, IgG3, IgG4, IgM, IgA1, IgA2, IgAsec, IgD or IgE or could consist of a Fab fragment, a F(ab')$_2$ fragment, and a Fv fragment.

The antibodies of the present invention can be polyclonal, monoclonal, or a mixture of polyclonal and monoclonal antibodies. The antibodies can be produced by a variety of techniques well known in the art. In certain embodiments, the epitope recognized by a monoclonal antibody of the invention includes glycated lysine that corresponds to the K41 in mature CD59. In certain embodiments, the epitope recognized by a monoclonal antibody of the invention includes the sequence WKFEH (SEQ ID NO:1).

Monoclonal antibody production may be effected by techniques that are known in the art. The term "monoclonal antibody," as used herein, refers to a preparation of antibody molecules of a single molecular composition. A monoclonal antibody displays a single binding specificity and affinity for a particular epitope. The process of monoclonal antibody production involves obtaining immune somatic cells with the potential for producing antibody, in particular B lymphocytes, which have been previously immunized with the antigen of interest either in vivo or in vitro and that are suitable for fusion with a B-cell myeloma line.

Mammalian lymphocytes typically are immunized by in vivo immunization of the animal (e.g., a mouse) with the desired protein or polypeptide, e.g., with glycated Amadori product of CD59 or a fragment thereof, or K41-glycated Amadori product of CD59 or a fragment thereof in the present invention. In certain embodiments, the polypeptide is a modified polypeptide as described herein. In certain embodiments, the polypeptide comprises the sequence set forth as SEQ ID NO:1. Such immunizations are repeated as necessary at intervals of up to several weeks to obtain a sufficient titer of antibodies. Once immunized, animals can be used as a source of antibody-producing lymphocytes. Following the last antigen boost, the animals are sacrificed and spleen cells removed. Mouse lymphocytes give a higher percentage of stable fusions with the mouse myeloma lines described herein. Of these, the BALB/c mouse is preferred. However, other mouse strains, rabbit, hamster, sheep, and frog may also be used as hosts for preparing antibody-producing cells. See Goding (in *Monoclonal Antibodies: Principles and Practice,* 2d ed., pp. 60-61, Orlando, Fla., Academic Press, 1986). Mouse strains that have human immunoglobulin genes inserted in the genome (and which cannot produce mouse immunoglobulins) can also be used. Examples include the HUMAB MOUSE® strains produced by Medarex/GenPharm International, and the XENOMOUSE® strains produced by Abgenix. Such mice produce fully human immunoglobulin molecules in response to immunization.

Those antibody-producing cells that are in the dividing plasmablast stage fuse preferentially. Somatic cells may be obtained from the lymph nodes, spleens, and peripheral blood of antigen-primed animals, and the lymphatic cells of choice depend to a large extent on their empirical usefulness in the particular fusion system. The antibody-secreting lymphocytes are then fused with (mouse) B cell myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature* 256:495 (1975), which is hereby incorporated by reference.

Myeloma cell lines suited for use in hybridoma-producing fusion procedures preferably are non-antibody-producing, have high fusion efficiency, and enzyme deficiencies that render them incapable of growing in certain selective media which support the growth of the desired hybridomas. Examples of such myeloma cell lines that may be used for the production of fused cell lines include Ag8, P3-X63/Ag8, X63-Ag8.653, NS1/1.Ag 4.1, Sp2/0-Ag14, FO, NSO/U, MPC-11, MPC11-X45-GTG 1.7, 5194/5XX0 Bul, all derived from mice; R210.RCY3, Y3-Ag 1.2.3, IR983F and 4B210 derived from rats and U-266, GM1500-GRG2, LICR-LON-HMy2, UC729-6, all derived from humans (Goding, in *Monoclonal Antibodies: Principles and Practice,* 2d ed., pp. 65-66, Orlando, Fla., Academic Press, 1986; Campbell, in *Monoclonal Antibody Technology, Laboratory Techniques in Biochemistry and Molecular Biology,* vol. 13, Burden and Von Knippenberg, eds., pp. 75-83, Amsterdam, Elsevier, 1984).

Fusion with mammalian myeloma cells or other fusion partners capable of replicating indefinitely in cell culture is effected by standard and well-known techniques, for example, by using polyethylene glycol ("PEG") or other fusing agents (See Milstein and Kohler, *Eur. J. Immunol.* 6:511 (1976), which is hereby incorporated by reference).

Procedures for raising polyclonal antibodies are well known to those of ordinary skill in the art. For example anti-glycated Amadori product of CD59 polyclonal antibodies may be raised by administering glycated Amadori product of CD59 protein subcutaneously to New Zealand white rabbits which have first been bled to obtain pre-immune serum. The glycated Amadori product of CD59 can be injected at a total volume of 100 μL per site at six different sites, typically with one or more adjustments. The rabbits are then bled two weeks after the first injection and periodically boosted with the same antigen three times every six weeks. A sample of serum is collected 10 days after each boost. Polyclonal antibodies are recovered from the serum, preferably by affinity chromatography using glycated Amadori product of CD59 to capture the antibody. This and other procedures for raising polyclonal antibodies are disclosed in E. Harlow, et al., editors, Antibodies: A Laboratory Manual (1988), which is hereby incorporated by reference. In certain embodiments, the epitope recognized by the polyclonal antibody includes glycated lysine that corresponds to the K41 in mature CD59. In certain embodiments, the epitope recognized by the polyclonal antibody includes WKFEH (SEQ ID NO:1).

In other embodiments, the antibodies can be recombinant antibodies. The term "recombinant antibody", as used herein, is intended to include antibodies that are prepared, expressed, created or isolated by recombinant means, such as antibodies isolated from an animal (e.g., a mouse) that is transgenic for another species' immunoglobulin genes, antibodies expressed using a recombinant expression vector transfected into a host cell, antibodies isolated from a recombinant, combinatorial antibody library, or antibodies prepared, expressed, created or isolated by any other means that involves splicing of immunoglobulin gene sequences to other DNA sequences.

The present invention further provides nucleic acid molecules encoding anti-glycated Amadori product of CD59 antibodies (e.g., anti-K41-glycated Amadori product of CD59 antibodies) and vectors comprising the nucleic acid molecules as described herein. The vectors provided can be used to transform or transfect host cells for producing anti-glycated Amadori product of CD59 antibodies with the specificity of antibodies described herein. In one embodiment, the vectors can comprise an isolated nucleic acid molecule encoding a heavy chain and/or a light chain of an antibody of the invention encoded by a nucleic acid molecule. In a further embodiment, plasmids are given which produce the antibodies or antigen-binding fragments described herein.

In certain aspects of the invention, the antibody or antigen-binding fragment thereof binds to a conformational epitope within the glycated Amadori product of CD59 molecule. To determine if the selected anti-glycated Amadori product of CD59 antibodies bind to conformational epitopes, each antibody can be tested in assays using native protein (e.g., non-denaturing immunoprecipitation, flow cytometric analysis of cell surface binding) and denatured protein (e.g., Western blot, immunoprecipitation of denatured proteins). A comparison of the results will indicate whether the antibodies bind conformational epitopes. Antibodies that bind to native protein but not denatured protein are those antibodies that bind conformational epitopes.

In certain embodiments, antibodies of the invention competitively inhibit the specific binding of a second antibody to its target glycated epitope on glycated Amadori product of CD59. In certain embodiments, the target epitope includes the sequence set forth as WKFEH (SEQ ID NO:1), which is glycated. To determine competitive inhibition, a variety of assays known to one of ordinary skill in the art can be employed. For example, competition assays can be used to determine if an antibody competitively inhibits binding to glycated Amadori product of CD59 (or K41-glycated Amadori product of CD59) by another antibody. These methods may include cell-based methods employing flow cytometry or solid phase binding analysis. Other assays that evaluate the ability of antibodies to cross-compete for glycated Amadori product of CD59 (or K41-glycated Amadori product of CD59) molecules in solid phase or in solution phase, also can be used.

Certain antibodies competitively inhibit the specific binding of a second antibody to its target epitope on glycated Amadori product of CD59 (or K41-glycated Amadori product of CD59) by at least about 10%, 20%, 30%, 40%, 50%, 60%, 70%, 80%, 90%, 95%, or 99%. Inhibition can be assessed at various molar ratios or mass ratios; for example competitive binding experiments can be conducted with a 2-fold, 3-fold, 4-fold, 5-fold, 7-fold, 10-fold or more molar excess of the first antibody over the second antibody.

Other antibodies include antibodies that specifically bind to an epitope on glycated Amadori product of CD59 defined by a second antibody. To determine the epitope, one can use standard epitope mapping methods known in the art. For example, fragments (peptides) of K41-glycated Amadori product of CD59 antigen (preferably synthetic peptides) that bind the second antibody can be used to determine whether a candidate antibody binds the same epitope. In certain embodiments, the epitope is WKFEH (SEQ ID NO:1), which includes the glycated K that corresponds to K41 of mature CD59. For linear epitopes, overlapping peptides of a defined length (e.g., 8 or more amino acids) are synthesized. The peptides preferably are offset by 1 amino acid, such that a series of peptides covering every 8 amino acid fragment of the glycated Amadori product of CD59 protein sequence are prepared. Fewer peptides can be prepared by using larger offsets, e.g., 2 or 3 amino acids. In addition, longer peptides (e.g., 9-, 10- or 11-mers) can be synthesized. Binding of peptides to antibodies can be determined using standard methodologies including surface plasmon resonance (BIA-CORE) and ELISA assays. For examination of conformational epitopes, larger glycated Amadori product of CD59 fragments, including in certain embodiments, K41-glycated Amadori product of CD59, can be used. Other methods that use mass spectrometry to define conformational epitopes have been described and can be used (see, e.g., Baerga-Ortiz et al., *Protein Science* 11:1300-1308, 2002 and references cited therein). Still other methods for epitope determination are provided in standard laboratory reference works, such as Unit 6.8 ("Phage Display Selection and Analysis of B-cell Epitopes") and Unit 9.8 ("Identification of Antigenic Determinants Using Synthetic Peptide Combinatorial Libraries") of *Current Protocols in Immunology*, Coligan et al., eds., John Wiley & Sons. Epitopes can be confirmed by introducing point mutations or deletions into a known epitope, and then testing binding with one or more antibodies to determine which mutations reduce binding of the antibodies.

An antibody or antigen-binding fragment of the invention can be linked to a detectable label. Detectable labels useful in the invention include, but are not limited to fluorescent labels, enzyme labels, radioactive labels, nuclear magnetic resonance active labels, phosphorescent labels, luminescent labels, and chromophore labels. The detectable labels of the invention can be attached to the antibodies or antigen-binding fragments thereof by standard protocols known in the art. In certain embodiments, the detectible labels may be covalently attached to an anti-CD59 antibody or antigen-binding fragment of the invention. The covalent binding can be achieved either by direct condensation of existing side chains or by the incorporation of external bridging molecules. Many bivalent or polyvalent agents are useful in coupling protein molecules to other proteins, peptides or amine functions, etc. For example, the literature is replete with coupling agents such as carbodiimides, diisocyanates, glutaraldehyde, diazobenzenes, and hexamethylene diamines. This list is not intended to be exhaustive of the various coupling agents known in the art but, rather, is exemplary of the more common coupling agents.

In certain embodiments, it is contemplated that one may wish to first derivatize the antibody, and then attach the detectible label to the derivatized product. Suitable cross-linking agents for use in this manner include, for example, SPDP (N-succinimidyl-3-(2-pyridyldithio)propionate), and SMPT, 4-succinimidyl-oxycarbonyl-methyl-(2-pyridyldithio)toluene. In certain embodiments, a radionuclide may be coupled to an antibody or antigen-binding fragment thereof by chelation.

Uses

The compositions (e.g., antibodies to glycated Amadori product of CD59 and CD59 fragments) of the present invention have diagnostic and therapeutic utilities. For example, these molecules can be contacted with a sample obtained from a subject to diagnose a variety of disorders. As detailed herein, the antibodies or antigen-binding fragments of the invention may be used for example to isolate and identify CD59 protein and/or glycated (Amadori product) and/or nonglycated CD59 protein. The antibodies may be coupled to specific diagnostic labeling agents for imaging of the protein or fragment thereof. The antibodies or antigen-binding fragments of the invention may also be used for immunoprecipitation, immunoblotting CD59 and/or glycated Amadori product of CD59 using standard methods known to those of ordinary skill in the art.

The invention in certain aspects includes various assays to determine the levels of glycated Amadori product of CD59. The methods of the invention that are useful to determine levels of glycated Amadori product of CD59 in cells, tissues, and samples from subjects, include, but are not limited to, binding assays; specific binding assays, such as using antibodies or antigen-binding fragments of the invention that bind specifically to glycated Amadori product of CD59; gel electrophoresis; mass spectrometry; NMR; and the like. Immunoassays may be used according to the invention including sandwich-type assays, competitive binding assays, one-step direct tests and two-step tests.

The methods and assays of the invention (e.g. binding assays, gel electrophoresis; mass spectrometry; NMR; and the like) may be used to monitor exposure to blood glucose levels in a subject over time. Thus, the methods of the invention may be used to examine changes in glycated Amadori product of CD59 levels in a subject over time. This allows monitoring of glycated Amadori product of CD59 levels in a subject who is believed to be at risk of developing a diabetic condition and also enables monitoring in a subject who is known to have a diabetic condition. Thus, the methods of the invention may be used to assess the efficacy of a therapeutic treatment of a diabetic condition by the assessment of the level of glycated Amadori product of CD59 in a subject at various time points. For example, a level of a subject's glycated Amadori product of CD59 can be obtained prior to the start of a therapeutic regimen (either prophylactic or as a treatment of an existing diabetic condition), during the treatment regimen, and/or after a treatment regimen, thus providing information on the effectiveness of the regimen in the patient.

It will be understood that a therapeutic regimen may be either prophylactic or a treatment of an existing diabetic condition in a subject. Thus, the methods of the invention may be used to monitor a subject's response to prophylactic therapy and/or treatment for a diabetic condition provided to a subject. Thus, the methods of the invention (e.g. binding assays, gel electrophoresis; mass spectrometry; NMR; and the like) may also be useful to monitor the progression or regression of a diabetic condition in a subject. The level of glycated Amadori product of CD59 may be determined in two, three, four, or more samples obtained from a subject over time. The level of glycated Amadori product of CD59 in the samples may be compared and changes in the levels over time may be used to assess glycemic control in the subject.

One aspect of the present invention relates to the use of the antibodies and/or antigen-binding fragments of the invention for detecting glycated Amadori product of CD59 proteins or portions thereof in a biological sample (e.g., histological or cytological specimens, body fluid samples, biopsies and the like), and, in particular, to distinguish the level of glycated Amadori product of CD59 from the level of non-glycated Amadori product of CD59 in a sample or a subject. This method involves providing an antibody or an antigen-binding binding fragment thereof, which specifically binds to glycated Amadori product of CD59 or other anti-glycated Amadori product of CD59 antibody. The anti-CD59 antibody may be bound to a label that permits the detection of the glycated Amadori product of CD59. The biological sample is contacted with the labeled anti-glycated Amadori product of CD59 antibody under conditions effective to permit binding of the anti-glycated Amadori product of CD59 antibody to glycated Amadori product of CD59 in the sample. The presence of glycated Amadori product of CD59 in the biological sample is detected by detection of the label. In certain embodiments, the contact between the anti-glycated Amadori product of CD59 antibody and the biological sample is carried out in samples from a subject. Samples to which the methods of the invention can be applied include tissue and body fluid samples.

In yet another aspect, the invention provides a method for diagnosing or monitoring the progression of a diabetic condition comprising: obtaining a sample from a human subject; contacting the sample with an antibody or antibody fragment of the invention; and determining the amount of glycated Amadori product of CD59 present in the sample.

In certain embodiments, the invention provides the method wherein the steps of obtaining, contacting, and determining are repeated on one or more occasions. In further embodiments, the invention provides the method wherein the contacting is performed in a reaction chamber and wherein the antibody, antibody fragment, glycated Amadori product of CD59, or glycated Amadori product of a fragment of CD59 is immobilized on a solid support. In certain embodiments, the invention provides the method wherein the antibody or antibody fragment is labeled. In further embodiments, the invention provides the method performed in conjunction with a therapeutic treatment regime comprising an anti-diabetic agent. In certain embodiments, the invention provides the method wherein the anti-diabetic agent is selected from the group consisting of insulin, an insulin analog, nateglinide, repaglinide, metformin, thiazolinediones, glitazones such as troglitazone, pioglitazone and rosiglitazone, glisoxepid, glyburide, glibenclamide, acetohexamide, chloropropamide, glibornuride, tolbutamide, tolazamide, glipizide, carbutamide, gliquidone, glyhexamide, phenbutamide, tolcyclamide, glimepiride, and gliclazide.

Thus, the anti-glycated Amadori product of CD59 antibodies of the present invention can be used in immunofluorescence techniques to examine human tissue, cell and bodily fluid specimens. In certain embodiments, the samples are fresh samples. In certain embodiments, slides containing cryostat sections of frozen, unfixed tissue biopsy samples or cytological smears are air dried, formalin or acetone fixed, and incubated with the monoclonal antibody preparation in a humidified chamber at room temperature. The slides are then washed and further incubated with a preparation of a secondary antibody directed against the monoclonal antibody, usually some type of anti-mouse immunoglobulin if the monoclonal antibodies used are derived from the fusion of a mouse spleen lymphocyte and a mouse myeloma cell line. This secondary antibody is tagged with a compound, for instance rhodamine or fluorescein isothiocyanate, that fluoresces at a particular wavelength. The staining pattern and intensities within the sample are then determined by fluorescent light microscopy and optionally photographically recorded.

As yet another alternative, computer enhanced fluorescence image analysis or flow cytometry can be used to examine tissue specimens or cells using the anti-glycated Amadori product of CD59 antibodies of the invention. The anti-glycated Amadori product of CD59 antibodies of the invention are particularly useful in assessing samples obtained from subjects which can be evaluated using a fluorescence image analyzer or with a flow cytometer.

The antibodies and/or antigen-binding fragments of the present invention can be used to screen patients for diseases associated with the presence of elevated levels of glycated Amadori product of CD59. As used herein, the term "elevated" means higher, for example elevated versus a control level. In addition, the antibodies of the invention can be used to identify the recurrence of such diseases. The antibodies of the invention are particularly useful in assays to differentiate whether or not a subject has a diabetic condition, because the glycated Amadori product of CD59 protein to which the anti-glycated Amadori product of CD59 antibodies bind is present in increased amounts in tissues and body fluids of subjects who have a diabetic condition. The percent of glycated Amadori product of CD59 in a sample can be used to determine the presence and/or status of a diabetic condition. The antibodies of the invention can be used to obtain useful prognostic information by providing an early indicator of disease onset or progression.

In certain embodiments of the invention, an assessment of glycated CD59 in a subject can be determined from a comparison of the levels of glycated CD59 in a subject relative to such levels of glycated CD59 in a normal individual. In one embodiment of the invention, an assessment of glycated CD59 in a subject can be determined from a comparison of the levels of glycated CD59 in a subject relative to total CD59 in a subject. In certain embodiments of the invention, an assessment of glycated CD59 in a subject can be determined from a comparison of the levels of glycated CD59 in a subject relative to non-glycated CD59 in a subject.

In certain embodiments of the invention, the antibodies of the present invention can be used in combination with other known antibodies to provide additional information regarding the level of glycated Amadori product of CD59 as a percentage of the level of total CD59 in a sample. For example, an antibody that binds CD59 (glycated and non-glycated) can be used to determine the total amount or level of CD59 in a sample, can be used in conjunction with an antibody of the invention that specifically binds a glycated Amadori product of CD59 to determine a percentage of total CD59 in a sample that is the glycated Amadori product of CD59.

The step of contacting an antibody or antigen-binding fragment of the invention with a sample to be tested can be carried out in a sample of saliva, urine, serum or other body fluids, to detect the presence of glycated Amadori product of CD59 in the body fluid. When the contacting is carried out in a saliva, urine, or serum sample, it is preferred that the antibody or antigen-binding fragment of the invention recognize substantially no antigens in the sample other than glycated Amadori product of CD59. In certain embodiments, it is preferred that the antibody or antigen-binding fragment of the invention recognize substantially no antigens in the sample other than K41-glycated Amadori product of CD59.

Antibodies and antigen-binding fragments thereof suitable for detecting glycated Amadori product of CD59 include anti-glycated Amadori product of CD59 antibodies, such as monoclonal or polyclonal antibodies. In addition, antibody fragments, half-antibodies, hybrid derivatives, probes, and other molecular constructs may be utilized. In certain embodiments, the antibodies are anti-K41-glycated Amadori product of CD59 antibodies.

The antibodies or antigen-binding fragments of the invention may also be used in a variety of assays based upon detecting levels of glycated Amadori product of CD59 in subjects. The assays include (1) characterizing the impact of blood sugar levels on glycation levels in a subject; (2) evaluating a treatment for regulating blood sugar levels in a subject; (3) selecting a treatment for regulating blood sugar levels in a subject; and (4) determining progression, progression or onset of a condition characterized by abnormal levels of glycated protein in a subject. Thus, subjects can be characterized, treatment regimens can be monitored, treatments can be selected and diseases can be better understood using the assays of the present invention. For example, the antibodies or antigen-binding fragments of the invention are useful in one aspect in methods for measuring the level of glycated Amadori product of CD59 in a subject, which is a direct indicator of the short-term (1-2 weeks) averaged level of the subject's glycemic control. The impact of blood sugar levels or glycation levels thus can be measured due to the positive correlation between the short term averaged level of circulating blood glucose and the amount of glycation of endogenous CD59. The level of glycated Amadori product of CD59 thus correlates with the short term averaged level of glycemic control in the subject. Relatively low levels of glycated Amadori product of CD59 reflect well-controlled circulating blood sugar levels and selectively high levels of glycated Amadori product of CD59 reflect poorly controlled glycemic levels.

The antibodies or antigen-binding fragments of the invention may be used in assays described herein, which are carried out on samples obtained from subjects. As used herein, a subject is a human, non-human primate, cow, horse, pig, sheep, goat, dog, cat, or rodent. In all embodiments, human subjects are preferred. The samples used herein are any body tissue or body fluid sample obtained from a subject. Preferred are body fluids, for example, lymph, saliva, blood, urine, and the like. Saliva and urine are preferred, blood being most preferred. It has been surprisingly discovered that glycated Amadori product of CD59 can be detected in saliva and urine, thereby obviating the need for a blood sample.

Particularly, important subjects to which the present invention can be applied are diabetic subjects. The term "diabetic" as used herein, means an individual who, at the time the sample is taken, has a primary deficiency of insulin and/or an abnormal (e.g., reduced) ability to metabolize glucose as compared with a normal subject, including conditions such as impaired glucose tolerance or impaired fasting glucose, generally termed "pre-diabetes". Thus, diabetics suffer from a disease in which the levels of blood glucose, also called blood sugar, are above normal. The term diabetic includes, but is not limited to, individuals with juvenile pre-diabetes and diabetes (Type 1 diabetes), adult-onset pre-diabetes and diabetes (Type 2 diabetes), gestational pre-diabetes and diabetes, and any other conditions of insulin deficiency or reduction in the ability to metabolize glucose. The terms "diabetic" and "pre-diabetic" are terms of art, known and understood by those practicing in the medical profession, a formal definition of which can be found in *Harrison's Principles of Medicine* (Harrisons, Vol. 14, *Principles of Internal Medicine*, Eds. Fauci, A. S., E. Braunwald, K. J. Isselbacher, J. D. Wilson, J. B. Martin, D. L. Kasper, S. L. Hauser, D. L. Longo, McGraw-Hill, New York, 1999).

All of the assays described herein may include the use of the antibodies or antigen-binding fragments of the invention and involve measuring levels of glycated Amadori product of CD59. Levels of glycated Amadori product of CD59 can be determined in a number of ways when carrying out the various methods of the invention. In one particularly important measurement, the level of glycated Amadori product of CD59 is measured in relation to nonglycated Amadori product of CD59. Thus, the measurement is a relative measure, which can be expressed, for example, as a percentage of total CD59. Another measurement of the level of glycated Amadori product of CD59 is a measurement of absolute levels of glycated Amadori product of CD59. This could be expressed, for example, in terms of grams per liter of body fluid. Another measurement of the level of glycated Amadori product of CD59 is a measurement of the change in the level of glycated Amadori product of CD59 over time. This may be expressed in an absolute amount or may be expressed in terms of a percentage increase or decrease over time. The antibodies or antigen-binding fragments of the invention may be used in diagnostic methods alone or in conjunction with certain antibodies already known in the art. The known antibodies may include anti-CD59 antibodies as well as anti-glycation-moiety antibodies, for example, Anti-CD-59 YTH53.1, and the anti-hexitol-lysine antibody, which binds to non-reduced and reduced glycated Amadori product of CD59, respectively.

Importantly, levels of glycated Amadori product of CD59 can be determined using the antibodies or antigen-binding fragments of the invention and are advantageously compared to controls according to the invention. The control may be a predetermined value, which can take a variety of forms. It can be a single cut-off value, such as a median or mean. It can be established based upon comparative groups, such as in groups having normal amounts of circulating insulin and groups having abnormal amounts of circulating insulin. Another example of comparative groups would be groups having a particular disease, condition or symptoms and groups without the disease, condition or symptoms. Another comparative group would be a group with a family history of a condition and a group without such a family history. The predetermined value can be arranged, for example, where a tested population is divided equally (or unequally) into groups, such as a low-risk group, a medium-risk group and a high-risk group or into quandrants or quintiles, the lowest quandrant or quintile being individuals with the lowest risk or amounts of glycated protein and the highest quandrant or quintile being individuals with the highest risk or amounts of glycated protein.

The predetermined value, of course, will depend upon the particular population selected. For example, an apparently healthy population will have a different 'normal' range than will a population which is known to have a condition related to abnormal protein glycation. Accordingly, the predetermined value selected may take into account the category in which an individual falls. Appropriate ranges and categories can be selected with no more than routine experimentation by those of ordinary skill in the art. As used herein, "abnormal" means not normal as compared to a control. By abnormally high it is meant high relative to a selected control. Typically the control will be based on apparently healthy normal individuals in an appropriate age bracket.

In measuring the relative amount of glycated Amadori product of CD59 to nonglycated Amadori product of CD59, those of ordinary skill in the art will appreciate that the relative amount may be determined by measuring either the relative amount of glycated Amadori product of CD59 or the relative amount of nonglycated Amadori product of CD59. In other words, if 90% of an individual's CD59 is nonglycated Amadori product of CD59, then 10% of the individual's CD59 will be glycated Amadori product of CD59. Thus, measuring the level of glycated Amadori product of CD59 may be carried out using an antibody or antigen-binding fragment of the invention in methods to measure the relative amount of nonglycated Amadori product of CD59.

It will also be understood that the controls according to the invention may be, in addition to predetermined values, samples of materials tested in parallel with the experimental materials. Examples include samples from control populations or control samples generated through manufacture to be tested in parallel with the experimental samples.

The invention includes various assays used to determine the levels of glycated Amadori product of CD59 and include: binding assays; specific binding assays, such as using antibodies or antigen-binding fragments of the invention that bind specifically to glycated Amadori product of CD59; gel electrophoresis; mass spectrometry; NMR; and the like. Immunoassays may be used according to the invention including sandwich-type assays, competitive binding assays, one-step direct tests and two-step tests.

As mentioned above, it is also possible to use the antibodies or antigen-binding fragments of the invention to characterize averaged short-term blood sugar levels by monitoring changes in the absolute or relative amounts of glycated Amadori product of CD59 over time. For example, it is expected that an increase in glycated Amadori product of CD59 correlates with increasing dysregulation of glycemic levels. Accordingly one can monitor glycated Amadori product of CD59 levels over time to determine if glycemic levels of a subject are changing. Changes in relative or absolute glycated Amadori product of CD59 of greater than 0.1% may indicate an abnormality. Preferably, the change in glycated Amadori product of CD59 levels, which indicates an abnormality, is greater than 0.2%, greater than 0.5%, greater than 1.0%, 2.0%, 3.0%, 4.0%, 5.0%, 7.0%, 10%, 15%, 20%, 25%, 30%, 40%, 50%, or more. Reductions in amounts of glycated Amadori product of CD59 over time may indicate improved glycemic control.

The antibodies or antigen-binding fragments of the invention may also be used in diagnostic methods to determine the effectiveness of treatments for abnormal glycemic levels. The "evaluation of treatment" as used herein, means the comparison of a subject's levels of glycated Amadori product of CD59 measured in samples collected from the subject at different sample times, preferably at least one-two weeks apart. The preferred time to obtain the second sample from the subject is at least one week after obtaining the first sample, which means the second sample is obtained at any time following the day of the first sample collection, preferably at least 12, 18, 24, 36 or more days after the time of first sample collection.

The antibodies or antigen-binding fragments of the invention may be used to allow the comparison of levels of glycated Amadori product of CD59 in two or more samples, taken on different weeks, which is a measure of level of the subject's glycemic control and allows evaluation of the treatment to regulate blood sugar levels. The comparison of a subject's levels of glycated Amadori product of CD59 measured in samples obtained on different weeks provides a measure of glycemic control to determine the effectiveness of any treatment to regulate blood sugar levels.

As will be appreciated by those of ordinary skill in the art, the evaluation of the treatment also may be based upon an evaluation of the symptoms or clinical end-points of the associated disease, such as the vascular complications of pre-diabetes and diabetes. Thus, the antibodies or antigen-binding fragments of the invention are useful for determining the regression, progression or onset of a condition which is characterized by abnormal levels of glycated protein, including those characterized by abnormal levels of glycated Amadori product of CD59. In some instances, the antibodies or antigen-binding fragments of the invention can be used to test glycemic control in subjects to which the methods of the invention are applied are already diagnosed as having a particular condition or disease. In other instances, the antibodies or antigen-binding fragments of the invention can be used to obtain measurements that represent the diagnosis of the condition or disease. In some instances, the subjects will already be undergoing drug therapy for regulating blood sugar levels, while in other instances the subjects will be without present drug therapy for regulating blood sugar levels.

According to still another aspect of the invention, the antibodies or antigen-binding fragments of the invention can be used in methods for treating a subject to reduce the risk of a disorder associated with abnormally-high levels of glycated Amadori product of CD59. The method involves selecting and administering to a subject who is known to have an abnormally-high level of glycated Amadori product of CD59, an agent for treating the disorder. Preferably, the agent is an agent for reducing glycated Amadori product of CD59 levels and is administered in an amount effective to reduce glycated Amadori product of CD59 levels.

In this aspect of the invention, the treatments are based upon selecting subjects who have unwanted, elevated levels of glycated Amadori product of CD59, which can be done using the antibodies or antigen-binding fragments of the invention. Such subjects may already be receiving a drug for regulating blood sugar levels, but, according to the invention, are now candidates for an elevated level of the drug based upon the presence of the elevated levels of glycated Amadori product of CD59. It may be appropriate according to the invention to alter a therapeutic regimen for a subject, based upon the measurement of the level of glycated Amadori product of CD59. This can be understood in connection with treatment of diabetics. Diabetics are treated in at least three different ways. Some diabetics are treated only with non-drug therapy, such as exercise and diet. Other diabetics are treated with oral drug therapy, but not with insulin which is injected. Finally, some diabetics are treated with insulin or analogs of insulin by injection. According to the present invention, as a result of determining an elevated level of glycated Amadori product of CD59, an individual undergoing only non-drug therapy may be a candidate for drug therapy as a result of the glycated Amadori product of CD59 test. Likewise, a subject receiving only oral drug therapy, may be a candidate for an insulin-based injectable therapy, due to testing with the antibodies or antigen-binding fragments of the invention to determine levels of glycated Amadori product of CD59. Finally, a subject may be free of any present treatment but may be a candidate for blood sugar level regulating treatment as a result of the use of the antibodies or antigen-binding fragments of the invention in a test for glycated Amadori product of CD59. Thus, subjects may be selected and treated with elevated levels of the same drugs or with different therapies as a result of assays that utilize the antibodies or antigen-binding fragments of the invention.

According to the present invention, some of the subjects are free of symptoms otherwise calling for treatment with a particular therapy. This means that absent the use of the antibodies or antigen-binding fragments of the invention to assess glycated Amadori product of CD59, the subject would not according to convention as of the date of the filing of the present application have symptoms calling for treatment with a particular therapy. It is only as a result of the measuring the level of glycated Amadori product of CD59 that the subject becomes a candidate for treatment with the therapy.

Drug therapies for regulating blood sugar levels include oral therapies with hypoglycemic agents an/oral anti-diabetic agents, injectable therapies, and the like. Non-drug therapies for regulating blood sugar level include, but are not limited to, dietetic and/or exercise control measures. Diet and exercise alterations include, but are not limited to, reducing caloric intake, and/or increasing fiber intake, and/or decreasing fat intake, and/or increasing exercise level.

Oral drug therapies for regulating blood sugar levels include hypoglycemic agents that may include, but are not limited to: Acarbose; Acetohexamide; Chlorpropamide; Darglitazone Sodium: Glimepiride; Glipizide; Glyburide, Repaglinide; Troglitazone; Tolazamide; Tolbutamide.

Oral drug therapies for regulating blood sugar levels include antidiabetic agents that may include but are not limited to: Acarbose, Acetohexamide; Buformin; Butoxamine Hydrochloride; Camiglibose; Chlorpropamide; Ciglitazone; Englitazone Sodium; Etoformin Hydrochloride; Gliamilide; Glibornuride; Glicetanile Gliclazide Sodium; Gliflumide; Glipizide; Glucagon; Glyburide; Glyhexamide; Glymidine Sodium; Glyoctamide; Glyparamide; Insulin; Insulin, Dalanated; Insulin Human; Insulin Human, Isophane; Insulin Human Zinc; Insulin Human Zinc, Extended; Insulin, Isophane; Insulin Lispro; Insulin, Neutral; Insulin Zinc; Insulin Zinc, Extended; Insulin Zinc, Prompt; Linogliride; Linogliride Fumarate; Metformin; Methyl Palmoxirate; Palmoxirate Sodium; Pioglitazone Hydrochloride; Pirogliride Tartrate; Proinsulin Human; Repaglinide; Seglitide Acetate; Tolazamide; Tolbutamide; Tolpyrramide; Troglitazone; and Zopolrestat.

Injectable therapies for regulating blood sugar levels include, but are not limited to, Fast-Acting Insulin; Insulin Injection; regular insulin; Prompt Insulin Zinc Suspension; SEMILENTE® insulin. These categories include preparations such as: HUMALOG® Injection; HUMULIN® R; Iletin II; Novolin R, Purified Pork Regular Insulin; Velosulin BR Human Insulin; Intermediate-acting Insulin: Isophane Insulin Suspension: NPH insulin, isophane insulin; Insulin Zinc Suspension LENTE® Insulin. These categories include preparations such as: HUMULIN® L; HUMULIN® R; HUMULIN® N NPH; ILETIN® II, LENTE®; ILETIN® II, NPH; NOVOLIN® L, NOVOLIN® N, Purified Pork LENTE® insulin; Purified Pork NPH isophane insulin; Intermediate and Rapid-acting Insulin Combinations: Human Insulin Isophane Suspension/Human Insulin Injection. This category includes preparations such as: HUMULIN® 50/50; HUMULIN® 70/30; NOVOLIN® 70/30; Long-acting Insulin: Protamine Zinc Insulin Suspension; Extended Insulin Zinc Suspension. These categories include preparations such as: ULTRALENTE® Insulin, HUMULIN® U.

Reducing the risk of a disorder associated with abnormally high levels of glycated Amadori product of CD59 means using treatments and/or medications to reduce glycated Amadori product of CD59 levels, therein reducing, for example, the subject's risk of vascular complications including but not limited to: diabetic nephropathy, diabetic retinopathy, macro-vascular disease, micro-vascular disease, and diabetic neuropathy.

In a subject determined to have an abnormally high level of glycated Amadori product of CD59, an effective amount is that amount effective to reduce glycated Amadori product of CD59 levels in the subject. A response can, for example, also be measured by determining the physiological effects of the hypoglycemic, antidiabetic, or insulin composition, such as the decrease of disease symptoms following administration of the hypoglycemic, antidiabetic, or insulin. Other assays will be known to one of ordinary skill in the art and can be employed for measuring the level of the response. The amount of a treatment may be varied for example by increasing or decreasing the amount of a therapeutic composition, by changing the therapeutic composition administered, by changing the route of administration, by changing the dosage timing and so on. The effective amount will vary with the particular condition being treated, the age and physical condition of the subject being treated, the severity of the condition, the duration of the treatment, the nature of the concurrent therapy (if any), the specific route of administration, and the like factors within the knowledge and expertise of the health practitioner. For example, an effective amount can depend upon the degree to which an individual has abnormally elevated levels of glycated Amadori product of CD59.

An "effective amount" of a drug therapy is that amount of a hypoglycemic, antidiabetic, or insulin or insulin analog that alone, or together with further doses, produces the desired response, e.g. reduction of glycemic level or glycated Amadori product of CD59 levels.

In the case of treating a particular disease or condition the desired response is inhibiting the progression of the disease or condition. This may involve only slowing the progression of the disease temporarily, although more preferably, it involves halting the progression of the disease permanently. This can be monitored by routine diagnostic methods known to one of ordinary skill in the art for any particular disease. The desired response to treatment of the disease or condition also can be delaying the onset or even preventing the onset of the disease or condition.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the hypoglycemic, antidiabetic, or insulin composition (alone or in combination with other therapeutic agents) be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The pharmaceutical compositions used in the foregoing methods preferably are sterile and contain an effective amount of hypoglycemic, antidiabetic, or insulin for producing the desired response in a unit of weight or volume suitable for administration to a patient.

The doses of hypoglycemic, antidiabetic, or insulin administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

Various modes of administration will be known to one of ordinary skill in the art which effectively deliver the hypoglycemic, antidiabetic, or insulin to a desired tissue, cell or bodily fluid. Preferred methods for administering the hypoglycemic and antidiabetic are oral. The preferred method of administering insulin is by injection. Administration includes: topical, intravenous, oral, intracavity, intrathecal, intrasynovial, buccal, sublingual, intranasal, transdermal, intravitreal, subcutaneous, intramuscular and intradermal administration. The invention is not limited by the particular modes of administration disclosed herein. Standard references in the art (e.g., *Remington's Pharmaceutical Sciences*, 18th edition, 1990) provide modes of administration and formulations for delivery of various pharmaceutical preparations and formulations in pharmaceutical carriers. Other protocols which are useful for the administration of hypoglycemic, antidiabetic, or insulin will be known to one of ordinary skill in the art, in which the dose amount, schedule of administration, sites of administration, mode of administration (e.g., intra-organ) and the like vary from those presented herein.

Administration of hypoglycemic, antidiabetic, or insulin to mammals other than humans, e.g. for testing purposes or veterinary therapeutic purposes, is carried out under substantially the same conditions as described above. It will be understood by one of ordinary skill in the art that this invention is applicable to both human and animal diseases which can be treated by hypoglycemic, antidiabetic or insulin. Thus this invention is intended to be used in husbandry and veterinary medicine as well as in human therapeutics.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. Preferred components of the composition are described above in conjunction with the description of the hypoglycemic, antidiabetic, or insulin compositions of the invention.

A hypoglycemic, antidiabetic, or insulin composition may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the hypoglycemic, antidiabetic, or insulin, and with each other, in a manner such that there is no interaction which would substantially impair the desired pharmaceutical efficacy.

The pharmaceutical compositions may contain suitable buffering agents, as described above, including: acetate, phosphate, citrate, glycine, borate, carbonate, bicarbonate, hydroxide (and other bases) and pharmaceutically acceptable salts of the foregoing compounds.

The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration conveniently comprise hypoglycemic, antidiabetic, or insulin. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, PA.

The application of the invention to a diabetic subject under treatment with an oral blood sugar regulating agent and otherwise free of symptoms calling for any oral blood sugar regulating agent, as used herein means a subject treated with oral blood sugar regulators whose glycemic-control levels appear normal based on standard diagnostic criteria, including but not limited to measurement of glycated hemoglobin levels.

The application of the invention to a diabetic subject under treatment with insulin (including analogs thereof) and otherwise free of symptoms calling for any insulin, as used herein means a subject treated with insulin whose glycemic-control levels appear to be normal based on standard diagnostic criteria, including but not limited to measurement of glycated hemoglobin levels. Dosages of blood sugar regulating agents are well-known to those of ordinary skill in the art and documented in the literature.

The assay mixture comprises a candidate agent. The candidate agent is preferably an antibody, a small organic compound, or a peptide, and accordingly can be selected from combinatorial antibody libraries, combinatorial protein libraries, or small organic molecule libraries. Typically, a plurality of reaction mixtures are run in parallel with different agent concentrations to obtain a different response to the various concentrations. Typically, one of these concentrations serves as a negative control, i.e., at zero concentration of agent or at a concentration of agent below the limits of assay detection.

Candidate agents encompass numerous chemical classes, although typically they are organic compounds, proteins or antibodies (and fragments thereof that bind antigen). In some preferred embodiments, the candidate agents are small organic compounds, i.e., those having a molecular weight of more than 50 yet less than about 2500, preferably less than about 1000 and, more preferably, less than about 500. Candidate agents comprise functional chemical groups necessary for structural interactions with polypeptides and/or nucleic acids, and typically include at least an amine, carbonyl, hydroxyl, or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random or non-random peptides, combinatorial libraries of proteins or antibodies, and the like. Alternatively, libraries of natural compounds in the form of bacterial, fungal, plant, and animal extracts are available or readily produced. Additionally, natural and synthetically produced libraries and compounds can be readily be modified through conventional chemical, physical, and biochemical means. Further, known agents may be subjected to directed or random chemical modifications such as acylation, alkylation, esterification, or amidification to produce structural analogs of the agents.

A variety of other reagents also can be included in the mixture. These include reagents such as salts, buffers, neutral proteins (e.g., albumin), detergents, etc., which may be used to facilitate optimal protein-protein and/or protein-agent binding. Such a reagent may also reduce non-specific or background interactions of the reaction components. Other reagents that improve the efficiency of the assay such as protease inhibitors, nuclease inhibitors, antimicrobial agents, and the like may also be used.

The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours.

After incubation, the presence or absence of and/or the level of glycated Amadori product of CD59 is detected by any convenient method available to the user. For example, the level of glycated Amadori product of CD59 can be determined through the measure of a detectible label. A wide variety of labels can be used, such as those that provide direct detection (e.g., radioactivity, luminescence, optical, or electron density, etc) or indirect detection (e.g., epitope tag such as the FLAG epitope, enzyme tag such as horseradish peroxidase, etc.). The label may be bound to the substrate, or incorporated into the structure of the substrate.

A variety of methods may be used to detect the label, depending on the nature of the label and other assay components. For example, the label may be detected while bound to the substrate or subsequent to separation from the substrate. Labels may be directly detected through optical or electron density, radioactive emissions, nonradiative energy transfers, etc. or indirectly detected with antibody conjugates, streptavidin-biotin conjugates, etc. Methods for detecting a variety of labels are well known in the art.

Kits

Also, within the scope of the invention are kits comprising the compositions of the invention and instructions for use. The kits can further contain at least one additional reagent, such as one or more additional antibodies of the invention.

Kits containing the antibodies or antigen-binding fragments of the invention can be prepared for in vitro diagnosis, prognosis and/or monitoring a diabetic condition or complication by the immunohistological, immunocytological, and immunoserological methods described above. The components of the kits can be packaged either in aqueous medium or in lyophilized form. When the antibodies or antigen-binding fragments thereof are used in the kits in the form of conjugates in which a label moiety is attached, such as an enzyme or a radioactive metal ion, the components of such conjugates can be supplied either in fully conjugated form, in the form of intermediates or as separate moieties to be conjugated by the user or the kit.

A kit may comprise a carrier being compartmentalized to receive in close confinement therein one or more container means or series of container means such as test tubes, vials, flasks, bottles, syringes, or the like. A first of said container means or series of container means may contain one or more anti-glycated Amadori product of CD59 antibodies or antigen-binding fragments thereof or a glycated Amadori product of CD59. A second container means or series of container means may contain a label or linker-label intermediate capable of binding to the primary anti-glycated Amadori product of CD59 antibodies (or fragment thereof).

In certain aspects, the invention provides a kit to determine the amount of glycated Amadori product of CD59 present in the sample comprising the antibody or antibody fragment of the invention and instructions for use. In another aspect, the invention provides a kit for detecting the presence of the glycated Amadori product of CD59 comprising a package including a container containing the isolated antibody or antibody fragment of the invention, and instructions for use of the antibody or antibody fragment to detect the presence of the glycated Amadori product of CD59.

In further embodiments, the invention provides the kit wherein the antibody or antibody fragment is monoclonal. In certain embodiments, the invention provides the kit wherein the antibody or antibody fragment is recombinant. In further embodiments, the invention provides the kit wherein the antibody or antibody fragment is a polyclonal. In certain embodiments, the invention provides the kit wherein the antibody or antibody fragment thereof is attached to a detectible label. In further embodiments, the invention provides the kit wherein the detectible label is selected from the group consisting of a fluorescent label, an enzyme label, a radioactive label, a nuclear magnetic resonance active label, a luminescent label, and a chromophore label. In certain embodiments, the invention provides the kit wherein the antibody or antibody fragment thereof is lyophilized. In further embodiments, the invention provides the kit wherein the antibody or antibody fragment thereof is packaged in an aqueous medium. In certain embodiments, the invention provides the kit further comprising a container containing a second antibody or antibody fragment that specifically binds non-glycated CD59 or non-K41-glycated CD59, and instructions for using the second antibody as a control antibody.

In one aspect, the invention provides a kit comprising a package including a container containing a hybridoma that comprises a nucleic acid sequence that encodes the antibody or antibody fragment of the invention, and instructions for producing the antibody.

These and other aspects of the present invention will be further appreciated upon consideration of the following Examples, which are intended to illustrate certain particular embodiments of the invention but are not intended to limit its scope, as defined by the claims.

EXAMPLES

General Methods

Unless otherwise noted, all the materials were obtained from commercial suppliers and used without further purification. All solvents were commercially available and of polypeptide synthesis grade. Protected amino acids were purchased from Novabiochem. Polypeptide synthesis was performed both manually on an Advanced ChemTech PLS and automatically on a Prelude Protein Technologies synthesizer. Analytical HPLC was performed on a Waters 2695 Alliance chromatograph equipped with a photodiode-array detector and a Waters XBridge C18 column (5 µm/4.6×100 mm), operating at a flow rate of 1 mL/min. Analytical LCMS was performed on a Waters 2695 Alliance chromatograph coupled with a Waters MicromassZQ spectrophotometer and equipped with a UV-VIS detector and a Waters Symmetry C18 column (3.5 µm/2.1×100 mm), operating at a flow rate of 0.5 mL/min and on a Thermo Finnigan Survayor chromatograph coupled with a LCQ Advantage spectrophotometer and equipped with a photodiode-array detector and a Waters XTerra C18 column (3.5 µm/3×100 mm), operating at a flow rate of 1 mL/min. Semi-preparative HPLC was performed on a BioRad BioLogic DuoFlow chromatograph equipped with a UV-VIS detector and a Waters XBridge Prep C18 column (5 µm/10×250 mm), operating at a flow rate of 3 mL/min.

For the purification of the modified amino acids we used a Biotage SP System Flash Chromatograph (RP-FC) equipped with a UV-VIS detector. The solvent system, unless otherwise noted, was always eluent A, 0.1% acetic acid in water, and eluent B, 0.1% acetic acid in MeCN.

Example 1

General Peptide Coupling Procedure $N^{\alpha}$—Ac[Lys41($N^{\epsilon}$-1-deoxyfructosyl)]hCD59(37-50)-OH polypeptide (SEQ ID NO:3) was manually synthesized via stepwise solid-phase polypeptide synthesis from 155 mg of Fmoc-Cys(Trt)-Rink resin starting material (0.41 meq/g, 0.0633 mmol) using PyBOP, HOBt, and DIEA coupling reagents in 5/5/10-fold molar excess. Successive $N^\alpha$-Fmoc protected amino acids were added in a 5-fold molar excess and stirred 2-3 hours at ambient temperature in the dark. Side-chain protecting groups of the $N^\alpha$-Fmoc protected amino acids included: Asn(Trt), Asp(OtBu), Glu(OtBu), His($N^{im}$-Trt), Lys($N^\varepsilon$-Boc) and Trp($N^{in}$-Boc). Synthesis of derivatives of the above polypeptide follow a similar procedure.

The Amadori modification: The Amadori modification of lysine proved successful only when fully protected Amadori building blocks of lysine were used. Thus, the fully protected Amadori building block (1), $N^\alpha$-Fmoc-Lys[$N^\varepsilon$-(2,3:4,5-di-O-isopropylidene-1-deoxyfructosyl, $N^\varepsilon$-Boc)]-OH, was successfully incorporated into polypeptides and also did not hinder the success of subsequent polypeptide coupling reactions. In contrast, partially protected Amadori building blocks of lysine could initially be added to the polypeptide resin but hindered or prevented subsequent polypeptide coupling reactions. Three such partially protected Amadori building blocks of lysine were attempted. One building block had a free secondary $\varepsilon$-NH amino group (2) and the remaining two had unprotected sugar hydroxyls (3 and 4).

Deprotection: Deprotection of the FMOC group was accomplished with 20% piperidine in DMF (v/v), followed by washing with DMF. The N-terminal amino group was acetylated by treating the Na-deprotected peptidyl-resin with $Ac_2O$/DIEA (in 12-fold molar excess) in DMF for 1.5 hours. Simultaneous deprotection of side chains and cleavage of the polypeptide from the resin was incompletely accomplished with a mixture of TFA:anisole:thioanisole: ethandithiol (90:5:3:2, v/v) for 2 hours under $N_2$ atmosphere while shielded from the light. The resulting polypeptide was precipitated by pouring the product solution in cold t-butyl-methyl-ether. The white precipitate was centrifugated and washed several times with cold ether, dissolved in $H_2O$: acetic acid (1:1), and lyophilized. Further deprotection of the isopropylidenes from the lyophilized polypeptide was accomplished in a solution of TFA:$H_2O$:TIS (40:10:1, v/v) for 6 hours (TIS=triisopropylsilane). The resulting solution was diluted with a 15:1 volume of $H_2O$ and lyophilized. The resulting product was still not fully deprotected and exhibited an excess mass of 44 units which seemingly derived from incomplete cleavage of the Boc groups. Complete removal of the isopropylidene protecting groups was accomplished upon treatment with additional TFA (95% TFA, 5% TIS) for 3 hours.

The crude product following the above deprotection reactions was purified by reverse phase semipreparative HPLC with a linear gradient of 10-30% B in A over 30 min, $R_t$=30 min. Crude polypeptide, LC-MS linear gradient of 10-20% B in A over 20 min, intended product $R_t$=9.32 min. Polypeptide after second TFA treatment, LC-MS linear gradient of 10-20% B in A over 10 min, intended product $R_t$=4.97 min. Crude polypeptide analytical HPLC linear gradient of 10-30% B in A over 10 min, $R_t$=5.95 min. The resulting crude polypeptide was purified with an analytical HPLC gradient of 10-30% B in A over 10 min, $R_t$=6.28 min. The pure fractions which resulted were characterized via LCMS using a linear gradient of 10-20% B in A, $R_t$=5.52 min, $[M+H]^+$=1927.2, $[M+H]^{2+}$=964.68 $[M+H]^{3+}$=643.55. 40 mg of pure peptide was recovered (30% yield; >99% pure).

Example 2

Synthesis of fully protected $N^\alpha$-Fmoc-Lys[$N^\varepsilon$-(2,3:4,5-di-O-isopropylidene-1-deoxyfructosyl, $N^\varepsilon$-Boc)]-OH (1)

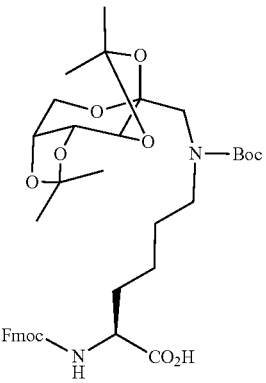

Step 1: Synthesis of $N^\alpha$-Fmoc-Lys[$N^\varepsilon$-(2,3:4,5-di-O-isopropylidene-1-deoxyfructosyl)]-OH (2)

A fresh solution of $NaCNBH_3$ (600 mg, 9.5 mmol) in 5 mL $H_2O$/THF (1:1, v/v) was added to a stirred solution of $N^\alpha$-Fmoc-Lys-OH (1.4 g, 3.8 mmol) and 2,3:4,5-di-O-isopropylidene-aldehydo-$\beta$-D-arabino-hexos-2-ulo-2,6-pyranose (2.45 g, 9.5 mmol) in 15 mL $H_2O$/THF (1:1, v/v) under $N_2$ at 50° C. After 4 h the solvent was removed under reduced pressure and the crude product ($Rf_A$ for the product=0.8, $Rf_A$ for the starting material=0.45; UV & ninhydrin positive) was purified (RP-FC) using a linear gradient 30-50% B in A over 20 minutes. The intended product eluted at 37% B in A. The pooled fractions were lyophilized. Pure (2) was obtained as a white solid (500 mg, 22%). LC-ESI-MS m/z=611 ($[M+H]^+$), calcd MW=610 at $R_t$=3.06 minutes using a linear gradient of 30-80% B in A over 5 min; at $R_t$=3 min in an analytical RP-HPLC employing a linear gradient 40-80% B in A over 3 min. $^1$H NMR ($CDCl_3$, 400 MHz): δ 7.74 (d, 2H, $J_{3,4}$=$J_{5,6}$=7.4 Hz, fluorenyl 4-H and 5-H), 7.54 (d, 2H, $J_{1,2}$=$J_{7,8}$=7.4 Hz, fluorenyl 1-H and 8-H), 7.37 (pseudo t, 2H, fluorenyl 3-H and 6-H), 7.28 (pseudo t, 2H, fluorenyl 2-H and 7-H), 6.19 (broad s, COOH), 5.46 (m, 1H, NH), 4.49-4.33 (m, 3H, $CH_2$—O and α-H), 4.18 (t, 1H, J=6.4 Hz, fluorenyl 9-H), 3.24-3.21 (m, 2H, $\varepsilon$-$H_2$), 1.70-1.42 (m, 6H, 3×$CH_2$).

Step 2: Synthesis of $N^\alpha$-Fmoc-Lys[Nε-(2,3:4,5-di-O-isopropylidene-1-deoxyfructosyl, $N^\varepsilon$-Boc)]-OH (1)

A stirred solution of (2, 500 mg, 0.81 mmol) in methanol (5 mL) at 0° C. was treated with $Boc_2O$ (445 mg, 2.07 mmol, 2.5 eq). The reaction was stirred at ambient temperature for 1.5 h before the solvent was evaporated and the residue purified by RP-FC employing a linear gradient of 30-50% B in A over 20 min. The product (1) eluted at ~40% B in A. TLC analysis with DCM/MeOH (1:4) eluant was visualized with ninhydrin. Acidification to pH 3 with acetic acid of the concentrate, obtained after evaporation of the acetonitrile from the pooled fractions, resulted in a white precipitate that was filtered off, washed with water, and dried under vacuum.

The pure product (1) was obtained as a white solid (390 mg, 67%). M.p.=97-100° C. LC-ESI-MS calcd: MW=710, found m/z=711 ([M+H]$^+$), m/z=611 ([M+H-Boc]$^+$) at $R_t$=5.24 min using a linear gradient of 30-80% B in A over 5 min; analytical RP-HPLC employing a linear gradient of 70-100% B in A over 3 min, $R_t$=3.42 min. $^1$H NMR (CDCl$_3$, 400 MHz,): δ 7.74 (d, 2H, $J_{3,4}$=$J_{5,6}$=7.4 Hz, fluorenyl 4-H and 5-H), 7.54 (d, 2H, $J_{1,2}$=$J_{7,8}$=7.4 Hz, fluorenyl 1-H and 8-H), 7.37 (pseudo t, 2H, fluorenyl 3-H and 6-H), 7.28 (pseudo t, 2H, fluorenyl 2-H and 7-H), 6.19 (broad s, COOH), 5.46 (m, 1H, NH), 4.49-4.33 (m, 3H, CH$_2$—O and α-H), 4.18 (t, 1H, J=6.4 Hz, fluorenyl 9-H), 3.24-3.21 (m, 2H, ε-H$_2$), 1.70-1.42 (m, 6H, 3×CH$_2$).

Example 3

Synthesis of N$^α$-Fmoc-Lys[N$^ε$-(1-deoxyfructosyl)]-OH (3)

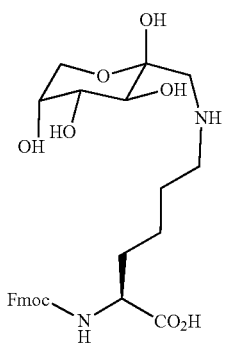

FmocLys-OH (1 g, 2.71 mmol) and D-glucose (1.22 g, 6.77 mmol, 2.5 eq) were suspended in 40 mL of dry DMF under an atmosphere of N$_2$. The reaction was heated to 110° C. for 10 minutes then poured into an ice bath. After a few minutes the Fmoc-Lys-OH dissolved in DMF as a yellow solution. The reaction had to be stopped before the solution was allowed to rapidly turn brown, which indicates the occurrence of diglycated product. The DMF was evaporated under vacuum and the crude residue was purified by RP-FC. TLC analysis with DCM/MeOH (1:4) eluant was visualized with ninhydrin. Pure (3) was obtained as a white solid (390 mg, 67%). LC-ESI-MS calcd: MW=530, found m/z=531 ([M+H]$^+$), $R_t$=2.13 min using a linear gradient of 30-50% B in A over min 5 min; analytical RP-HPLC was employed using a linear gradient of 40-80% B in A over 3 min; $R_t$=1.45 min. $^1$H NMR (CDCl$_3$, 400 MHz,): δ 7.74 (d, 2H, $J_{3,4}$=$J_{5,6}$=7.4 Hz, fluorenyl 4-H and 5-H), 7.54 (d, 2H, $J_{1,2}$=$J_{7,8}$=7.4 Hz, fluorenyl 1-H and 8-H), 7.37 (pseudo t, 2H, fluorenyl 3-H and 6-H), 7.28 (pseudo t, 2H, fluorenyl 2-H and 7-H), 6.19 (broad s, COOH), 5.46 (m, 1H, NH), 4.49-4.33 (m, 3H, CH$_2$—O and α-H), 4.18 (t, 1H, J=6.4 Hz, fluorenyl 9-H), 3.24-3.21 (m, 2H, ε-H$_2$), 1.70-1.42 (m, 6H, 3×CH$_2$).

Example 4

Synthesis of N$^α$-Fmoc-Lys[N$^ε$-(1-deoxyfructosyl, N$^ε$-Boc)]-OH (4)

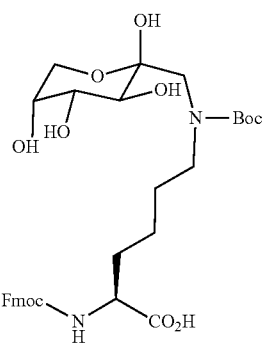

Boc$_2$O (514 mg, 2.35 mmol, 2.5 eq) in 5 mL of MeOH was added under an atmosphere of N$_2$, with stirring at 0° C., to a solution of (3, 500 mg, 0.94 mmol). The reaction warmed to ambient temperature over 1.5 hours, the solvent was evaporated, and the residue was purified by RP-FC with a linear gradient of 30-55% B in A over 20 minutes. In this instance, 0.05% TFA was used in solvents A and B. Intended product eluted at 50% B in A. TLC analysis with DCM/MeOH (1:4) eluant was visualized with ninhydrin. Solvent was removed from the combined fractions and the aqueous solution was lyophilized. Intended product was obtained (270 mg, 100% pure, 45% yield). LC-ESI-MS calcd: MW=630, found m/z=653 ([M+Na]$^+$), gradient of 30-50% B in A over 5 min, $R_t$=5.72 min; analytical RP-HPLC gradient of 40-80% B in A over 3 min, $R_t$=3.1 min. $^1$H NMR (CDCl$_3$, 400 MHz,): δ 7.74 (d, 2H, $J_{3,4}$=$J_{5,6}$=7.4 Hz, fluorenyl 4-H and 5-H), 7.54 (d, 2H, $J_{1,2}$=$J_{7,8}$=7.4 Hz, fluorenyl 1-H and 8-H), 7.37 (pseudo t, 2H, fluorenyl 3-H and 6-H), 7.28 (pseudo t, 2H, fluorenyl 2-H and 7-H), 6.19 (broad s, COOH), 5.46 (m, 1H, NH), 4.49-4.33 (m, 3H, CH$_2$—O and α-H), 4.18 (t, 1H, J=6.4 Hz, fluorenyl 9-H), 3.24-3.21 (m, 2H, ε-H$_2$), 1.70-1.42 (m, 6H, 3×CH$_2$).

Example 5

Resin-Based Reductive Amination to Yield the N$^α$—Ac Lys$^{41}$ Amadori Adduct of Residues 37-50 of CD59

"Residues 37-50 of CD59" are set forth as SEQ ID NO:3. The Lys$^{41}$ Amadori adduct of SEQ ID NO:3 was synthetized from Cys(Trt)-Rink resin starting material according to the polypeptide coupling procedures described above. Fmoc deprotection was accomplished by exposure to 20% piperidine in DMF (v/v), three times, each time for 5 min, followed by washing with DMF. The N-terminal amino group was acetylated by treating the Na-deprotected peptidyl-resin with a 12-fold molar excess of Ac$_2$O and DIEA in DMF for 1.5 h. Deprotection of the Lys$^{41}$(N$^ε$-ivDde) residue was carried out by treatment with 2% hydrazine in DMF for 15 minutes. This deprotection sequence was repeated 7-8 times and monitored by LCMS analysis. The mass of the ivDde deprotection product=221. The Amadori modification was introduced on Lys 41 by reductive amination as follows. The peptidyl-resin was treated with a 25-fold molar excess of 2,3:4,5-di-O-isopropylidene-β-D-arabinose-hexose-2- ulo-2,6-pyranose and 2.5 eq of $NaCNBH_3$ in DMF (1 mL/g of peptidyl-resin) with agitation at 70° C. under an atmosphere of $N_2$ for 4 hours. LCMS analysis was conducted on aliquots of the resin, upon exposure to TFA:anisole:thioanisole:ethanedithiol in a ration of 90:5:3:2 v/v, precipitation cold ether, and lyophilization. Because LCMS analysis indicated the presence of isopropylidene groups, the crude polypeptide was treated with TFA/TIS (95:5), precipitated in cold ether over 2 hours, and lyophilized. The resulting polypeptide was purified by RP-FC using a Waters delta prep3000 with a delta-pak cartridge (C18 15 microm 300 Angstrom), a flow rate of 50 mL/min, and a linear gradient of 10-60% B in A over 20 min. Purified $Lys^{41}(N^\epsilon$-ivDde) protected polypeptide was characterized using a LCMS linear gradient of 10-60% B in A over 20 min, $R_t$=8.38. The crude form of the intended $Lys^{41}$ Amadori adduct of SEQ ID NO:3, after reductive amination, was characterized using an analytical HPLC linear gradient of 5-45% B in A over 60 min, $R_t$=19.28 min. Purified polypeptide, LCMS linear gradient of 10-60% B in A over 20 min, $R_t$=4.58 min. The peak appeared in the first place to correspond to a pure product by LCMS analysis show it was a mixture of glycated ($[M+H]^{2+}$=963.9) and non-glycated polypeptide ($[M+H]^{2+}$=883.1). HPLC analysis using a very shallow gradient shown indeed two peaks. Polypeptide (6+6 unglycated), LCMS linear gradient of 15-17% B in A over 15 min, $R_t$=11.31 min glycated, $R_t$=12.05 unglycated. Further studies shown that C18 (and C4 as well) are not able to separate successfully the glycated and unglycated form of a polypeptide 15-20 or more amino acid residue polypeptide.

Under the described conditions we were unable to glycate all the free epsilon-amino groups at lysine 41. At least 40% of them remained unglycated. Complete glycation was not achieved under more vigorous reaction conditions, such as higher temperatures, longer reaction times, and greater molar excesses of reactants. Under such conditions, diglycation could not be eliminated. Separation of the glycated and di-glycated products was difficult and low yielding. Purification by semipreparative reverse phase HPLC using very shallow and isocratic gradients yielded some pure fractions of glycated product. During LCMS analysis of the glycated product, a linear gradient of 10-20% B in A over 10 minutes was used, $R_t$=5.58 minutes.

Example 6

Resin-Based Direct Glycation of Lysine 41 to Yield the $N^\alpha$—Ac $Lys^{41}$ Amadori Adduct of Residues 37-50 of CD59

The unglycated polypeptide precursor corresponding to the $N^\alpha$—Ac derivative of SEQ ID NO:3 was synthetized and purified according to the methods described above. Direct glycation of lysine 41 of the $N^\alpha$—Ac derivative of SEQ ID NO:3 was performed on the resin-bound polypeptide with a 40-fold molar excess of glucose at 100° C. in DMF, under an atmosphere of $N_2$. The reaction was monitored continuously and stopped after 45 minutes. LCMS analysis revealed the presence of glycated product in the crude product. LCMS analysis employed a linear gradient of 10-20% B in A over 15 min, with a $R_t$=4.66 minutes. The masses of intended and non-intended products are as follows: glycated product $[M+H]^+$=1927.2 $[M+H]^{2+}$=963.96; un-glycated product $[M+H]^+$=1765 $[M+H]^{2+}$=883; oxidation product $[M+H]^+$=1969.5 $[M+H]^{2+}$=985; di-glycated product $[M+H]^+$=2089 $[M+H]^{2+}$=1045.

LCMS analysis indicated the presence of unglycated polypeptide and poor yields of the glycated product due to the presence of undesired oxidation reactions and diglycation. The HPLC trace further indicated that the glycated product and above-indicated side products have surprisingly similar retention times. Crude polypeptide was subjected to an analytical HPLC linear gradient of 5 to 45% B in A over 60 minutes and yielded a polypeptide mixture at $R_t$=18.92 minutes. Subsequent attempts were made to separate the polypeptide mixture by flash chromatography using Waters delta prep3000, a delta-pak cartridge (C18 15 micron, 300 Angstrom 2 inc (diam)×12 inc), at a 50 mL/min linear gradient with 10-60% B in A. HPLC analysis of the resulting polypeptides, using a very shallow gradient, indicated the presence of two peaks corresponding to glycated and un-glycated with the oxidation product. An alternative gradient of 15-17% B in A over 15 minutes yielded better separation with a $R_t$=13.08 min for the glycated polypeptide, and a $R_t$=13.85 min for the unglycated polypeptide. Further purification by semipreparative reverse phase HPLC using very shallow and isocratic gradients was low yielding due to the poor separation. However it was possible to isolate same pure fractions in the first half of the glycated peak LCMS analysis of pure fractions of the $N^\alpha$—Ac $Lys^{41}$ Amadori adduct of SEQ ID NO:3 were conducted with a linear gradient of 10-20% B in A over 10 min. This polypeptide exhibited a $R_t$=4.65 min.

Example 7

Reductive Amination in Solution of Lysine 41 to Yield the $N^\alpha$—Ac $Lys^{41}$ Amadori Adduct of Residues 37-50 of CD59

The $N^\alpha$—Ac $Lys^{41}$ Amadori adduct of SEQ ID NO:3 was obtained by adding 2,3:4,5-di-O-isopropylidene-β-D-arabino-hexos-2-ulo-2,6-pyranose (160 mg, 0.62 mmol) and $NaCNBH_3$ (70 mg 1.1 mmol) to an aqueous solution (2 mL) of the N-terminal acetylated polypeptide (25 mg, 0.012 mmol), unprotected but for the ivDde-protected amino side-chain of Lys38. The reaction was monitored by LCMS and stopped after 20 minutes. Dithiothreitol (DTT) was added and the solution was stirred for 1 hour. The product was purified on a semiprep HPLC, using a reverse phase linear gradient of 10-60% B in A over 45 minutes, followed by lyophilization. The lyophylized polypeptide was dissolved in 500 μL of MeOH and 2% hydrazine (10 μL was added with a small amount of DTT). Deprotection of the ivDde group was monitored by LCMS and the reaction was quenched after 2 hours with 500 μL of a 50% aqueous acetic acid solution. The resulting product was purified with semiprep HPLC, using a reverse phase linear gradient of 10-60% B in A over 45 minutes, followed by lyophilization. The lyophylized polypeptide was dissolved in 2 mL TFA/$H_2O$/TIS (95:2.5:2.5) and deprotection of the isopropylidene groups was monitored with LCMS. After complete deprotection, the TFA was evaporated with $N_2$ and the product residue was dissolved in a 50% aqueous acetic acid solution and lyophilized.

LC-MS analysis of product mixture was conducted with a linear gradient of 10-60% B in A over 10 minutes. The glycated polypeptide eluted at 4 minutes; $[M+H]^+$=2007.8; $[M+2H]^{2+}$=1004.4; $[M+3H]^{3+}$=670. Starting material eluted at 5.5 minutes: $[M+H]^+$=1970; $[M+2H]^{2+}$=986.4; $[M+3H]^{3+}$=658. Reaction mixture+DTT was detected; $[M+H]^+$=2214; $[M+2H]^{2+}$=1107.5 $[M+3H]^{3+}$=738.8. The ivDde-protected polypeptide eluted at 6.3 minutes; $[M+H]^+$ =2214; [M+2H]$^{2+}$=1107.5; [M+3H]$^{3+}$=738.8. The isopropylidene-protected glycated polypeptide eluted at 4 minutes; [M+H]$^{+}$=2007.8 [M+2H]$^{2+}$=1004.4 [M+3H]$^{3+}$=670. Treatment of the isopropylidene-protected glycated polypeptide with 2% hydrazine yielded further quantities of the intended glycated polypeptide.

Example 8

Synthesis of the N$^{\alpha}$—Ac Lys$^{41}$ Amadori Adduct of Residues 37-50 of CD59

A 40-fold excess of glucose (86.4 mg, 0.48 mmol), the N-terminal acetylated polypeptide unprotected but for the ivDde-protected Lys38 residue (25 mg, 0.012 mmol), and DMF (2 mL) were stirred at 100° C. under an atmosphere of N$_2$. The polypeptide was found to be unstable in solution at temperatures of 100-110° C. At lower temperatures the stability of the polypeptide increased but glycation was incomplete. The Amadori modification was also unstable in the presence of hydrazine.

Example 9

Generation of Anti-Amadori gCD59 Mouse mAb

Step 1. Conjugation of Amadori-gCD59 Derived Peptide to MI-KLH 2 mg of Amadori peptide was dissolved in 200 µl of H$_2$O. Also, 200 µl of H$_2$O was added to inject maleimide-activated KLH (MI-KLH) (2 mg vial). These two were then quickly mixed and allowed to react for 4 hours. The reaction mixture was then dialyzed overnight against water. After dialysis the conjugated peptide was removed from the dialysis cassette and buffered with PBS. The volume was finally made up to 1 ml.

Step 2. Immunization of Mice to Obtain Hyperimmunized Animals

Six BALB/c mice from Charles River Laboratories were used. 50 µl of blood was drawn from the tail vein of each animal (pre-immune sera). 200 µl of 2 mg/ml of Amadori-gCD59 derived peptide-KLH conjugate were mixed with 200 µl of Freund's complete adjuvant. 25-50 µl of this mixture was injected intraperitoneally (IP) into all six mice. Seven days later, 200 µl of Amadori-gCD59 derived peptide-KLH conjugate was mixed with 200 µl of Freund's incomplete adjuvant. 25-50 µl of this conjugate mixture was injected IP into each of the six mice. Nine days later, 250 µl of 2 mg/ml of Amadori-gCD59 derived peptide-KLH conjugate was mixed with 250 µl of Freund's incomplete adjuvant and 25-50 µl of this preparation was injected IP into each of the six mice. Seven, fourteen, and twenty-one days later, 2 mg/ml of Amadori-gCD59 derived peptide-KLH conjugate in PBS was prepared, and 50 µl of this preparation were injected via the tail vein into each of the six mice. Four days later, 50 µl of blood was drawn from the tail vein of each animal. Two days later, fusion was carried out.

Step 3. Selection of Responding Animals Based on Polyclonal Ab in Serum

Figure 12:
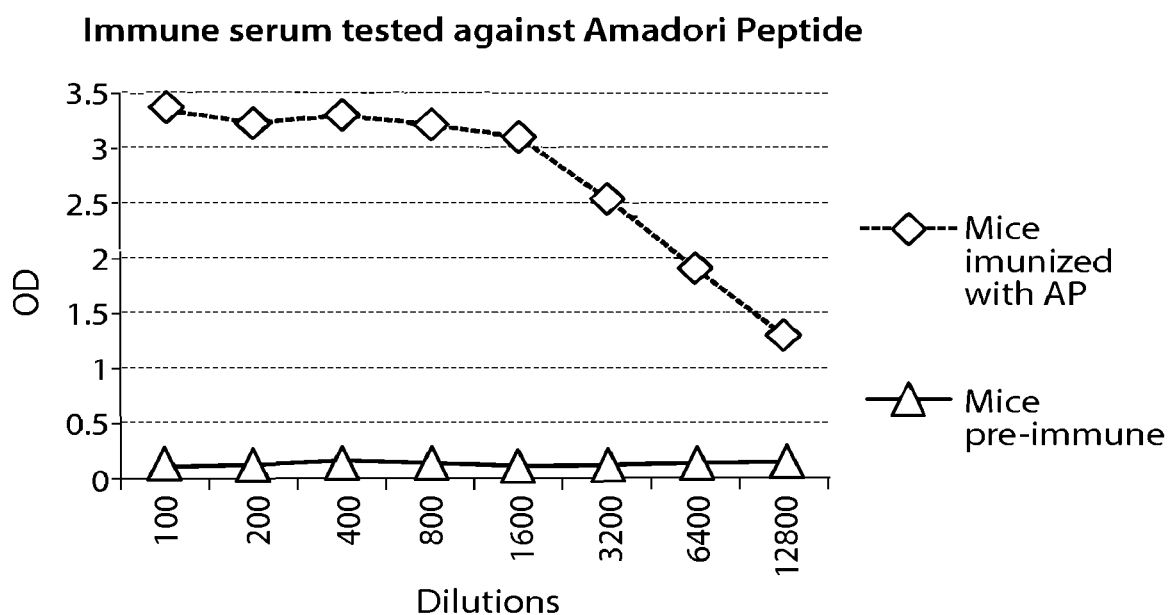
FIG. 12 depicts the immune serum tested against Amadori-gCD59 derived peptide (AP).
Figure 13A:
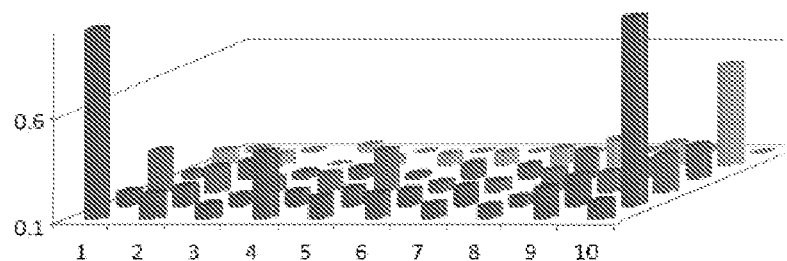
FIGS. 13A-13D depict the results of the monoclonal supernatant tested against Amadori-gCD59 derived peptide (AP); Plate 1 (FIG. 13A), Plate 2 (FIG. 13B), Plate 3 (FIG. 13C), and Plate 4 (FIG. 13D).
Figure 13B:
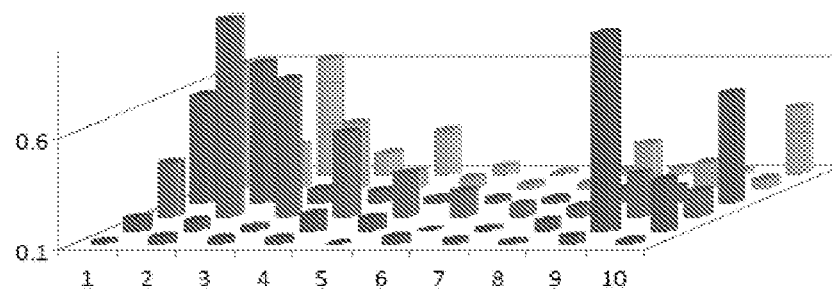
Figure 13C:
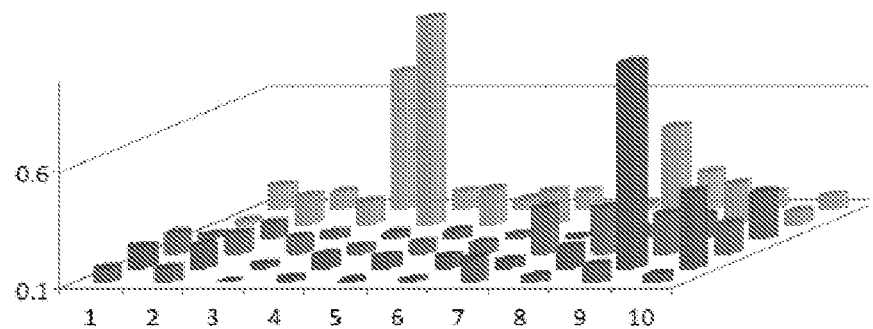
Figure 13D:
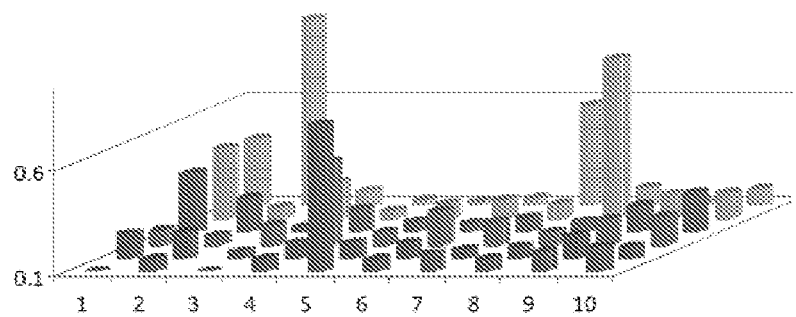

FIG. 12 depicts the immune serum tested against Amadori-gCD59 derived peptide (AP).

Step 4. Fusion of Lymphocytes and Spleenocytes from Hyperimmunized Animals with sp2/O Myeloma Cells to Generate Hybridoma Cell Lines A. Preparation of Feeder Layer. Two mice (not immunized) were sacrificed, and peritoneal macrophage were isolated. The spleen of one of the mice was also isolated, and its cells were isolated and pooled with the macrophage above. The pool was centrifuged at 400 rcf for 10 mins and resuspended in 50 ml of medium containing 5% FBS/1× optimab/1× penicillin-streptomycin. With 50 µl/well, it was distributed in ten plates.

B. Fusion of spleenocytes with sp2/O cells. 4×75 cm$^2$ flasks containing confluent myeloma cells were harvested, and the cells were resuspended in fresh media. Hyperimmunized mice were sacrificed by CO$_2$ asphyxiation, and the lymphnodes and spleens were removed aseptically and kept in media with FBS (fetal bovine serum). Cells from lymph nodes were isolated by holding the node with pointed forceps and dissecting it with a 20 gauge needle. Lymphnode cells were pooled with myeloma cells and were centrifuged at 200 rcf for 10 mins, and the supernatant was removed. The cells were then resuspended in 10 ml serum free media and then centrifuged again at 200 rcf for 10 mins. After centrifugation, supernatant was removed, and cells were fused by the addition of 800 µl of PEG in 1 min and then 1 ml of serum free media. In the next 2-3 mins, another 10 ml of media were added. This was allowed to stand for 5-7 mins and then centrifuged at 200 rcf for 10 mins. Supernatant was removed, and the cells were resuspended in 50 ml media with all supplements but antibiotics. Part of the cell were plated (200 µl/well) with feeder layer and remaining without feeder. The same protocol was repeated for the cells isolated from spleens.

Step 5. Selection and Cloning of Hybridoma Cell Lines that Stably Secret Anti-Amadori gCD59 Mouse mAb Within 5-7 days of fusion, many wells showed cells with dividing colonies. At this stage the supernatant was removed from the wells and was ready to be used for screening assay. FIGS. 13A-13D depict the results of the monoclonal supernatant tested against Amadori-gCD59 derived peptide (AP). See corresponding tabulated data below for Plate 1 (FIG. 13A), Plate 2 (FIG. 13B), Plate 3 (FIG. 13C), and Plate 4 (FIG. 13D); greater than 0.5 are highlighted.

| Plate 1 | | | | | | |
|---|---|---|---|---|---|---|
| 1 | 2 | 3 | 4 | 5 | 6 | 7 |
| 1.66304 | 0.219489 | 0.168171 | 0.418855 | 0.205322 | 0.221484 | 0.171581 |
| 0.163891 | 0.191528 | 0.152011 | 0.167795 | 0.186054 | 0.170731 | 0.190663 |
| 0.294381 | 0.220751 | 0.162161 | 0.188602 | 0.298145 | 0.148735 | 0.155349 |

-continued

| Plate 1 | | | | | | |
|---|---|---|---|---|---|---|
| 0.130915 | 0.182613 | 0.129273 | 0.151201 | 0.121688 | 0.17157 | 0.166405 |
| 0.173461 | 0.155366 | 0.0945865 | 0.135715 | 0.152426 | 0.166671 | 0.183645 |
| 0.116723 | 0.109749 | 0.134799 | 0.102488 | 0.0930044 | 0.0938009 | 0.0940673 |
| 3.2227 | 3.1808 | 3.27212 | 3.14745 | 2.70543 | 2.03846 | 1.35311 |
| 0.133617 | 0.105051 | 0.152069 | 0.138488 | 0.101639 | 0.0998094 | 0.130311 |

| | 8 | 9 | 10 | 11 | 12 |
|---|---|---|---|---|---|
| | 0.164181 | 0.246777 | 0.183367 | 3.30716 | 0.446175 |
| | 0.143117 | 0.240353 | 2.15216 | 3.20488 | 0.151515 |
| | 0.206467 | 0.1933353 | 0.28031 | 3.28135 | 0.193608 |
| | 0.232632 | 0.187231 | 0.263108 | 3.19398 | 0.121128 |
| | 0.224013 | 0.201183 | 0.582219 | 3.09226 | 0.148264 |
| | 0.111074 | 0.115636 | 0.102621 | 2.5234 | 0.0744555 |
| | 0.838257 | 0.658791 | 0.112466 | 1.90835 | 0.101223 |
| | 0.138562 | 0.134916 | 0.169995 | 1.28471 | 0.120381 |

| Plate 2 | | | | | | |
|---|---|---|---|---|---|---|
| 1 | 2 | 3 | 4 | 5 | 6 | 7 |
| 0.115742 | 0.137688 | 0.126883 | 0.128428 | 0.0904577 | 0.135033 | 0.124529 |
| 0.159506 | 0.145218 | 0.120136 | 0.176855 | 0.161251 | 0.103244 | 0.112129 |
| 0.349759 | 2.97164 | 0.724123 | 0.485089 | 0.295443 | 0.218856 | 0.153462 |
| 0.589784 | 0.735836 | 0.160089 | 0.155365 | 0.124008 | 0.122718 | 0.115588 |
| 0.66406 | 0.299968 | 0.400464 | 0.177105 | 0.148992 | 0.123734 | 0.122509 |
| 0.2188112 | 0.629229 | 0.196075 | 0.304097 | 0.142408 | 0.112724 | 0.118517 |
| 1.69955 | 0.172472 | 0.156867 | 0.207797 | 0.215293 | 0.122176 | 0.107636 |
| 0.166682 | 0.083001 | 0.155365 | 0.105361 | 0.138518 | 0.140324 | 0.145701 |

| | 8 | 9 | 10 | 11 | 12 |
|---|---|---|---|---|---|
| | 0.116574 | 0.414 | 0.120381 | 0.0961056 | 0.102268 |
| | 0.146322 | 2.82511 | 0.329773 | 0.089411 | 0.121589 |
| | 0.145597 | 0.298593 | 0.214558 | 0.127546 | 0.107156 |
| | 0.160032 | 0.175067 | 0.602616 | 0.0904697 | 0.104478 |
| | 0.305598 | 0.216911 | 0.139436 | 0.101694 | 0.131291 |
| | 0.131153 | 0.125306 | 0.407592 | 0.134621 | 0.108745 |
| | 0.152956 | 0.246087 | 0.153433 | 0.0746201 | 0.0936972 |
| | 0.120011 | 0.168808 | 2.1732 | 0.12433 | 0.0982472 |

| Plate 3 | | | | | | |
|---|---|---|---|---|---|---|
| 1 | 2 | 3 | 4 | 5 | 6 | 7 |
| 0.166756 | 0.164242 | 0.0798592 | 0.123268 | 0.11021 | 0.113607 | 0.207151 |
| 0.198636 | 0.201786 | 0.11871 | 0.157893 | 0.155942 | 0.154899 | 0.137789 |
| 0.190241 | 0.193083 | 0.1711963 | 0.1332245 | 0.149854 | 0.146137 | 0.303988 |
| 0.120255 | 0.174441 | 0.132338 | 0.127797 | 0.133075 | 0.1217 | 0.113077 |
| 0.1144 | 0.22645 | 0.202677 | 2.46627 | 0.252365 | 0.248074 | 0.173642 |
| 0.209719 | 0.180352 | 0.708621 | 0.185216 | 0.145175 | 0.185471 | 0.133446 |
| 0.287589 | 0.207422 | 0.110805 | 0.122059 | 0.273477 | 0.0813794 | 0.122006 |
| 0.227953 | 0.1348817 | 0.151313 | 0.133589 | 0.138667 | 0.136704 | 0.132521 |

| | 8 | 9 | 10 | 11 | 12 |
|---|---|---|---|---|---|
| | 0.128031 | 0.179228 | 0.134036 | 0.114472 | 0.103047 |
| | 0.194347 | 2.65462 | 0.438742 | 0.125467 | 0.178624 |
| | 0.304133 | 0.2733784 | 0.232823 | 0.145843 | 0.143027 |
| | 0.148211 | 0.201442 | 0.304115 | 0.113797 | 0.119802 |
| | 0.524769 | 0.279503 | 0.15736 | 0.130531 | 0.162399 |

-continued

Plate 3

| | | | | |
|---|---|---|---|---|
| 0.268408 | 0.176962 | 0.168584 | 0.164292 | 0.0847645 |
| 0.2049 | 0.146418 | 0.2278 | 0.104367 | 0.146153 |
| 0.22943 | 0.120446 | 0.260173 | 0.181061 | 0.155361 |

Plate 4

| 1 | 2 | 3 | 4 | 5 | 6 | 7 |
|---|---|---|---|---|---|---|
| 0.087772 | 0.162759 | 0.0951647 | 0.166501 | 0.811014 | 0.160934 | 0.189793 |
| 0.223293 | 0.232656 | 0.136798 | 0.179643 | 0.180978 | 0.179513 | 0.145017 |
| 0.170919 | 0.148302 | 0.201295 | 0.498967 | 0.165086 | 0.267497 | 0.219492 |
| 0.385288 | 0.261795 | 0.124713 | 0.214673 | 0.155176 | 0.149127 | 0.174366 |
| 0.441149 | 0.157641 | 0.281647 | 0.138921 | 0.176615 | 0.195981 | 0.172368 |
| 0.41802 | 1.19892 | 0.170749 | 0.13013 | 0.124882 | 0.137787 | 0.588059 |
| 0.145211 | 0.101972 | 0.0849166 | 0.0972721 | 0.144463 | 0.111274 | 0.114306 |
| 0.19042 | 0.0908658 | 0.148257 | 0.0896348 | 0.115101 | 0.0871228 | 0.130945 |

| 8 | 9 | 10 | 11 | 12 |
|---|---|---|---|---|
| 0.163971 | 0.20028 | 0.221277 | 0.103596 | 0.205232 |
| 0.161702 | 0.212981 | 0.159029 | 0.158529 | 0.20302 |
| 0.1677 | 0.226473 | 0.239645 | 0.17568 | 0.153866 |
| 0.158145 | 0.227758 | 0.289835 | 0.134949 | 0.164334 |
| 0.867488 | 0.223421 | 0.227715 | 0.153104 | 0.155621 |
| 0.187323 | 0.11726 | 0.178806 | 0.144948 | 0.076548 |
| 0.174295 | 0.176429 | 0.494668 | 0.126175 | 0.11543 |
| 0.0907672 | 0.145234 | 0.219401 | 0.15761 | 0.183025 |

Other Embodiments

This application refers to various issued patents, published patent applications, journal articles, books, manuals, and other publications, all of which are incorporated herein by reference.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

APPENDIX

Sequence Listing

The K-glycated Amadori pentapeptide fragment of CD59.
(SEQ ID NO: 1)
WKFEH

A non-glycated pentapeptide fragment of CD59.
(SEQ ID NO: 2)
WKFEH

The K-glycated Amadori product of the CD59 modified polypeptide fragment set forth as SEQ ID NO: 4 to which a cysteine residue has been added to the C-terminus to create a "handle" for conjugation of the resulting peptide to an affinity column or a carrier protein.
(SEQ ID NO: 3)
NKAWKFEHANFNDC A non-glycated polypeptide fragment of CD59.
(SEQ ID NO: 4)
NKCWKFEHCNFND The full-length non-glycated CD59 polypeptide of 128 amino acid residues.
(SEQ ID NO: 5)
Met Gly Ile Gln Gly Gly Ser Val Leu Phe Gly Leu Leu Leu Val Leu
1               5                   10                  15

APPENDIX-continued

Sequence Listing

```
Ala Val Phe Cys His Ser Gly His Ser Leu Gln Cys Tyr Asn Cys Pro
            20                  25                  30

Asn Pro Thr Ala Asp Cys Lys Thr Ala Val Asn Cys Ser Ser Asp Phe
            35                  40                  45

Asp Ala Cys Leu Ile Thr Lys Ala Gly Leu Gln Val Tyr Asn Lys Cys
            50                  55                  60

Trp Lys Phe Glu His Cys Asn Phe Asn Asp Val Thr Thr Arg Leu Arg
65                  70                  75                  80

Glu Asn Glu Leu Thr Tyr Tyr Cys Cys Lys Lys Asp Leu Cys Asn Phe
                    85                  90                  95

Asn Glu Gln Leu Glu Asn Gly Gly Thr Ser Leu Ser Glu Lys Thr Val
                   100                 105                 110

Leu Leu Leu Val Thr Pro Phe Leu Ala Ala Ala Trp Ser Leu His Pro
                115                 120                 125
```

The non-glycated mature form of the CD59 polypeptide of 103 amino acid residues that is present in cells and tissues.

(SEQ ID NO: 6)
```
Leu Gln Cys Tyr Asn Cys Pro Asn Pro Thr Ala Asp Cys Lys Thr Ala
1               5                   10                  15

Val Asn Cys Ser Ser Asp Phe Asp Ala Cys Leu Ile Thr Lys Ala Gly
            20                  25                  30

Leu Gln Val Tyr Asn Lys Cys Trp Lys Phe Glu His Cys Asn Phe Asn
            35                  40                  45

Asp Val Thr Thr Arg Leu Arg Glu Asn Glu Leu Thr Tyr Tyr Cys Cys
            50                  55                  60

Lys Lys Asp Leu Cys Asn Phe Asn Glu Gln Leu Glu Asn Gly Gly Thr
65                  70                  75                  80

Ser Leu Ser Glu Lys Thr Val Leu Leu Leu Val Thr Pro Phe Leu Ala
                    85                  90                  95

Ala Ala Trp Ser Leu His Pro
                   100
```

The K41-glycated (X) form of the CD59 polypeptide of 103 amino acid residues.

(SEQ ID NO: 7)
```
Leu Gln Cys Tyr Asn Cys Pro Asn Pro Thr Ala Asp Cys Lys Thr Ala
1               5                   10                  15

Val Asn Cys Ser Ser Asp Phe Asp Ala Cys Leu Ile Thr Lys Ala Gly
            20                  25                  30

Leu Gln Val Tyr Asn Lys Cys Trp (X) Phe Glu His Cys Asn Phe Asn
            35                  40                  45

Asp Val Thr Thr Arg Leu Arg Glu Asn Glu Leu Thr Tyr Tyr Cys Cys
            50                  55                  60

Lys Lys Asp Leu Cys Asn Phe Asn Glu Gln Leu Glu Asn Gly Gly Thr
65                  70                  75                  80

Ser Leu Ser Glu Lys Thr Val Leu Leu Leu Val Thr Pro Phe Leu Ala
                    85                  90                  95

Ala Ala Trp Ser Leu His Pro
                   100
```

The mature form of the CD59 polypeptide of 103 amino acid residues that includes the glycated Amadori modification (X) at lysines K14, K30, K38, K41, K65, K66, and K85.

(SEQ ID NO: 8)
```
Leu Gln Cys Tyr Asn Cys Pro Asn Pro Thr Ala Asp Cys (X) Thr Ala
1               5                   10                  15

Val Asn Cys Ser Ser Asp Phe Asp Ala Cys Leu Ile Thr (X) Ala Gly
            20                  25                  30
```

APPENDIX-continued

Sequence Listing

Leu Gln Val Tyr Asn (X) Cys Trp (X) Phe Glu His Cys Asn Phe Asn
         35              40                  45

Asp Val Thr Thr Arg Leu Arg Glu Asn Glu Leu Thr Tyr Tyr Cys Cys
 50              55                  60

(X) (X) Asp Leu Cys Asn Phe Asn Glu Gln Leu Glu Asn Gly Gly Thr
 65              70                  75                  80

Ser Leu Ser Glu (X) Thr Val Leu Leu Leu Val Thr Pro Phe Leu Ala
             85              90                  95

Ala Ala Trp Ser Leu His Pro
            100

The full-length nucleic acid sequence of CD59.
                                                        (SEQ ID NO: 9)
ctttagcacc agttggtgta ggagttgaga cctacttcac agtagttctg tggacaatca    60
caatgggaat ccaaggaggg tctgtcctgt tcgggctgct gctcgtcctg gctgtcttct   120
gccattcagg tcatagcctg cagtgctaca actgtcctaa cccaactgct gactgcaaaa   180
cagccgtcaa ttgttcatct gattttgatg cgtgtctcat taccaaagct gggttacaag   240
tgtataacaa gtgttggaag tttgagcatt gcaatttcaa cgacgtcaca acccgcttga   300
gggaaaatga gctaacgtac tactgctgca agaaggacct gtgtaacttt aacgaacagc   360
ttgaaaatgg tgggacatcc ttatcagaga aaacagttct tctgctggtg actccatttc   420
tggcagcagc ctggagcctt catccctaag tcaacaccag gagagcttct cccaaactcc   480
ccgttcctgc gtagtccgct ttctcttgct gccacattct aaaggcttga tattttccaa   540
atggatcctg ttgggaaaga ataaaattag cttgagca                            578

The non-glycated CD59 polypeptide fragment set forth as SEQ ID NO: 4 to
which a cysteine residue has been added to the C-terminus to create a
"handle" for conjugation of the resulting peptide to an affinity column
or a carrier protein.
                                                        (SEQ ID NO: 10)
NKAWKFEHANFNDC The following sequences are CD59 polypeptide fragments which include K41.
                                                        (SEQ ID NO: 11)
WKFEHC;

(SEQ ID NO: 12)
WKFEHCN;

(SEQ ID NO: 13)
WKFEHCNFNDVTTRLREN;

(SEQ ID NO: 14)
CWKFEHCNFNDVTTRLRENELTY;

(SEQ ID NO: 15)
AGLQVYNKCWKFEHCNFNDVTTRLRENELT;

(SEQ ID NO: 16)
QVYNKCWKFEHCNFND;

(SEQ ID NO: 17)
AGLQVYNKCWKFEHCNF;

(SEQ ID NO: 18)
DFDACLITKAGLQVYNKCWKFEHCNFNDVTTRLRENELTYYC;

(SEQ ID NO: 19)
KCWKFEHCNFNDVTTRLR;

(SEQ ID NO: 20)
KCWKFEHCNFNDVTTRLRENELTYYC;

(SEQ ID NO: 21)
VYNKCWKFEHCNF;

APPENDIX-continued

Sequence Listing

```
                                                    (SEQ ID NO: 22)
GLQVYNKCWKFEHCNFND;

(SEQ ID NO: 23)
YNKCWKFEHCNFNE;

(SEQ ID NO: 24)
AGLQVYNKCWKFEHCNFN;
and (SEQ ID NO: 25)
NKCWKFEHC.
```

The following sequences are CD59 polypeptide fragments which include K14.

```
                                                    (SEQ ID NO: 26)
PNPTADCKTAVNC;

(SEQ ID NO: 27)
DCKTAVNC;

(SEQ ID NO: 28)
PNPTADCKTAVNC;
and (SEQ ID NO: 29)
LQCYNCPNPTADCK.
```

The following sequences are CD59 polypeptide fragments which include K30.

```
                                                    (SEQ ID NO: 30)
DFDACLITKAGLQ;

(SEQ ID NO: 31)
FDACLITKAGLQVY;

(SEQ ID NO: 32)
CLITKAGLQVYN;
and (SEQ ID NO: 33)
DFDACLITKAG.
```

What is claimed is:

1. A glycated peptide comprising:

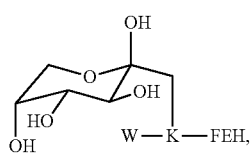

(SEQ ID NO: 1)

or a protected form thereof.

2. A composition comprising:
   (i) the glycated peptide of claim 1 or the protected form thereof; and
   (ii) an adjuvant.

3. The composition of claim 2, wherein the adjuvant is Freund's complete adjuvant or Freund's incomplete adjuvant.

4. A composition comprising:
   (i) the glycated peptide of claim 1 or the protected form thereof; and
   (ii) a pharmaceutically acceptable carrier.

5. A substantially pure glycated peptide comprising:

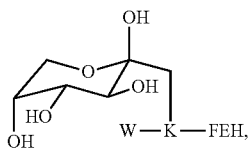

(SEQ ID NO: 1)

or a protected form thereof.

6. A composition comprising:
   (i) the substantially pure glycated peptide of claim 5 or the protected form thereof; and
   (ii) an adjuvant.

7. The composition of claim 6, wherein the adjuvant is Freund's complete adjuvant or Freund's incomplete adjuvant.

8. A composition comprising:
   (i) the substantially pure glycated peptide of claim 5 or the protected form thereof; and
   (ii) a pharmaceutically acceptable carrier.

* * * * *

SEQUENCE LISTING

```
<160> NUMBER OF SEQ ID NOS: 49

<210> SEQ ID NO 1
<211> LENGTH: 5
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Glycated-Lys

<400> SEQUENCE: 1

Trp Lys Phe Glu His
1               5

<210> SEQ ID NO 2
<211> LENGTH: 5
<212> TYPE: PRT
<213> ORGANISM: Homo sapiens

<400> SEQUENCE: 2

Trp Lys Phe Glu His
1               5

<210> SEQ ID NO 3
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Glycated-Lys

<400> SEQUENCE: 3

Asn Lys Ala Trp Lys Phe Glu His Ala Asn Phe Asn Asp Cys
1               5                   10

<210> SEQ ID NO 4
<211> LENGTH: 13
<212> TYPE: PRT
<213> ORGANISM: Homo sapiens

<400> SEQUENCE: 4

Asn Lys Cys Trp Lys Phe Glu His Cys Asn Phe Asn Asp
1               5                   10

<210> SEQ ID NO 5
<211> LENGTH: 128
<212> TYPE: PRT
<213> ORGANISM: Homo sapiens

<400> SEQUENCE: 5

Met Gly Ile Gln Gly Gly Ser Val Leu Phe Gly Leu Leu Leu Val Leu
1               5                   10                  15

Ala Val Phe Cys His Ser Gly His Ser Leu Gln Cys Tyr Asn Cys Pro
            20                  25                  30

Asn Pro Thr Ala Asp Cys Lys Thr Ala Val Asn Cys Ser Ser Asp Phe
        35                  40                  45

Asp Ala Cys Leu Ile Thr Lys Ala Gly Leu Gln Val Tyr Asn Lys Cys
    50                  55                  60

Trp Lys Phe Glu His Cys Asn Phe Asn Asp Val Thr Thr Arg Leu Arg
65                  70                  75                  80

Glu Asn Glu Leu Thr Tyr Tyr Cys Cys Lys Lys Asp Leu Cys Asn Phe
                85                  90                  95

Asn Glu Gln Leu Glu Asn Gly Gly Thr Ser Leu Ser Gly Lys Thr Val
            100                 105                 110

Leu Leu Leu Val Thr Pro Phe Leu Ala Ala Ala Trp Ser Leu His Pro
        115                 120                 125

<210> SEQ ID NO 6
<211> LENGTH: 103
<212> TYPE: PRT
<213> ORGANISM: Homo sapiens

<400> SEQUENCE: 6

Leu Gln Cys Tyr Asn Cys Pro Asn Pro Thr Ala Asp Cys Lys Thr Ala
1               5                   10                  15

Val Asn Cys Ser Ser Asp Phe Asp Ala Cys Leu Ile Thr Lys Ala Gly
            20                  25                  30

Leu Gln Val Tyr Asn Lys Cys Trp Lys Phe Glu His Cys Asn Phe Asn
        35                  40                  45

Asp Val Thr Thr Arg Leu Arg Glu Asn Glu Leu Thr Tyr Tyr Cys Cys
    50                  55                  60
```

-continued

Lys Lys Asp Leu Cys Asn Phe Asn Glu Gln Leu Glu Asn Gly Gly Thr
 65                  70                  75                  80

Ser Leu Ser Glu Lys Thr Val Leu Leu Val Thr Pro Phe Leu Ala
                 85                  90                  95

Ala Ala Trp Ser Leu His Pro
            100

<210> SEQ ID NO 7
<211> LENGTH: 103
<212> TYPE: PRT
<213> ORGANISM: Homo sapiens
<220> FEATURE:
<221> NAME/KEY: MOD_RES
<222> LOCATION: (41)..(41)
<223> OTHER INFORMATION: Glycated-Lys

<400> SEQUENCE: 7

Leu Gln Cys Tyr Asn Cys Pro Asn Pro Thr Ala Asp Cys Lys Thr Ala
 1               5                  10                  15

Val Asn Cys Ser Ser Asp Phe Asp Ala Cys Leu Ile Thr Lys Ala Gly
                 20                  25                  30

Leu Gln Val Tyr Asn Lys Cys Trp Lys Phe Glu His Cys Asn Phe Asn
             35                  40                  45

Asp Val Thr Thr Arg Leu Arg Glu Asn Glu Leu Thr Tyr Tyr Cys Cys
     50                  55                  60

Lys Lys Asp Leu Cys Asn Phe Asn Glu Gln Leu Glu Asn Gly Gly Thr
 65                  70                  75                  80

Ser Leu Ser Glu Lys Thr Val Leu Leu Val Thr Pro Phe Leu Ala
                 85                  90                  95

Ala Ala Trp Ser Leu His Pro
            100

<210> SEQ ID NO 8
<211> LENGTH: 103
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Glycated-Lys
<220> FEATURE:
<221> NAME/KEY: MOD_RES
<222> LOCATION: (30)..(30)
<223> OTHER INFORMATION: Glycated-Lys
<220> FEATURE:
<221> NAME/KEY: MOD_RES
<222> LOCATION: (38)..(38)
<223> OTHER INFORMATION: Glycated-Lys
<220> FEATURE:
<221> NAME/KEY: MOD_RES
<222> LOCATION: (41)..(41)
<223> OTHER INFORMATION: Glycated-Lys
<220> FEATURE:
<221> NAME/KEY: MOD_RES
<222> LOCATION: (65)..(66)
<223> OTHER INFORMATION: Glycated-Lys
<220> FEATURE:
<221> NAME/KEY: MOD_RES
<222> LOCATION: (85)..(85)
<223> OTHER INFORMATION: Glycated-Lys

<400> SEQUENCE: 8

Leu Gln Cys Tyr Asn Cys Pro Asn Pro Thr Ala Asp Cys Lys Thr Ala
 1               5                  10                  15

Val Asn Cys Ser Ser Asp Phe Asp Ala Cys Leu Ile Thr Lys Ala Gly
                 20                  25                  30

```
Leu Gln Val Tyr Asn Lys Cys Trp Lys Phe Glu His Cys Asn Phe Asn
            35                  40                  45
Asp Val Thr Thr Arg Leu Arg Glu Asn Glu Leu Thr Tyr Tyr Cys Cys
     50                  55                  60
Lys Lys Asp Leu Cys Asn Phe Asn Glu Gln Leu Glu Asn Gly Gly Thr
 65                  70                  75                  80
Ser Leu Ser Glu Lys Thr Val Leu Leu Val Thr Pro Phe Leu Ala
                 85                  90                  95
Ala Ala Trp Ser Leu His Pro
            100
```

<210> SEQ ID NO 9
<211> LENGTH: 578
<212> TYPE: DNA
<213> ORGANISM: Homo sapiens

<400> SEQUENCE: 9

```
ctttagcacc agttggtgta ggagttgaga cctacttcac agtagttctg tggacaatca     60
caatgggaat ccaaggaggg tctgtcctgt tcgggctgct gctcgtcctg gctgtcttct    120
gccattcagg tcatagcctg cagtgctaca actgtcctaa cccaactgct gactgcaaaa    180
cagccgtcaa ttgttcatct gattttgatg cgtgtctcat taccaaagct gggttacaag    240
tgtataacaa gtgttggaag tttgagcatt gcaatttcaa cgacgtcaca acccgcttga    300
gggaaaatga gctaacgtac tactgctgca gaaggacctg tgtaactttt aacgaacagc    360
ttgaaaatgg tggacatccc ttatcagaga aaacagttct tctgctggtg actccatttc    420
tggcagcagc ctggagcctt catccctaag tcaacaccag gagagcttct cccaaactcc    480
ccgttcctgc gtagtccgct ttctcttgct gccacattct aaaggcttga tattttccaa    540
atggatcctg ttgggaaaga ataaaattag cttgagca                            578
```

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

```
Asn Lys Ala Trp Lys Phe Glu His Ala Asn Phe Asn Asp Cys
  1               5                  10
```

<210> SEQ ID NO 11
<211> LENGTH: 6
<212> TYPE: PRT
<213> ORGANISM: Homo sapiens

<400> SEQUENCE: 11

```
Trp Lys Phe Glu His Cys
  1               5
```

<210> SEQ ID NO 12
<211> LENGTH: 7
<212> TYPE: PRT
<213> ORGANISM: Homo sapiens

<400> SEQUENCE: 12

```
Trp Lys Phe Glu His Cys Asn
  1               5
```

```
<210> SEQ ID NO 13
<211> LENGTH: 18
<212> TYPE: PRT
<213> ORGANISM: Homo sapiens

<400> SEQUENCE: 13

Trp Lys Phe Glu His Cys Asn Phe Asn Asp Val Thr Thr Arg Leu Arg
1               5                   10                  15

Glu Asn

<210> SEQ ID NO 14
<211> LENGTH: 23
<212> TYPE: PRT
<213> ORGANISM: Homo sapiens

<400> SEQUENCE: 14

Cys Trp Lys Phe Glu His Cys Asn Phe Asn Asp Val Thr Thr Arg Leu
1               5                   10                  15

Arg Glu Asn Glu Leu Thr Tyr
            20

<210> SEQ ID NO 15
<211> LENGTH: 30
<212> TYPE: PRT
<213> ORGANISM: Homo sapiens

<400> SEQUENCE: 15

Ala Gly Leu Gln Val Tyr Asn Lys Cys Trp Lys Phe Glu His Cys Asn
1               5                   10                  15

Phe Asn Asp Val Thr Thr Arg Leu Arg Glu Asn Glu Leu Thr
            20                  25                  30

<210> SEQ ID NO 16
<211> LENGTH: 16
<212> TYPE: PRT
<213> ORGANISM: Homo sapiens

<400> SEQUENCE: 16

Gln Val Tyr Asn Lys Cys Trp Lys Phe Glu His Cys Asn Phe Asn Asp
1               5                   10                  15

<210> SEQ ID NO 17
<211> LENGTH: 17
<212> TYPE: PRT
<213> ORGANISM: Homo sapiens

<400> SEQUENCE: 17

Ala Gly Leu Gln Val Tyr Asn Lys Cys Trp Lys Phe Glu His Cys Asn
1               5                   10                  15

Phe

<210> SEQ ID NO 18
<211> LENGTH: 42
<212> TYPE: PRT
<213> ORGANISM: Homo sapiens

<400> SEQUENCE: 18

Asp Phe Asp Ala Cys Leu Ile Thr Lys Ala Gly Leu Gln Val Tyr Asn
1               5                   10                  15

Lys Cys Trp Lys Phe Glu His Cys Asn Phe Asn Asp Val Thr Thr Arg
            20                  25                  30
```

```
Leu Arg Glu Asn Glu Leu Thr Tyr Tyr Cys
         35                  40
```

```
<210> SEQ ID NO 19
<211> LENGTH: 18
<212> TYPE: PRT
<213> ORGANISM: Homo sapiens

<400> SEQUENCE: 19

Lys Cys Trp Lys Phe Glu His Cys Asn Phe Asn Asp Val Thr Thr Arg
1               5                   10                  15

Leu Arg
```

```
<210> SEQ ID NO 20
<211> LENGTH: 26
<212> TYPE: PRT
<213> ORGANISM: Homo sapiens

<400> SEQUENCE: 20

Lys Cys Trp Lys Phe Glu His Cys Asn Phe Asn Asp Val Thr Thr Arg
1               5                   10                  15

Leu Arg Glu Asn Glu Leu Thr Tyr Tyr Cys
            20                  25
```

```
<210> SEQ ID NO 21
<211> LENGTH: 13
<212> TYPE: PRT
<213> ORGANISM: Homo sapiens

<400> SEQUENCE: 21

Val Tyr Asn Lys Cys Trp Lys Phe Glu His Cys Asn Phe
1               5                   10
```

```
<210> SEQ ID NO 22
<211> LENGTH: 18
<212> TYPE: PRT
<213> ORGANISM: Homo sapiens

<400> SEQUENCE: 22

Gly Leu Gln Val Tyr Asn Lys Cys Trp Lys Phe Glu His Cys Asn Phe
1               5                   10                  15

Asn Asp
```

```
<210> SEQ ID NO 23
<211> LENGTH: 14
<212> TYPE: PRT
<213> ORGANISM: Homo sapiens

<400> SEQUENCE: 23

Tyr Asn Lys Cys Trp Lys Phe Glu His Cys Asn Phe Asn Glu
1               5                   10
```

```
<210> SEQ ID NO 24
<211> LENGTH: 18
<212> TYPE: PRT
<213> ORGANISM: Homo sapiens

<400> SEQUENCE: 24

Ala Gly Leu Gln Val Tyr Asn Lys Cys Trp Lys Phe Glu His Cys Asn
1               5                   10                  15

Phe Asn
```

```
<210> SEQ ID NO 25
<211> LENGTH: 9
<212> TYPE: PRT
<213> ORGANISM: Homo sapiens

<400> SEQUENCE: 25

Asn Lys Cys Trp Lys Phe Glu His Cys
1               5

<210> SEQ ID NO 26
<211> LENGTH: 13
<212> TYPE: PRT
<213> ORGANISM: Homo sapiens

<400> SEQUENCE: 26

Pro Asn Pro Thr Ala Asp Cys Lys Thr Ala Val Asn Cys
1               5                   10

<210> SEQ ID NO 27
<211> LENGTH: 8
<212> TYPE: PRT
<213> ORGANISM: Homo sapiens

<400> SEQUENCE: 27

Asp Cys Lys Thr Ala Val Asn Cys
1               5

<210> SEQ ID NO 28
<211> LENGTH: 13
<212> TYPE: PRT
<213> ORGANISM: Homo sapiens

<400> SEQUENCE: 28

Pro Asn Pro Thr Ala Asp Cys Lys Thr Ala Val Asn Cys
1               5                   10

<210> SEQ ID NO 29
<211> LENGTH: 14
<212> TYPE: PRT
<213> ORGANISM: Homo sapiens

<400> SEQUENCE: 29

Leu Gln Cys Tyr Asn Cys Pro Asn Pro Thr Ala Asp Cys Lys
1               5                   10

<210> SEQ ID NO 30
<211> LENGTH: 13
<212> TYPE: PRT
<213> ORGANISM: Homo sapiens

<400> SEQUENCE: 30

Asp Phe Asp Ala Cys Leu Ile Thr Lys Ala Gly Leu Gln
1               5                   10

<210> SEQ ID NO 31
<211> LENGTH: 14
<212> TYPE: PRT
<213> ORGANISM: Homo sapiens

<400> SEQUENCE: 31

Phe Asp Ala Cys Leu Ile Thr Lys Ala Gly Leu Gln Val Tyr
1               5                   10

<210> SEQ ID NO 32
```

```
<211> LENGTH: 12
<212> TYPE: PRT
<213> ORGANISM: Homo sapiens

<400> SEQUENCE: 32

Cys Leu Ile Thr Lys Ala Gly Leu Gln Val Tyr Asn
1               5                   10

<210> SEQ ID NO 33
<211> LENGTH: 11
<212> TYPE: PRT
<213> ORGANISM: Homo sapiens

<400> SEQUENCE: 33

Asp Phe Asp Ala Cys Leu Ile Thr Lys Ala Gly
1               5                   10

<210> SEQ ID NO 34
<211> LENGTH: 7
<212> TYPE: PRT
<213> ORGANISM: Homo sapiens

<400> SEQUENCE: 34

Gln Val Tyr Asn Lys Cys Trp
1               5

<210> SEQ ID NO 35
<211> LENGTH: 6
<212> TYPE: PRT
<213> ORGANISM: Homo sapiens

<400> SEQUENCE: 35

Val Tyr Asn Lys Cys Trp
1               5

<210> SEQ ID NO 36
<211> LENGTH: 10
<212> TYPE: PRT
<213> ORGANISM: Homo sapiens

<400> SEQUENCE: 36

Ala Gly Leu Gln Val Tyr Asn Lys Cys Trp
1               5                   10

<210> SEQ ID NO 37
<211> LENGTH: 15
<212> TYPE: PRT
<213> ORGANISM: Homo sapiens

<400> SEQUENCE: 37

Ala Gly Leu Gln Val Tyr Asn Lys Cys Trp Lys Phe Glu His Cys
1               5                   10                  15

<210> SEQ ID NO 38
<211> LENGTH: 16
<212> TYPE: PRT
<213> ORGANISM: Homo sapiens

<400> SEQUENCE: 38

Leu Thr Tyr Tyr Cys Cys Lys Lys Asp Leu Cys Asn Phe Asn Glu Gln
1               5                   10                  15

<210> SEQ ID NO 39
<211> LENGTH: 15
<212> TYPE: PRT
```

<213> ORGANISM: Homo sapiens

<400> SEQUENCE: 39

Asn Glu Leu Thr Tyr Tyr Cys Cys Lys Lys Asp Leu Cys Asn Phe
1               5                   10                  15

<210> SEQ ID NO 40
<211> LENGTH: 16
<212> TYPE: PRT
<213> ORGANISM: Homo sapiens

<400> SEQUENCE: 40

Leu Arg Glu Asn Glu Leu Thr Tyr Tyr Cys Cys Lys Lys Asp Leu Cys
1               5                   10                  15

<210> SEQ ID NO 41
<211> LENGTH: 25
<212> TYPE: PRT
<213> ORGANISM: Homo sapiens

<400> SEQUENCE: 41

Cys Asn Phe Asn Asp Val Thr Thr Arg Leu Arg Glu Asn Glu Leu Thr
1               5                   10                  15

Tyr Tyr Cys Cys Lys Lys Asp Leu Cys
            20                  25

<210> SEQ ID NO 42
<211> LENGTH: 8
<212> TYPE: PRT
<213> ORGANISM: Homo sapiens

<400> SEQUENCE: 42

Tyr Cys Cys Lys Lys Asp Leu Cys
1               5

<210> SEQ ID NO 43
<211> LENGTH: 19
<212> TYPE: PRT
<213> ORGANISM: Homo sapiens

<400> SEQUENCE: 43

Thr Thr Arg Leu Arg Glu Asn Glu Leu Thr Tyr Tyr Cys Cys Lys Lys
1               5                   10                  15

Asp Leu Cys

<210> SEQ ID NO 44
<211> LENGTH: 21
<212> TYPE: PRT
<213> ORGANISM: Homo sapiens

<400> SEQUENCE: 44

Val Thr Thr Arg Leu Arg Glu Asn Glu Leu Thr Tyr Tyr Cys Cys Lys
1               5                   10                  15

Lys Asp Leu Cys Asn
            20

<210> SEQ ID NO 45
<211> LENGTH: 21
<212> TYPE: PRT
<213> ORGANISM: Homo sapiens

<400> SEQUENCE: 45

Phe Asn Asp Val Thr Thr Arg Leu Arg Glu Asn Glu Leu Thr Tyr Tyr

```
                 1               5                   10                  15

Cys Cys Lys Lys Asp
                 20

<210> SEQ ID NO 46
<211> LENGTH: 16
<212> TYPE: PRT
<213> ORGANISM: Homo sapiens

<400> SEQUENCE: 46

Gly Thr Ser Leu Ser Glu Lys Thr Val Leu Leu Val Thr Pro Phe
1               5                   10                  15

<210> SEQ ID NO 47
<211> LENGTH: 14
<212> TYPE: PRT
<213> ORGANISM: Homo sapiens

<400> SEQUENCE: 47

Leu Ser Glu Lys Thr Val Leu Leu Leu Val Thr Pro Phe Leu
1               5                   10

<210> SEQ ID NO 48
<211> LENGTH: 10
<212> TYPE: PRT
<213> ORGANISM: Homo sapiens

<400> SEQUENCE: 48

Thr Ser Leu Ser Glu Lys Thr Val Leu Leu
1               5                   10

<210> SEQ ID NO 49
<211> LENGTH: 13
<212> TYPE: PRT
<213> ORGANISM: Homo sapiens

<400> SEQUENCE: 49

Leu Glu Asn Gly Gly Thr Ser Leu Ser Glu Lys Thr Val
1               5                   10
```